US010351631B2

(12) United States Patent
Keyt et al.

(10) Patent No.: US 10,351,631 B2
(45) Date of Patent: Jul. 16, 2019

(54) CONSTANT CHAIN MODIFIED BISPECIFIC, PENTA- AND HEXAVALENT IG-M ANTIBODIES

(71) Applicant: IGM Biosciences, Inc., Mountain View, CA (US)

(72) Inventors: Bruce Alan Keyt, Hillsborough, CA (US); Fen Zhang, San Francisco, CA (US); Leonard George Presta, San Francisco, CA (US); Rency Yoshimura, Santa Clara, CA (US)

(73) Assignee: IGM BIOSCIENCES, INC., Mountain View, CA (US)

( * ) Notice: Subject to any disclaimer, the term of this patent is extended or adjusted under 35 U.S.C. 154(b) by 0 days.

(21) Appl. No.: 14/916,166

(22) PCT Filed: Sep. 4, 2014

(86) PCT No.: PCT/US2014/054079
§ 371 (c)(1),
(2) Date: Mar. 2, 2016

(87) PCT Pub. No.: WO2015/053887
PCT Pub. Date: Apr. 16, 2015

(65) Prior Publication Data
US 2016/0222132 A1 Aug. 4, 2016

Related U.S. Application Data

(60) Provisional application No. 61/874,277, filed on Sep. 5, 2013, provisional application No. 61/874,284, filed on Sep. 5, 2013.

(51) Int. Cl.
*C07K 16/00* (2006.01)
*A61K 39/00* (2006.01)
*C07K 16/46* (2006.01)
*C07K 16/28* (2006.01)

(52) U.S. Cl.
CPC ............ *C07K 16/468* (2013.01); *C07K 16/00* (2013.01); *C07K 16/2809* (2013.01); *C07K 16/2887* (2013.01); *C07K 16/461* (2013.01); C07K 2317/24 (2013.01); C07K 2317/31 (2013.01); C07K 2317/35 (2013.01); C07K 2317/52 (2013.01); C07K 2317/522 (2013.01); C07K 2317/524 (2013.01); C07K 2317/526 (2013.01); C07K 2317/528 (2013.01); C07K 2317/64 (2013.01)

(58) Field of Classification Search
None
See application file for complete search history.

(56) References Cited

U.S. PATENT DOCUMENTS

| 4,816,567 | A | 3/1989 | Cabilly et al. |
| 8,349,332 | B2* | 1/2013 | Chang .............. A61K 47/48415 424/130.1 |
| 8,377,435 | B2 | 2/2013 | Bhat |
| 9,409,976 | B2 | 8/2016 | Teng |
| 9,458,241 | B2 | 10/2016 | Bhat |
| 9,938,347 | B2 | 4/2018 | Wang |
| 9,951,134 | B2 | 4/2018 | Keyt |
| 2002/0062010 | A1* | 5/2002 | Arathoon ................ C07K 16/00 530/388.1 |
| 2006/0063234 | A1 | 3/2006 | Jones |
| 2007/0014794 | A1* | 1/2007 | Carter .............. C07K 14/70514 424/143.1 |
| 2010/0286374 | A1* | 11/2010 | Kannan ................ C07K 16/468 530/387.3 |
| 2010/0316645 | A1* | 12/2010 | Imhof-Jung ........... C07K 16/22 424/136.1 |
| 2013/0089547 | A1* | 4/2013 | Tso ..................... C07K 16/2803 424/134.1 |
| 2013/0129723 | A1 | 5/2013 | Blankenship et al. |
| 2016/0326233 | A1 | 11/2016 | Mondelli |
| 2016/0368971 | A1 | 12/2016 | Keyt |
| 2017/0283510 | A1 | 10/2017 | Keyt |
| 2018/0009897 | A1 | 1/2018 | Wang |
| 2018/0118814 | A1 | 5/2018 | Carroll |
| 2018/0118816 | A1 | 5/2018 | Keyt |

FOREIGN PATENT DOCUMENTS

| JP | 2008512987 | 5/2008 |
| JP | 2011508604 | 3/2011 |
| WO | WO 1989/001975 | 3/1898 |
| WO | WO 1996/027011 | 9/1996 |
| WO | 2006008548 | 1/2006 |
| WO | WO 2006/008548 A2 | 1/2006 |

(Continued)

OTHER PUBLICATIONS

Muller et al., PNAS, 2013, 110:10183-10188 (Year: 2013).*
Kontermann et al. (Bispecific Antibodies, 2011, pp. 1-373), (Year: 2011).*
Atwell et al., "Stable heterodimers from remodeling the domain interface of a homodimer using a phage display library," J. Mol. Biol. 1997, vol. 270, pp. 26-35.
Choi et al., "Recombinant chimeric OKT3 scFv IgM antibodies mediate immune suppression while reducing T cell activation in vitro," Eur J Immunol. 2001, vol. 31, No. 1, pp. 94-106.

(Continued)

Primary Examiner — Julie Wu
(74) Attorney, Agent, or Firm — FisherBroyles, LLP

(57) ABSTRACT

The present invention concerns binding molecules having a penta- or hexameric ring structure, such as, for example, isolated IgM antibodies with five or six bispecific binding units, and methods and means for making and using the same. The invention further concerns multi-specific binding molecules having a penta- or hexameric ring structure, such as, for example, isolated IgM antibodies with five or six bispecific binding units, and methods and means for making and using the same.

22 Claims, 30 Drawing Sheets

Specification includes a Sequence Listing.

(56) References Cited

FOREIGN PATENT DOCUMENTS

| WO | 2009089004 | 7/2009 |
|---|---|---|
| WO | WO 2009/089004 A1 | 7/2009 |
| WO | 2013049254 | 4/2013 |
| WO | 2013096291 | 6/2013 |
| WO | 2016141303 | 9/2016 |
| WO | 2017059380 | 4/2017 |
| WO | 2017059387 | 4/2017 |
| WO | 2017196867 | 11/2017 |
| WO | 2018017761 | 1/2018 |
| WO | 2018017763 | 1/2018 |
| WO | 2018017888 | 1/2018 |
| WO | 2018017889 | 1/2018 |

OTHER PUBLICATIONS

Clackson et al., "Making antibody fragments using phage display libraries," Nature, 1991, vol. 352, pp. 624-628.

Czajkowsky and Shao, "The human IgM pentamer is a mushroom-shaped molecule with a flexural bias," PNAS 2009, vol. 106, No. 35, pp. 14960-14965.

Diaz, Maria Aiko Angela A., "Effects of engineering charged amino acids in the $C_H3$ domains on antibody heavy chain dimerization," Philippine Science Letters, 2011, vol. 4, No. 1, pp. 48-55.

Ellman, "Biosynthetic method for introducing unnatural amino acids site-specifically into proteins," Meth. Enzym. 1991, vol. 202, pp. 301-336.

Fegan, et al., "Chemically self-assembled antibody nanostructures as potential drug carriers," Mol Pharm. 2012, vol. 9, No. 11, pp. 3218-3227.

GenBank Accession No. AFM37312.1 (2 pages).
GenBank Accession No. CAB37838.1 (2 pages).
GenBank Accession No. CAC20458.1 (2 pages).
GenBank Accession No. J00260.1 (2 pages).
GenBank Accession No. X14940.1 (3 pages).
GenBank Accession No. X57331.1 (7 pages).

Giesse et al., "Eukaryotic expression systems: a comparison," Protein Expr. Purif. 1996, vol. 8, pp. 271-282.

Gunasekaran et al., "Enhancing antibody Fc heterodimer formation through electrostatic steering effects: applications to bispecific molecules and monovalent IgG," J. Biol. Chem. 2010, vol. 285, No. 25, pp. 19637-19646.

Jones et al., "Replacing the complementarity-determining regions in a human antibody with those from a mouse," Nature 1986, vol. 321, pp. 522-525.

Kaufman, R. J., "Overview of vector design for mammalian gene expression.," Mol. Biotechnol. 2000, vol. 16, No. 2, pp. 151-161.

Klein et al., "Progress in overcoming the chain association issue in bispecific heterodimeric IgG antibodies," MAbs 2012, vol. 4, No. 6, pp. 653-663.

Kohler et al., "Continuous cultures of fused cells secreting antibody of predefined specificity," Nature, 1975, vol. 256, p. 495.

Makrides, S.C., "Components of vectors for gene transfer and expression in mammalian cells," Protein Expr. Purif. 1999, vol. 17, pp. 183-202.

Marks et al., "By-passing immunization. Human antibodies from V-gene libraries displayed on phage," J. Mol. Biol. 1991, vol. 222, pp. 581-597.

Merchant et al., "An efficient route to human bispecific IgG," Nat Biotechnol 1998, vol. 16, pp. 677-681.

Morrison et al., "Chimeric human antibody molecules: mouse antigen-binding domains with human constant region domains," PNAS 1984, vol. 81, pp. 6851-6855.

Noren et al., "A general method for site-specific incorporation of unnatural amino acids into proteins," Science 1989, vol. 244, p. 182-188.

Ponders and Richards, "Tertiary templates for proteins. Use of packing criteria in the enumeration of allowed sequences for different structural classes," J. Mol. Biol., 1987, vol. 193, pp. 775-791.

Presta, "Antibody engineering," Curr. Op. Struct. Biol. 1992, vol. 2, pp. 593-596.

Ridgway, et al., "'Knobs-into-holes' engineering of antibody CH3 domains for heavy chain heterodimerization," Protein Eng. 1996 vol. 9, No. 7, pp. 617-621.

Riechmann et al., "Reshaping human antibodies for therapy," Nature 1988, vol. 332, pp. 323-329.

Schaeffer et al., "Immunoglobulin domain crossover as a generic approach for the production of bispecific IgG antibodies," PNAS 2011, vol. 108, No. 27, pp. 11187-11192.

Werner, R. G., "Appropriate mammalian expression systems for biopharmaceuticals," Drug Res. 1998, vo. 48, pp. 870-880.

Wood et al., "High level synthesis of immunoglobulins in Chinese hamster ovary cells," J. Immunol. 1990, vol. 145, pp. 3011-3016.

Zhu et al., "Remodeling domain interfaces to enhance heterodimer formation," Prot. Sci. 1997, vol. 6, 781-788.

* cited by examiner

Constant domains CG1/CB1/CM1

```
CB1  ASTQSPSVFPLTRCCKNIPSNATSVPLGCLATGYFPEPVMVTWDTGSLNGTT --MTLPATTLTL
CG1  ASTKGPSVFPLAPSSKSTS --GGTAALGCLVKDYFPEPVTVSWNSGALTSGV --HTFPAVLQSS
      1         10         20         30         40         50         60
      *          *          *          *          *          *          *
CM1  GSASAPTLFPLVSCENSPSD --TSSVAVGCLAQDFLPDSITLSWKYRNNSDISSTRGFPSVLRGGKY
                                                                         H

CB1  SGHYATISLLTVSGAWAKQMFTCRVAHTPSSTDWVDNKTFS
CG1  GLYSLSSVVTVPSS SLGTQTYICNVNHKPSNTKVDKKV
      70         80         90         100
      *          *          *          *
CM1  AATSQVLLPSKDVMQGTDEHVVCKVQHPNGNKEKNVPLP
```

FIG. 4A

```
Constant domains CG2/CE3/CM3

330       340       350       360       370       380
            *         *         *         *         *         *
            ssss  hhhhhh          ssssssss                 ssssss
CE3    -ADSMPRGVSAYLSRPSPFDLFIRKSPTTTCLVVDLAPSKGTVNLTWSRASGKPVNHSTR 220       230       240       250       260       270
            *         *         *         *         *         *
            ssss   hhhhhh          ssssss                ssssss    sss
CG2    APELLGGPSVFLFPPKPKDTLMISRTPEVTCVVVDVSHEDPEVKFNWYVDGVEVHNAKTK 240       250       260       270
                                *         *         *         *
                                                                      *
CM3    -VPDQDTAIRVFAIPPSFASIFLKSTKLTCLVTDLTTYD -SVTISWTRQNGEAVKTHTN
        G I   S 390       400       410       420       430
            *         *         *         *         *
            ssss  ssss  hhhhhh          ssssss         ssssss
CE3    KEEKQRNGTLTVTSTLPVGTRDWIEGETYQCRVTHPHLPRALMRSTTKTS 280       290       300       310       320
            *         *         *         *         *
            ssssssss  hhhhhh         sssss            sssss
CG2    PREEQYNSTYRVVSVLTVLHQDWLNGKEYKCKVSNKALPAPIEKTISKAK 280       290       300       310       320
            *         *         *         *         *
CM3    ISESHPKATFSAVGEASICEDDWNSGERFTCTVTHTDLPSPLKQTISRPK
```

FIG. 4C

Constant domains CG3/ CE4/CM4

```
         440       450       460       470       480       490
           *         *         *         *         *         *
         ssssss           ssssssssss       ssssssssss    hhh sssss
CE4   --GERAAEHVYAPATPEWPGSR--DKRTLACLIQN FMPEDISYQWLMEVQLPDARHSYTQPRKTK
         350       360       370       380       390       400
           *         *         *         *         *         * sssss hhhhh                    sssssssss       sss        ss
CG3   --CQPREPQVYTLPPSRDELTK--NQVSLTCLVKGFYPSDIAVEWESNGQPRNN --YKTTPPVLDS
         330       340       350       360       370       380
           *         *         *         *         *         *

CM4   GVALHRPDVYLLPPAREQLNLRESATITCLVTGFSPADVFVQWMQRGQPLSPEK   YVTSAPMPEP 500       510       520       530       540
           *         *         *         *         *
         ssssssssshhhhhh   ssssss            ssssss
CE4   --CSGFFVFSKLEVTRAEWEQKDEFICRAVHEAASPSQTVQRAVSVNPGK
         410       420       430       440
           *         *         *         * sssssssshhhhhh       ssssss   hhhhhksssss
CG3   ---DGSFFLYSKLTVDKSRWQQGNVFSCSVMHEALHNHYTQKSLSLSPGK
         390       400       410       420       430
           *         *         *         *         *

CM4   QAPGRYFAHSILTVSEEEWNTGETYTCVVAHEALPNRVTERTVDKSTGKPTLYNVSLVMSDTAGTCY
                                                                    440                                                                450
                                                                      *                                                                  *
```

FIG. 4D

Table A

Human IgM CM4 domain interface residues
Knobs-Holes and charge change positions
================================================================
Set #1
Knob (CM4 #1)
Residue #       Native Seq       Potential Mutations
350             T                Y Hole (CM4 #2): any combination
Residue #       Native Seq       Potential Mutations
352             L                S
393             F                F (W)
395             H                A (V,I,L,S,T)
================================================================
Set #2 (additions to set #1)
Knob (CM4 #1)
Residue #       Native Seq       Potential Mutations
354             T                D,E
397             I                D,E Hole (CM4 #2)
Residue #       Native Seq       Potential Mutations
354             T                K,R
397             I                K,R
================================================================
Set #3 (additions to set #1)
Knob (CM4 #1)
Residue #       Native Seq       Potential Mutations
354             T                K,R
397             I                K,R Hole (CM4 #2)
Residue #       Native Seq       Potential Mutations
354             T                D,E
397             I                D,E
================================================================
Set #4
Knob (CM4 #1)
Residue #       Native Seq       Potential Mutations
350             T                Y
395             H                Y Hole (CM4 #2): any combination
Residue #       Native Seq       Potential Mutations
352             L                S

FIG. 11A

```
393              F                    F (W)
395              H                    A (V,I,L)
397              I                    T (S)
=============================================================
Set #5 (additions to set #4)
Knob (CM4 #1)
Residue #        Native Seq           Potential Mutations
354              T                    D,E
397              I                    D,E Hole (CM4 #2)
Residue #        Native Seq           Potential Mutations
354              T                    K,R
397              I                    K,R
=============================================================
Set #6 (additions to set #4)
Knob (CM4 #1)
Residue #        Native Seq           Potential Mutations
354              T                    K,R
397              I                    K,R Hole (CM4 #2)
Residue #        Native Seq           Potential Mutations
354              T                    D,E
397              I                    D,E
=============================================================
Set #7
Knob (CM4 #1)
Residue #        Native Seq           Potential Mutations
350              T                    Y
395              H                    F Hole (CM4 #2): any combination
Residue #        Native Seq           Potential Mutations
350              T                    V (A,I,L)
352              L                    S
393              F                    F (W)
395              H                    A (V,I,L)
=============================================================
Set #8 (additions to set #7)
Knob (CM4 #1)
Residue #        Native Seq           Potential Mutations
354              T                    D,E
397              I                    D,E Hole (CM4 #2)
Residue #        Native Seq           Potential Mutations
```

FIG. 11B

```
354              T               K,R
397              I               K,R
========================================================
Set #9 (additions to set #7)
Knob (CM4 #1)
Residue #        Native Seq      Potential Mutations
354              T               K,R
397              I               K,R Hole (CM4 #2)
Residue #        Native Seq      Potential Mutations
354              T               D,E
397              I               D,E
========================================================
Set #10
Knob (CM4 #1)
Residue #        Native Seq      Potential Mutations
350              T               F Hole (CM4 #2): any combination
Residue #        Native Seq      Potential Mutations
352              L               A
393              F               F (W)
395              K               A (V,I,L,S,T)
========================================================
Set #11 (additions to set #10)
Knob (CM4 #1)
Residue #        Native Seq      Potential Mutations
354              T               D,E
397              I               D,E Hole (CM4 #2)
Residue #        Native Seq      Potential Mutations
354              T               K,R
397              I               K,R
========================================================
Set #12 (additions to set #10)
Knob (CM4 #1)
Residue #        Native Seq      Potential Mutations
354              T               K,R
397              I               K,R Hole (CM4 #2)
Residue #        Native Seq      Potential Mutations
354              T               D,E
397              I               D,E
========================================================
```

FIG. 11C

```
Set #13
Knob (CH4 #1)
Residue #       Native Seq          Potential Mutations
350             T                   F
395             H                   Y Hole (CH4 #2): any combination
Residue #       Native Seq          Potential Mutations
352             L                   A
353             F                   P (W)
395             H                   A (V,I,L)
397             I                   T (S)
===========================================================
Set #14 (additions to set #13)
Knob (CH4 #1)
Residue #       Native Seq          Potential Mutations
354             T                   D,E
397             I                   D,E Hole (CH4 #2)
Residue #       Native Seq          Potential Mutations
354             T                   K,R
397             I                   K,R
===========================================================
Set #15 (additions to set #13)
Knob (CH4 #1)
Residue #       Native Seq          Potential Mutations
354             T                   K,R
397             I                   K,R Hole (CH4 #2)
Residue #       Native Seq          Potential Mutations
354             T                   D,E
397             I                   D,E
===========================================================
Set #16
Knob (CH4 #1)
Residue #       Native Seq          Potential Mutations
350             T                   F
395             H                   F Hole (CH4 #2): any combination
Residue #       Native Seq          Potential Mutations
350             T                   V (A,I,L)
352             L                   A
353             F                   P (W)
395             H                   A (V,I,L)
```

FIG. 11D

```
Set #17 (additions to set #16)
Knob (CM4 #1)
Residue #      Native Seq     Potential Mutations
354            T              D,E
397            I              D,E Hole (CM4 #2)
Residue #      Native Seq     Potential Mutations
354            T              K,R
397            I              K,R Set #18 (additions to set #16)
Knob (CM4 #1)
Residue #      Native Seq     Potential Mutations
354            T              K,R
397            I              K,R Hole (CM4 #2)
Residue #      Native Seq     Potential Mutations
354            T              D,E
397            I              D,E Set #19
Knob (CM4 #1)
Residue #      Native Seq     Potential Mutations
350            T              W Hole (CM4 #2); any combination
Residue #      Native Seq     Potential Mutations
352            L              G (A)
393            F              F (W)
395            H              A (V,S,T)

Set #20 (additions to set #19)
Knob (CM4 #1)
Residue #      Native Seq     Potential Mutations
354            T              D,E
397            I              D,E Hole (CM4 #2)
Residue #      Native Seq     Potential Mutations
354            T              K,R
397            I              K,R Set #21 (additions to set #19)
Knob (CM4 #1)
```

FIG. 11E

```
Residue #      Native Seq       Potential Mutations
354            T                K,R
397            I                K,R Hole (CM4 #2)
Residue #      Native Seq       Potential Mutations
354            T                D,E
397            I                D,E
------------------------------------------------------
Set #22
Knob (CM4 #1)
Residue #      Native Seq       Potential Mutations
350            T                W
395            H                Y Hole (CM4 #2); any combination
Residue #      Native Seq       Potential Mutations
352            L                G (A)
393            F                F (W)
395            H                A (V,I,L)
397            I                T (S)
------------------------------------------------------
Set #23 (additions to set #22)
Knob (CM4 #1)
Residue #      Native Seq       Potential Mutations
354            T                D,E
397            I                D,E Hole (CM4 #2)
Residue #      Native Seq       Potential Mutations
354            T                K,R
397            I                K,R
------------------------------------------------------
Set #24 (additions to set #22)
Knob (CM4 #1)
Residue #      Native Seq       Potential Mutations
354            T                K,R
397            I                K,R Hole (CM4 #2)
Residue #      Native Seq       Potential Mutations
354            T                D,E
397            I                D,E
------------------------------------------------------
Set #25
Knob (CM4 #1)
Residue #      Native Seq       Potential Mutations
```

Hole (CM4 #2): any combination
Residue #       Native Seq              Potential Mutations
350             T                       V (A,I,L)
353             L                       G (A)
393             P                       F (W)
395             H                       A (V,I,L)
================================================================
Set #26 (additions to set #25)
Knob (CM4 #1)
Residue #       Native Seq              Potential Mutations
354             T                       D,E
397             I                       D,E Hole (CM4 #2)
Residue #       Native Seq              Potential Mutations
354             T                       K,R
397             I                       K,R
================================================================
Set #27 (additions to set #25)
Knob (CM4 #1)
Residue #       Native Seq              Potential Mutations
354             T                       K,R
397             I                       K,R Hole (CM4 #2)
Residue #       Native Seq              Potential Mutations
354             T                       D,E
397             I                       D,E
================================================================
Set #28
Knob (CM4 #1)
Residue #       Native Seq              Potential Mutations
334             L                       C
350             T                       W (F)
395             H                       P Hole (CM4 #2): any combination
Residue #       Native Seq              Potential Mutations
334             L                       C
350             T                       M
352             L                       A (V)
393             P                       F (W)
395             H                       M (I)
================================================================
```

FIG. 11G

```
Set #29 (additions to set #28)
Knob (CM4 #1)
Residue #      Native Seq        Potential Mutations
354            T                 D,E
397            I                 D,E Hole (CM4 #2)
Residue #      Native Seq        Potential Mutations
354            T                 K,R
397            I                 K,R
================================================================
Set #30 (additions to set #28)
Knob (CM4 #1)
Residue #      Native Seq        Potential Mutations
354            T                 K,R
397            I                 K,R Hole (CM4 #2)
Residue #      Native Seq        Potential Mutations
354            T                 D,E
397            I                 D,E
================================================================
```

FIG. 11H

Table 8

Human IgM CM4 domain interface residues
Potential Charge Swaps in CM4 domain
------------------------------------------------------------

Set #1
CM4 Chain #1
| Residue # | Native Seq | Potential Mutations |
|---|---|---|
| 328 | R | E (D) |

CM4 Chain #2
| Residue # | Native Seq | Potential Mutations |
|---|---|---|
| 339 | E | R (K) |

------------------------------------------------------------
Set #2
CM4 Chain #1
| Residue # | Native Seq | Potential Mutations |
|---|---|---|
| 344 | R | E (D) |

CM4 Chain #2
| Residue # | Native Seq | Potential Mutations |
|---|---|---|
| 330 | D | R (K) |

------------------------------------------------------------
Set #3
CM4 Chain #1
| Residue # | Native Seq | Potential Mutations |
|---|---|---|
| 376 | K | E (D) |

CM4 Chain #2
| Residue # | Native Seq | Potential Mutations |
|---|---|---|
| 385 | E | R (K) |

------------------------------------------------------------
Set #4
CM4 Chain #1
| Residue # | Native Seq | Potential Mutations |
|---|---|---|
| 427 | R | E (D) |

CM4 Chain #2
| Residue # | Native Seq | Potential Mutations |
|---|---|---|
| 339 | E | R (K) |

```
Table C

Human IgN CH2 domain interface residues
Charge Introductions
===========================================================
Set #1
CH2 Chain #1
Residue #        Native Seq          Potential Mutations
116              F                   E (D)
133              I                   E (D)

CH2 Chain #2
Residue #        Native Seq          Potential Mutations
116              F                   K (K)
133              I                   K (K)
===========================================================
```

FIG. 13

Table D

Human IgM CM2 domain interface residues
Knobs-Holes

Set #1
Knob (CM2 #1)

| Residue # | Native Seq | Potential Mutations |
|---|---|---|
| 119 | P | W |

Hole (CM2 #2): any combination

| Residue # | Native Seq | Potential Mutations |
|---|---|---|
| 115 | V | V (I) |
| 117 | V | G (A,S) |
| 132 | L | M (A) |
| 189 | W | V (I,L,M,F) |
| 210 | A | G |

Set #2
Knob (CM2 #1)

| Residue # | Native Seq | Potential Mutations |
|---|---|---|
| 116 | F | E (D) |
| 119 | P | W |
| 133 | I | E (D) |

Hole (CM2 #2): any combination

| Residue # | Native Seq | Potential Mutations |
|---|---|---|
| 115 | V | V (I) |
| 116 | F | R (K) |
| 117 | V | G (A,S) |
| 132 | L | M (A) |
| 133 | I | R (K) |
| 189 | W | V (I,L,M,F) |
| 210 | A | G |

Set #3

Knob (CM2 #1)

| Residue # | Native Seq | Potential Mutations |
|---|---|---|
| 116 | F | R (K) |
| 119 | P | W |
| 133 | I | R (K) |

Hole (CM2 #2): any combination

| Residue # | Native Seq | Potential Mutations |
|---|---|---|
| 115 | V | V (I) |
| 116 | F | E (D) |
| 117 | V | G (A,S) |

Table E

Human IgM CM2 domain interface residues
Charge Exchanges

Set #1
CM2 Chain #1

| Residue # | Native Seq | Potential Mutations |
|---|---|---|
| 167 | E | K (R) |

CM2 Chain #2

| Residue # | Native Seq | Potential Mutations |
|---|---|---|
| 177 | K | E (D) |

Set #2
CM2 Chain #1

| Residue # | Native Seq | Potential Mutations |
|---|---|---|
| 169 | K | E (D) |

CM2 Chain #2

| Residue # | Native Seq | Potential Mutations |
|---|---|---|
| 170 | E | K (R) |

Set #3
CM2 Chain #1

| Residue # | Native Seq | Potential Mutations |
|---|---|---|
| 170 | E | K (R) |

CM2 Chain #2

| Residue # | Native Seq | Potential Mutations |
|---|---|---|
| 177 | K | E (D) |

Set #4
CM2 Chain #1

| Residue # | Native Seq | Potential Mutations |
|---|---|---|
| 167 | E | K (R) |
| 169 | K | E (D) |

CM2 Chain #2

| Residue # | Native Seq | Potential Mutations |
|---|---|---|
| 170 | E | K (R) |
| 177 | K | E (D) |

FIG. 15

```
Table 8

Human IgM CM2, CM3 and CM4 domain interface residues
Charge Exchanges
================================================================
Set #1
CM3 Chain #1
Residue #      Native Seq      Potential Mutations
121            D               K (R)

CM3 Chain #2
Residue #      Native Seq      Potential Mutations
315            K               D (E)
================================================================
Set #2
CM2 Chain #1
Residue #      Native Seq      Potential Mutations
190            K               E (D)

CM4 Chain #2
Residue #      Native Seq      Potential Mutations
385            E               K (R)
================================================================
Set #3
CM2 Chain #1
Residue #      Native Seq      Potential Mutations
185            K               E (D)

CM4 Chain #2
Residue #      Native Seq      Potential Mutations
360            D               K (R)
================================================================
Set #4
CM2 Chain #1
Residue #      Native Seq      Potential Mutations
121            D               K (R)
190            K               E (D)

CM3/CM4 Chain #2
Residue #      Native Seq      Potential Mutations
315            K               D (E)
385            E               K (R)
================================================================
Set #5
CM2 Chain #1
Residue #      Native Seq      Potential Mutations
121            D               K (R)
```

CM3/CM4 Chain #2
Residue #        Native Seq           Potential Mutations
315              K                    D (E)
360              D                    K (R)
----------------------------------------------------------------
Set #6
CM2 Chain #1
Residue #        Native Seq           Potential Mutations
150              K                    E (D)
185              K                    E (D)

CM4 Chain #2
Residue #        Native Seq           Potential Mutations
360              D                    K (R)
385              E                    K (R)
----------------------------------------------------------------
Set #7
CM2 Chain #1
Residue #        Native Seq           Potential Mutations
121              D                    K (R)
150              K                    E (D)
185              K                    E (D)

CM3/CM4 Chain #2
Residue #        Native Seq           Potential Mutations
315              K                    D (E)
360              D                    K (R)
385              E                    K (R)
----------------------------------------------------------------
```

FIG. 16B

SEQUENCE LISTING

```
<160> NUMBER OF SEQ ID NOS: 33

<210> SEQ ID NO 1
<211> LENGTH: 551
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ser Gly Ser Ala Ser Ala Pro Thr
        115                 120                 125
```

```
Leu Phe Pro Leu Val Ser Cys Glu Asn Ser Pro Ser Asp Thr Ser Ser
    130                 135                 140

Val Ala Val Gly Cys Leu Ala Gln Asp Phe Leu Pro Asp Ser Ile Thr
145                 150                 155                 160

Phe Ser Trp Lys Tyr Lys Asn Asn Ser Asp Ile Ser Ser Thr Arg Gly
                165                 170                 175

Phe Pro Ser Val Leu Arg Gly Gly Lys Tyr Ala Ala Thr Ser Gln Val
                180                 185                 190

Leu Leu Pro Ser Lys Asp Val Met Gln Gly Thr Asp Glu His Val Val
            195                 200                 205

Cys Lys Val Gln His Pro Asn Gly Asn Lys Glu Lys Asn Val Pro Leu
210                 215                 220

Pro Val Ile Ala Glu Leu Pro Pro Lys Val Ser Val Phe Val Pro Pro
225                 230                 235                 240

Arg Asp Gly Phe Phe Gly Asn Pro Arg Lys Ser Lys Leu Ile Cys Gln
                245                 250                 255

Ala Thr Gly Phe Ser Pro Arg Gln Ile Gln Val Ser Trp Leu Arg Glu
                260                 265                 270

Gly Lys Gln Val Gly Ser Gly Val Thr Thr Asp Gln Val Gln Ala Glu
            275                 280                 285

Ala Lys Glu Ser Gly Pro Thr Thr Tyr Lys Val Thr Ser Thr Leu Thr
290                 295                 300

Ile Lys Glu Ser Asp Trp Leu Ser Gln Ser Met Phe Thr Cys Arg Val
305                 310                 315                 320

Asp His Arg Gly Leu Thr Phe Gln Gln Asn Ala Ser Ser Met Cys Val
                325                 330                 335

Pro Asp Gln Asp Thr Ala Ile Arg Val Phe Ala Ile Pro Pro Ser Phe
            340                 345                 350

Ala Ser Ile Phe Leu Thr Lys Ser Thr Lys Leu Thr Cys Leu Val Thr
            355                 360                 365

Asp Leu Thr Thr Tyr Asp Ser Val Thr Ile Ser Trp Thr Arg Gln Asn
            370                 375                 380

Gly Glu Ala Val Lys Thr His Thr Asn Ile Ser Glu Ser His Pro Asn
385                 390                 395                 400

Ala Thr Phe Ser Ala Val Gly Glu Ala Ser Ile Ser Glu Asp Asp Trp
                405                 410                 415

Asn Ser Gly Glu Arg Phe Thr Cys Thr Val Thr His Thr Asp Leu Pro
                420                 425                 430

Ser Pro Leu Lys Gln Thr Ile Ser Arg Pro Lys Gly Val Ala Leu His
            435                 440                 445

Arg Pro Asp Val Tyr Leu Leu Pro Pro Ala Arg Glu Gln Leu Asn Leu
450                 455                 460

Arg Glu Ser Ala Thr Ile Thr Cys Leu Val Thr Gly Phe Ser Pro Ala
465                 470                 475                 480

Asp Val Phe Val Gln Trp Met Gln Arg Gly Gln Pro Leu Ser Pro Glu
                485                 490                 495

Lys Tyr Val Thr Ser Ala Pro Met Pro Glu Pro Gln Ala Pro Gly Arg
                500                 505                 510

Tyr Phe Ala His Ser Ile Leu Thr Val Ser Glu Glu Trp Asn Thr
            515                 520                 525

Gly Glu Thr Tyr Thr Cys Val Val Ala His Glu Ala Leu Pro Asn Arg
530                 535                 540
```

Val Thr Glu Arg Thr Val Asp
545                 550

<210> SEQ ID NO 2
<211> LENGTH: 353
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gly Ser Gly Ser Lys Val Ser Val Phe Val Pro Pro Arg Asp Gly Phe
1               5                   10                  15

Phe Gly Asn Pro Arg Lys Ser Lys Leu Ile Cys Gln Ala Thr Gly Phe
                20                  25                  30

Ser Pro Arg Gln Ile Gln Val Ser Trp Leu Arg Glu Gly Lys Gln Val
            35                  40                  45

Gly Ser Gly Val Thr Thr Asp Gln Val Gln Ala Glu Ala Lys Glu Ser
50                  55                  60

Gly Pro Thr Thr Tyr Lys Val Thr Ser Thr Leu Thr Ile Lys Glu Ser
65                  70                  75                  80

Asp Trp Leu Ser Gln Ser Met Phe Thr Cys Arg Val Asp His Arg Gly
                85                  90                  95

Leu Thr Phe Gln Gln Asn Ala Ser Ser Met Cys Val Pro Asp Gln Asp
            100                 105                 110

Thr Ala Ile Arg Val Phe Ala Ile Pro Pro Ser Phe Ala Ser Ile Phe
        115                 120                 125

Leu Thr Lys Ser Thr Lys Leu Thr Cys Leu Val Thr Asp Leu Thr Thr
130                 135                 140

Tyr Asp Ser Val Thr Ile Ser Trp Thr Arg Gln Asn Gly Glu Ala Val
145                 150                 155                 160

Lys Thr His Thr Asn Ile Ser Glu Ser His Pro Asn Ala Thr Phe Ser
                165                 170                 175

Ala Val Gly Glu Ala Ser Ile Ser Glu Asp Asp Trp Asn Ser Gly Glu
            180                 185                 190

Arg Phe Thr Cys Thr Val Thr His Thr Asp Leu Pro Ser Pro Leu Lys
        195                 200                 205

Gln Thr Ile Ser Arg Pro Lys Gly Val Ala Leu His Arg Pro Asp Val
210                 215                 220

Tyr Leu Leu Pro Pro Ala Arg Glu Gln Leu Asn Leu Arg Glu Ser Ala
225                 230                 235                 240

Thr Ile Thr Cys Leu Val Thr Gly Phe Ser Pro Ala Asp Val Phe Val
                245                 250                 255

Gln Trp Met Gln Arg Gly Gln Pro Leu Ser Pro Glu Lys Tyr Val Thr
            260                 265                 270

Ser Ala Pro Met Pro Glu Pro Gln Ala Pro Gly Arg Tyr Phe Ala His
        275                 280                 285

Ser Ile Leu Thr Val Ser Glu Glu Glu Trp Asn Thr Gly Glu Thr Tyr
290                 295                 300

Thr Cys Val Val Ala His Glu Ala Leu Pro Asn Arg Val Thr Glu Arg
305                 310                 315                 320

Thr Val Asp Lys Ser Thr Gly Lys Gly Gly Ser Glu Gln Lys Leu
                325                 330                 335

Ile Ser Glu Glu Asp Leu Asn Ser Ala Val Asp His His His His
            340                 345                 350

His

```
<210> SEQ ID NO 3
<211> LENGTH: 563
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3
```

| | | | | | | | | | | | | | | |
|---|---|---|---|---|---|---|---|---|---|---|---|---|---|---|
| Gln | Val | Gln | Leu | Gln | Gln | Ser | Gly | Ala | Glu | Leu | Ala | Arg | Pro | Gly | Ala |
| 1 | | | | 5 | | | | | 10 | | | | | 15 | |
| Ser | Val | Lys | Met | Ser | Cys | Lys | Ala | Ser | Gly | Tyr | Thr | Phe | Thr | Arg | Tyr |
| | | 20 | | | | | 25 | | | | | 30 | | | |
| Thr | Met | His | Trp | Val | Lys | Gln | Arg | Pro | Gly | Gln | Gly | Leu | Glu | Trp | Ile |
| | | | 35 | | | | | 40 | | | | | 45 | | |
| Gly | Tyr | Ile | Asn | Pro | Ser | Arg | Gly | Tyr | Thr | Asn | Tyr | Asn | Gln | Lys | Phe |
| 50 | | | | | 55 | | | | | 60 | | | | | |
| Lys | Asp | Lys | Ala | Thr | Leu | Thr | Thr | Asp | Lys | Ser | Ser | Ser | Thr | Ala | Tyr |
| 65 | | | | | 70 | | | | | 75 | | | | | 80 |
| Met | Gln | Leu | Ser | Ser | Leu | Thr | Ser | Glu | Asp | Ser | Ala | Val | Tyr | Tyr | Cys |
| | | | | 85 | | | | | 90 | | | | | 95 | |
| Ala | Arg | Tyr | Tyr | Asp | Asp | His | Tyr | Ser | Leu | Asp | Tyr | Trp | Gly | Gln | Gly |
| | | | 100 | | | | | 105 | | | | | 110 | | |
| Thr | Thr | Leu | Thr | Val | Ser | Ser | Gly | Gly | Gly | Ser | Gly | Gly | Gly | Gly |
| | | 115 | | | | | 120 | | | | | 125 | | | |
| Ser | Gly | Gly | Gly | Gly | Ser | Gln | Ile | Val | Leu | Thr | Gln | Ser | Pro | Ala | Ile |
| 130 | | | | | 135 | | | | | 140 | | | | | |
| Met | Ser | Ala | Ser | Pro | Gly | Glu | Lys | Val | Thr | Met | Thr | Cys | Ser | Ala | Ser |
| 145 | | | | | 150 | | | | | 155 | | | | | 160 |
| Ser | Ser | Val | Ser | Tyr | Met | Asn | Trp | Tyr | Gln | Gln | Lys | Ser | Gly | Thr | Ser |
| | | | | 165 | | | | | 170 | | | | | 175 | |
| Pro | Lys | Arg | Trp | Ile | Tyr | Asp | Thr | Ser | Lys | Leu | Ala | Ser | Gly | Val | Pro |
| | | | 180 | | | | | 185 | | | | | 190 | | |
| Ala | His | Phe | Arg | Gly | Ser | Gly | Ser | Gly | Thr | Ser | Tyr | Ser | Leu | Thr | Ile |
| | | 195 | | | | | 200 | | | | | 205 | | | |
| Ser | Gly | Met | Glu | Ala | Glu | Asp | Ala | Ala | Thr | Tyr | Tyr | Cys | Gln | Gln | Trp |
| 210 | | | | | 215 | | | | | 220 | | | | | |
| Ser | Ser | Asn | Pro | Phe | Thr | Phe | Gly | Ser | Gly | Thr | Lys | Leu | Glu | Ile | Lys |
| 225 | | | | | 230 | | | | | 235 | | | | | 240 |
| Gly | Ser | Gly | Ser | Lys | Val | Ser | Val | Phe | Val | Pro | Pro | Arg | Asp | Gly | Phe |
| | | | | 245 | | | | | 250 | | | | | 255 | |
| Phe | Gly | Asn | Pro | Arg | Lys | Ser | Lys | Leu | Ile | Cys | Gln | Ala | Thr | Gly | Phe |
| | | | 260 | | | | | 265 | | | | | 270 | | |
| Ser | Pro | Arg | Gln | Ile | Gln | Val | Ser | Trp | Leu | Arg | Glu | Gly | Lys | Gln | Val |
| | | 275 | | | | | 280 | | | | | 285 | | | |
| Gly | Ser | Gly | Val | Thr | Thr | Asp | Gln | Val | Gln | Ala | Glu | Ala | Lys | Glu | Ser |
| 290 | | | | | 295 | | | | | 300 | | | | | |
| Gly | Pro | Thr | Thr | Tyr | Lys | Val | Thr | Ser | Thr | Leu | Thr | Ile | Lys | Glu | Ser |
| 305 | | | | | 310 | | | | | 315 | | | | | 320 |
| Asp | Trp | Leu | Ser | Gln | Ser | Met | Phe | Thr | Cys | Arg | Val | Asp | His | Arg | Gly |
| | | | | 325 | | | | | 330 | | | | | 335 | |
| Leu | Thr | Phe | Gln | Gln | Asn | Ala | Ser | Ser | Met | Cys | Val | Pro | Asp | Gln | Asp |
| | | | 340 | | | | | 345 | | | | | 350 | | |

```
Thr Ala Ile Arg Val Phe Ala Ile Pro Pro Ser Phe Ala Ser Ile Phe
            355                 360                 365

Leu Thr Lys Ser Thr Lys Leu Thr Cys Leu Val Thr Asp Leu Thr Thr
        370                 375                 380

Tyr Asp Ser Val Thr Ile Ser Trp Thr Arg Gln Asn Gly Glu Ala Val
385                 390                 395                 400

Lys Thr His Thr Asn Ile Ser Glu Ser His Pro Asn Ala Thr Phe Ser
                405                 410                 415

Ala Val Gly Glu Ala Ser Ile Ser Glu Asp Asp Trp Asn Ser Gly Glu
            420                 425                 430

Arg Phe Thr Cys Thr Val Thr His Thr Asp Leu Pro Ser Pro Leu Lys
        435                 440                 445

Gln Thr Ile Ser Arg Pro Lys Gly Val Ala Leu His Arg Pro Asp Val
    450                 455                 460

Tyr Leu Leu Pro Pro Ala Arg Glu Gln Leu Asn Leu Arg Glu Ser Ala
465                 470                 475                 480

Thr Ile Thr Cys Leu Val Thr Gly Phe Ser Pro Ala Asp Val Phe Val
                485                 490                 495

Gln Trp Met Gln Arg Gly Gln Pro Leu Ser Pro Glu Lys Tyr Val Thr
            500                 505                 510

Ser Ala Pro Met Pro Glu Pro Gln Ala Pro Gly Arg Tyr Phe Ala His
        515                 520                 525

Ser Ile Leu Thr Val Ser Glu Glu Trp Asn Thr Gly Glu Thr Tyr
    530                 535                 540

Thr Cys Val Val Ala His Glu Ala Leu Pro Asn Arg Val Thr Glu Arg
545                 550                 555                 560

Thr Val Asp

<210> SEQ ID NO 4
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140
```

```
Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
                195                 200                 205

Asn Arg Gly Glu Cys
            210

<210> SEQ ID NO 5
<211> LENGTH: 328
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gly Ser Gly Ser Lys Val Ser Val Phe Val Pro Pro Arg Asp Gly Phe
1               5                   10                  15

Phe Gly Asn Pro Arg Lys Ser Lys Leu Ile Cys Gln Ala Thr Gly Phe
                20                  25                  30

Ser Pro Arg Gln Ile Gln Val Ser Trp Leu Arg Glu Gly Lys Gln Val
            35                  40                  45

Gly Ser Gly Val Thr Thr Asp Gln Val Gln Ala Glu Ala Lys Glu Ser
50                  55                  60

Gly Pro Thr Thr Tyr Lys Val Thr Ser Thr Leu Thr Ile Lys Glu Ser
65                  70                  75                  80

Asp Trp Leu Ser Gln Ser Met Phe Thr Cys Arg Val Asp His Arg Gly
                85                  90                  95

Leu Thr Phe Gln Gln Asn Ala Ser Ser Met Cys Val Pro Asp Gln Asp
            100                 105                 110

Thr Ala Ile Arg Val Phe Ala Ile Pro Pro Ser Phe Ala Ser Ile Phe
            115                 120                 125

Leu Thr Lys Ser Thr Lys Leu Thr Cys Leu Val Thr Asp Leu Thr Thr
130                 135                 140

Tyr Asp Ser Val Thr Ile Ser Trp Thr Arg Gln Asn Gly Glu Ala Val
145                 150                 155                 160

Lys Thr His Thr Asn Ile Ser Glu Ser His Pro Asn Ala Thr Phe Ser
                165                 170                 175

Ala Val Gly Glu Ala Ser Ile Ser Glu Asp Asp Trp Asn Ser Gly Glu
            180                 185                 190

Arg Phe Thr Cys Thr Val Thr His Thr Asp Leu Pro Ser Pro Leu Lys
            195                 200                 205

Gln Thr Ile Ser Arg Pro Lys Gly Val Ala Leu His Arg Pro Asp Val
            210                 215                 220

Tyr Leu Leu Pro Pro Ala Arg Glu Gln Leu Asn Leu Arg Glu Ser Ala
225                 230                 235                 240

Thr Ile Tyr Cys Leu Val Thr Gly Phe Ser Pro Ala Asp Val Phe Val
                245                 250                 255

Gln Trp Met Gln Arg Gly Gln Pro Leu Ser Pro Glu Lys Tyr Val Thr
            260                 265                 270

Ser Ala Pro Met Pro Glu Pro Gln Ala Pro Gly Arg Tyr Phe Ala His
```

```
            275                 280                 285
Ser Ile Leu Thr Val Ser Glu Glu Trp Asn Thr Gly Glu Thr Tyr
        290                 295                 300

Thr Cys Val Val Ala His Glu Ala Leu Pro Asn Arg Val Thr Glu Arg
305                 310                 315                 320

Thr Val Asp Lys Ser Thr Gly Lys
                325

<210> SEQ ID NO 6
<211> LENGTH: 328
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gly Ser Gly Ser Lys Val Ser Val Phe Val Pro Pro Arg Asp Gly Phe
1               5                   10                  15

Phe Gly Asn Pro Arg Lys Ser Lys Leu Ile Cys Gln Ala Thr Gly Phe
            20                  25                  30

Ser Pro Arg Gln Ile Gln Val Ser Trp Leu Arg Glu Gly Lys Gln Val
        35                  40                  45

Gly Ser Gly Val Thr Thr Asp Gln Val Gln Ala Glu Ala Lys Glu Ser
    50                  55                  60

Gly Pro Thr Thr Tyr Lys Val Thr Ser Thr Leu Thr Ile Lys Glu Ser
65                  70                  75                  80

Asp Trp Leu Ser Gln Ser Met Phe Thr Cys Arg Val Asp His Arg Gly
                85                  90                  95

Leu Thr Phe Gln Gln Asn Ala Ser Ser Met Cys Val Pro Asp Gln Asp
            100                 105                 110

Thr Ala Ile Arg Val Phe Ala Ile Pro Pro Ser Phe Ala Ser Ile Phe
        115                 120                 125

Leu Thr Lys Ser Thr Lys Leu Thr Cys Leu Val Thr Asp Leu Thr Thr
    130                 135                 140

Tyr Asp Ser Val Thr Ile Ser Trp Thr Arg Gln Asn Gly Glu Ala Val
145                 150                 155                 160

Lys Thr His Thr Asn Ile Ser Glu Ser His Pro Asn Ala Thr Phe Ser
                165                 170                 175

Ala Val Gly Glu Ala Ser Ile Ser Glu Asp Asp Trp Asn Ser Gly Glu
            180                 185                 190

Arg Phe Thr Cys Thr Val Thr His Thr Asp Leu Pro Ser Pro Leu Lys
        195                 200                 205

Gln Thr Ile Ser Arg Pro Lys Gly Val Ala Leu His Arg Pro Asp Val
    210                 215                 220

Tyr Leu Leu Pro Pro Ala Arg Glu Gln Leu Asn Leu Arg Glu Ser Ala
225                 230                 235                 240

Thr Ile Thr Cys Ser Val Thr Gly Phe Ser Pro Ala Asp Val Phe Val
                245                 250                 255

Gln Trp Met Gln Arg Gly Gln Pro Leu Ser Pro Glu Lys Tyr Val Thr
            260                 265                 270

Ser Ala Pro Met Pro Glu Pro Gln Ala Pro Gly Arg Tyr Phe Ala Val
        275                 280                 285

Ser Ile Leu Thr Val Ser Glu Glu Glu Trp Asn Thr Gly Glu Thr Tyr
    290                 295                 300
```

```
Thr Cys Val Val Ala His Glu Ala Leu Pro Asn Arg Val Thr Glu Arg
305                 310                 315                 320

Thr Val Asp Lys Ser Thr Gly Lys
                325
```

<210> SEQ ID NO 7
<211> LENGTH: 328
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

```
Gly Ser Gly Ser Lys Val Ser Val Phe Val Pro Arg Asp Gly Phe
1               5                   10                  15

Phe Gly Asn Pro Arg Lys Ser Lys Leu Ile Cys Gln Ala Thr Gly Phe
                20                  25                  30

Ser Pro Arg Gln Ile Gln Val Ser Trp Leu Arg Glu Gly Lys Gln Val
            35                  40                  45

Gly Ser Gly Val Thr Thr Asp Gln Val Gln Ala Glu Ala Lys Glu Ser
    50                  55                  60

Gly Pro Thr Thr Tyr Lys Val Thr Ser Thr Leu Thr Ile Lys Glu Ser
65                  70                  75                  80

Asp Trp Leu Ser Gln Ser Met Phe Thr Cys Arg Val Asp His Arg Gly
                85                  90                  95

Leu Thr Phe Gln Gln Asn Ala Ser Ser Met Cys Val Pro Asp Gln Asp
            100                 105                 110

Thr Ala Ile Arg Val Phe Ala Ile Pro Pro Ser Phe Ala Ser Ile Phe
        115                 120                 125

Leu Thr Lys Ser Thr Lys Leu Thr Cys Leu Val Thr Asp Leu Thr Thr
    130                 135                 140

Tyr Asp Ser Val Thr Ile Ser Trp Thr Arg Gln Asn Gly Glu Ala Val
145                 150                 155                 160

Lys Thr His Thr Asn Ile Ser Glu Ser His Pro Asn Ala Thr Phe Ser
                165                 170                 175

Ala Val Gly Glu Ala Ser Ile Ser Glu Asp Asp Trp Asn Ser Gly Glu
            180                 185                 190

Arg Phe Thr Cys Thr Val Thr His Thr Asp Leu Pro Ser Pro Leu Lys
        195                 200                 205

Gln Thr Ile Ser Arg Pro Lys Gly Val Ala Leu His Arg Pro Asp Val
    210                 215                 220

Tyr Leu Leu Pro Pro Ala Arg Glu Gln Leu Asn Leu Arg Glu Ser Ala
225                 230                 235                 240

Thr Ile Tyr Cys Leu Val Glu Gly Phe Ser Pro Ala Asp Val Phe Val
                245                 250                 255

Gln Trp Met Gln Arg Gly Gln Pro Leu Ser Pro Glu Lys Tyr Val Thr
            260                 265                 270

Ser Ala Pro Met Pro Glu Pro Gln Ala Pro Gly Arg Tyr Phe Ala His
        275                 280                 285

Ser Glu Leu Thr Val Ser Glu Glu Glu Trp Asn Thr Gly Glu Thr Tyr
    290                 295                 300

Thr Cys Val Val Ala His Glu Ala Leu Pro Asn Arg Val Thr Glu Arg
305                 310                 315                 320

Thr Val Asp Lys Ser Thr Gly Lys
                325
```

<210> SEQ ID NO 8
<211> LENGTH: 328
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 8

```
Gly Ser Gly Ser Lys Val Ser Val Phe Val Pro Pro Arg Asp Gly Phe
1               5                   10                  15

Phe Gly Asn Pro Arg Lys Ser Lys Leu Ile Cys Gln Ala Thr Gly Phe
                20                  25                  30

Ser Pro Arg Gln Ile Gln Val Ser Trp Leu Arg Glu Gly Lys Gln Val
            35                  40                  45

Gly Ser Gly Val Thr Thr Asp Gln Val Gln Ala Glu Ala Lys Glu Ser
        50                  55                  60

Gly Pro Thr Thr Tyr Lys Val Thr Ser Thr Leu Thr Ile Lys Glu Ser
65                  70                  75                  80

Asp Trp Leu Ser Gln Ser Met Phe Thr Cys Arg Val Asp His Arg Gly
                85                  90                  95

Leu Thr Phe Gln Gln Asn Ala Ser Ser Met Cys Val Pro Asp Gln Asp
            100                 105                 110

Thr Ala Ile Arg Val Phe Ala Ile Pro Pro Ser Phe Ala Ser Ile Phe
        115                 120                 125

Leu Thr Lys Ser Thr Lys Leu Thr Cys Leu Val Thr Asp Leu Thr Thr
130                 135                 140

Tyr Asp Ser Val Thr Ile Ser Trp Thr Arg Gln Asn Gly Glu Ala Val
145                 150                 155                 160

Lys Thr His Thr Asn Ile Ser Glu Ser His Pro Asn Ala Thr Phe Ser
                165                 170                 175

Ala Val Gly Glu Ala Ser Ile Ser Glu Asp Asp Trp Asn Ser Gly Glu
            180                 185                 190

Arg Phe Thr Cys Thr Val Thr His Thr Asp Leu Pro Ser Pro Leu Lys
        195                 200                 205

Gln Thr Ile Ser Arg Pro Lys Gly Val Ala Leu His Arg Pro Asp Val
    210                 215                 220

Tyr Leu Leu Pro Pro Ala Arg Glu Gln Leu Asn Leu Arg Glu Ser Ala
225                 230                 235                 240

Thr Ile Thr Cys Ser Val Lys Gly Phe Ser Pro Ala Asp Val Phe Val
                245                 250                 255

Gln Trp Met Gln Arg Gly Gln Pro Leu Ser Pro Glu Lys Tyr Val Thr
            260                 265                 270

Ser Ala Pro Met Pro Glu Pro Gln Ala Pro Gly Arg Tyr Phe Ala Val
        275                 280                 285

Ser Lys Leu Thr Val Ser Glu Glu Glu Trp Asn Thr Gly Glu Thr Tyr
    290                 295                 300

Thr Cys Val Val Ala His Glu Ala Leu Pro Asn Arg Val Thr Glu Arg
305                 310                 315                 320

Thr Val Asp Lys Ser Thr Gly Lys
                325
```

<210> SEQ ID NO 9
<211> LENGTH: 556
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 9

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ser Gly Ser Ala Ser Ala Pro Thr
        115                 120                 125

Leu Phe Pro Leu Val Ser Cys Glu Asn Ser Pro Ser Asp Thr Ser Ser
    130                 135                 140

Val Ala Val Gly Cys Leu Ala Gln Asp Phe Leu Pro Asp Ser Ile Thr
145                 150                 155                 160

Phe Ser Trp Lys Tyr Lys Asn Asn Ser Asp Ile Ser Ser Thr Arg Gly
                165                 170                 175

Phe Pro Ser Val Leu Arg Gly Gly Lys Tyr Ala Ala Thr Ser Gln Val
            180                 185                 190

Leu Leu Pro Ser Lys Asp Val Met Gln Gly Thr Asp Glu His Val Val
        195                 200                 205

Cys Lys Val Gln His Pro Asn Gly Asn Lys Glu Lys Asn Val Pro Leu
    210                 215                 220

Pro Val Ile Ala Glu Leu Pro Pro Lys Val Ser Val Phe Val Pro Pro
225                 230                 235                 240

Arg Asp Gly Phe Phe Gly Asn Pro Arg Lys Ser Lys Leu Ile Cys Gln
                245                 250                 255

Ala Thr Gly Phe Ser Pro Arg Gln Ile Gln Val Ser Trp Leu Arg Glu
            260                 265                 270

Gly Lys Gln Val Gly Ser Gly Val Thr Thr Asp Gln Val Gln Ala Glu
        275                 280                 285

Ala Lys Glu Ser Gly Pro Thr Thr Tyr Lys Val Thr Ser Thr Leu Thr
    290                 295                 300

Ile Lys Glu Ser Asp Trp Leu Ser Gln Ser Met Phe Thr Cys Arg Val
305                 310                 315                 320

Asp His Arg Gly Leu Thr Phe Gln Gln Asn Ala Ser Ser Met Cys Val
                325                 330                 335

Pro Asp Gln Asp Thr Ala Ile Arg Val Phe Ala Ile Pro Pro Ser Phe
            340                 345                 350

Ala Ser Ile Phe Leu Thr Lys Ser Thr Lys Leu Thr Cys Leu Val Thr
        355                 360                 365

Asp Leu Thr Thr Tyr Asp Ser Val Thr Ile Ser Trp Thr Arg Gln Asn
    370                 375                 380

Gly Glu Ala Val Lys Thr His Thr Asn Ile Ser Glu Ser His Pro Asn
385                 390                 395                 400

Ala Thr Phe Ser Ala Val Gly Glu Ala Ser Ile Ser Glu Asp Asp Trp
                405                 410                 415

Asn Ser Gly Glu Arg Phe Thr Cys Thr Val Thr His Thr Asp Leu Pro
            420                 425                 430

Ser Pro Leu Lys Gln Thr Ile Ser Arg Pro Lys Gly Val Ala Leu His
        435                 440                 445

Arg Pro Asp Val Tyr Leu Leu Pro Pro Ala Arg Glu Gln Leu Asn Leu
450                 455                 460

Arg Glu Ser Ala Thr Ile Tyr Cys Leu Val Glu Gly Phe Ser Pro Ala
465                 470                 475                 480

Asp Val Phe Val Gln Trp Met Gln Arg Gly Gln Pro Leu Ser Pro Glu
                485                 490                 495

Lys Tyr Val Thr Ser Ala Pro Met Pro Glu Pro Gln Ala Pro Gly Arg
            500                 505                 510

Tyr Phe Ala His Ser Glu Leu Thr Val Ser Glu Glu Trp Asn Thr
        515                 520                 525

Gly Glu Thr Tyr Thr Cys Val Val Ala His Glu Ala Leu Pro Asn Arg
530                 535                 540

Val Thr Glu Arg Thr Val Asp Lys Ser Thr Gly Lys
545                 550                 555

<210> SEQ ID NO 10
<211> LENGTH: 556
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
                20                  25                  30

Asn Met His Trp Val Lys Gln Thr Pro Gly Arg Gly Leu Glu Trp Ile
            35                  40                  45

Gly Ala Ile Tyr Pro Gly Asn Gly Asp Thr Ser Tyr Asn Gln Lys Phe
        50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ser Gly Ser Ala Ser Ala Pro Thr
        115                 120                 125

Leu Phe Pro Leu Val Ser Cys Glu Asn Ser Pro Ser Asp Thr Ser Ser
130                 135                 140

Val Ala Val Gly Cys Leu Ala Gln Asp Phe Leu Pro Asp Ser Ile Thr
145                 150                 155                 160

Phe Ser Trp Lys Tyr Lys Asn Asn Ser Asp Ile Ser Ser Thr Arg Gly
                165                 170                 175

Phe Pro Ser Val Leu Arg Gly Gly Lys Tyr Ala Ala Thr Ser Gln Val
            180                 185                 190

```
Leu Leu Pro Ser Lys Asp Val Met Gln Gly Thr Asp Glu His Val Val
            195                 200                 205

Cys Lys Val Gln His Pro Asn Gly Asn Lys Glu Lys Asn Val Pro Leu
        210                 215                 220

Pro Val Ile Ala Glu Leu Pro Pro Lys Val Ser Val Phe Val Pro Pro
225                 230                 235                 240

Arg Asp Gly Phe Phe Gly Asn Pro Arg Lys Ser Lys Leu Ile Cys Gln
                245                 250                 255

Ala Thr Gly Phe Ser Pro Arg Gln Ile Gln Val Ser Trp Leu Arg Glu
                260                 265                 270

Gly Lys Gln Val Gly Ser Gly Val Thr Thr Asp Gln Val Gln Ala Glu
        275                 280                 285

Ala Lys Glu Ser Gly Pro Thr Thr Tyr Lys Val Thr Ser Thr Leu Thr
        290                 295                 300

Ile Lys Glu Ser Asp Trp Leu Ser Gln Ser Met Phe Thr Cys Arg Val
305                 310                 315                 320

Asp His Arg Gly Leu Thr Phe Gln Gln Asn Ala Ser Ser Met Cys Val
                325                 330                 335

Pro Asp Gln Asp Thr Ala Ile Arg Val Phe Ala Ile Pro Pro Ser Phe
            340                 345                 350

Ala Ser Ile Phe Leu Thr Lys Ser Thr Lys Leu Thr Cys Leu Val Thr
        355                 360                 365

Asp Leu Thr Thr Tyr Asp Ser Val Thr Ile Ser Trp Thr Arg Gln Asn
370                 375                 380

Gly Glu Ala Val Lys Thr His Thr Asn Ile Ser Glu Ser His Pro Asn
385                 390                 395                 400

Ala Thr Phe Ser Ala Val Gly Glu Ala Ser Ile Ser Glu Asp Asp Trp
                405                 410                 415

Asn Ser Gly Glu Arg Phe Thr Cys Thr Val Thr His Thr Asp Leu Pro
            420                 425                 430

Ser Pro Leu Lys Gln Thr Ile Ser Arg Pro Lys Gly Val Ala Leu His
        435                 440                 445

Arg Pro Asp Val Tyr Leu Leu Pro Pro Ala Arg Glu Gln Leu Asn Leu
    450                 455                 460

Arg Glu Ser Ala Thr Ile Thr Cys Ser Val Lys Gly Phe Ser Pro Ala
465                 470                 475                 480

Asp Val Phe Val Gln Trp Met Gln Arg Gly Gln Pro Leu Ser Pro Glu
                485                 490                 495

Lys Tyr Val Thr Ser Ala Pro Met Pro Glu Pro Gln Ala Pro Gly Arg
            500                 505                 510

Tyr Phe Ala Val Ser Lys Leu Thr Val Ser Glu Glu Glu Trp Asn Thr
        515                 520                 525

Gly Glu Thr Tyr Thr Cys Val Val Ala His Glu Ala Leu Pro Asn Arg
530                 535                 540

Val Thr Glu Arg Thr Val Asp Lys Ser Thr Gly Lys
545                 550                 555

<210> SEQ ID NO 11
<211> LENGTH: 568
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 11

```
Gln Val Gln Leu Gln Gln Ser Gly Ala Glu Leu Ala Arg Pro Gly Ala
1               5                   10                  15
Ser Val Lys Met Ser Cys Lys Ala Ser Gly Tyr Thr Phe Thr Arg Tyr
            20                  25                  30
Thr Met His Trp Val Lys Gln Arg Pro Gly Gln Gly Leu Glu Trp Ile
        35                  40                  45
Gly Tyr Ile Asn Pro Ser Arg Gly Tyr Thr Asn Tyr Asn Gln Lys Phe
    50                  55                  60
Lys Asp Lys Ala Thr Leu Thr Thr Asp Lys Ser Ser Ser Thr Ala Tyr
65                  70                  75                  80
Met Gln Leu Ser Ser Leu Thr Ser Glu Asp Ser Ala Val Tyr Tyr Cys
                85                  90                  95
Ala Arg Tyr Tyr Asp Asp His Tyr Ser Leu Asp Tyr Trp Gly Gln Gly
            100                 105                 110
Thr Thr Leu Thr Val Ser Ser Gly Gly Gly Ser Gly Gly Gly Gly
        115                 120                 125
Ser Gly Gly Gly Gly Ser Gln Ile Val Leu Thr Gln Ser Pro Ala Ile
    130                 135                 140
Met Ser Ala Ser Pro Gly Glu Lys Val Thr Met Thr Cys Ser Ala Ser
145                 150                 155                 160
Ser Ser Val Ser Tyr Met Asn Trp Tyr Gln Gln Lys Ser Gly Thr Ser
                165                 170                 175
Pro Lys Arg Trp Ile Tyr Asp Thr Ser Lys Leu Ala Ser Gly Val Pro
            180                 185                 190
Ala His Phe Arg Gly Ser Gly Ser Gly Thr Ser Tyr Ser Leu Thr Ile
        195                 200                 205
Ser Gly Met Glu Ala Glu Asp Ala Ala Thr Tyr Tyr Cys Gln Gln Trp
    210                 215                 220
Ser Ser Asn Pro Phe Thr Phe Gly Ser Gly Thr Lys Leu Glu Ile Lys
225                 230                 235                 240
Gly Ser Gly Ser Lys Val Ser Val Phe Val Pro Arg Asp Gly Phe
                245                 250                 255
Phe Gly Asn Pro Arg Lys Ser Lys Leu Ile Cys Gln Ala Thr Gly Phe
            260                 265                 270
Ser Pro Arg Gln Ile Gln Val Ser Trp Leu Arg Glu Gly Lys Gln Val
        275                 280                 285
Gly Ser Gly Val Thr Thr Asp Gln Val Gln Ala Glu Ala Lys Glu Ser
    290                 295                 300
Gly Pro Thr Thr Tyr Lys Val Thr Ser Thr Leu Thr Ile Lys Glu Ser
305                 310                 315                 320
Asp Trp Leu Ser Gln Ser Met Phe Thr Cys Arg Val Asp His Arg Gly
                325                 330                 335
Leu Thr Phe Gln Gln Asn Ala Ser Ser Met Cys Val Pro Asp Gln Asp
            340                 345                 350
Thr Ala Ile Arg Val Phe Ala Ile Pro Pro Ser Phe Ala Ser Ile Phe
        355                 360                 365
Leu Thr Lys Ser Thr Lys Leu Thr Cys Leu Val Thr Asp Leu Thr Thr
    370                 375                 380
Tyr Asp Ser Val Thr Ile Ser Trp Thr Arg Gln Asn Gly Glu Ala Val
385                 390                 395                 400
Lys Thr His Thr Asn Ile Ser Glu Ser His Pro Asn Ala Thr Phe Ser
                405                 410                 415
```

```
Ala Val Gly Glu Ala Ser Ile Ser Glu Asp Asp Trp Asn Ser Gly Glu
            420                 425                 430

Arg Phe Thr Cys Thr Val Thr His Thr Asp Leu Pro Ser Pro Leu Lys
            435                 440                 445

Gln Thr Ile Ser Arg Pro Lys Gly Val Ala Leu His Arg Pro Asp Val
            450                 455                 460

Tyr Leu Leu Pro Pro Ala Arg Glu Gln Leu Asn Leu Arg Glu Ser Ala
465                 470                 475                 480

Thr Ile Tyr Cys Leu Val Glu Gly Phe Ser Pro Ala Asp Val Phe Val
            485                 490                 495

Gln Trp Met Gln Arg Gly Gln Pro Leu Ser Pro Glu Lys Tyr Val Thr
            500                 505                 510

Ser Ala Pro Met Pro Glu Pro Gln Ala Pro Gly Arg Tyr Phe Ala His
            515                 520                 525

Ser Glu Leu Thr Val Ser Glu Glu Trp Asn Thr Gly Glu Thr Tyr
            530                 535                 540

Thr Cys Val Val Ala His Glu Ala Leu Pro Asn Arg Val Thr Glu Arg
545                 550                 555                 560

Thr Val Asp Lys Ser Thr Gly Lys
            565

<210> SEQ ID NO 12
<211> LENGTH: 568
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
            85                  90                  95

Ala Arg Tyr Tyr Asp Asp His Tyr Ser Leu Asp Tyr Trp Gly Gln Gly
            100                 105                 110

Thr Thr Leu Thr Val Ser Ser Gly Gly Gly Ser Gly Gly Gly Gly
        115                 120                 125

Ser Gly Gly Gly Gly Ser Gln Ile Val Leu Thr Gln Ser Pro Ala Ile
    130                 135                 140

Met Ser Ala Ser Pro Gly Glu Lys Val Thr Met Thr Cys Ser Ala Ser
145                 150                 155                 160

Ser Ser Val Ser Tyr Met Asn Trp Tyr Gln Gln Lys Ser Gly Thr Ser
            165                 170                 175

Pro Lys Arg Trp Ile Tyr Asp Thr Ser Lys Leu Ala Ser Gly Val Pro
        180                 185                 190

Ala His Phe Arg Gly Ser Gly Ser Gly Thr Ser Tyr Ser Leu Thr Ile
```

```
            195                 200                 205
Ser Gly Met Glu Ala Glu Asp Ala Ala Thr Tyr Tyr Cys Gln Gln Trp
210                 215                 220

Ser Ser Asn Pro Phe Thr Phe Gly Ser Gly Thr Lys Leu Glu Ile Lys
225                 230                 235                 240

Gly Ser Gly Ser Lys Val Ser Val Phe Val Pro Pro Arg Asp Gly Phe
                245                 250                 255

Phe Gly Asn Pro Arg Lys Ser Lys Leu Ile Cys Gln Ala Thr Gly Phe
            260                 265                 270

Ser Pro Arg Gln Ile Gln Val Ser Trp Leu Arg Glu Gly Lys Gln Val
        275                 280                 285

Gly Ser Gly Val Thr Thr Asp Gln Val Gln Ala Glu Ala Lys Glu Ser
290                 295                 300

Gly Pro Thr Thr Tyr Lys Val Thr Ser Thr Leu Thr Ile Lys Glu Ser
305                 310                 315                 320

Asp Trp Leu Ser Gln Ser Met Phe Thr Cys Arg Val Asp His Arg Gly
                325                 330                 335

Leu Thr Phe Gln Gln Asn Ala Ser Ser Met Cys Val Pro Asp Gln Asp
            340                 345                 350

Thr Ala Ile Arg Val Phe Ala Ile Pro Pro Ser Phe Ala Ser Ile Phe
        355                 360                 365

Leu Thr Lys Ser Thr Lys Leu Thr Cys Leu Val Thr Asp Leu Thr Thr
370                 375                 380

Tyr Asp Ser Val Thr Ile Ser Trp Thr Arg Gln Asn Gly Glu Ala Val
385                 390                 395                 400

Lys Thr His Thr Asn Ile Ser Glu Ser His Pro Asn Ala Thr Phe Ser
                405                 410                 415

Ala Val Gly Glu Ala Ser Ile Ser Glu Asp Asp Trp Asn Ser Gly Glu
            420                 425                 430

Arg Phe Thr Cys Thr Val Thr His Thr Asp Leu Pro Ser Pro Leu Lys
        435                 440                 445

Gln Thr Ile Ser Arg Pro Lys Gly Val Ala Leu His Arg Pro Asp Val
    450                 455                 460

Tyr Leu Leu Pro Pro Ala Arg Glu Gln Leu Asn Leu Arg Glu Ser Ala
465                 470                 475                 480

Thr Ile Thr Cys Ser Val Lys Gly Phe Ser Pro Ala Asp Val Phe Val
                485                 490                 495

Gln Trp Met Gln Arg Gly Gln Pro Leu Ser Pro Glu Lys Tyr Val Thr
            500                 505                 510

Ser Ala Pro Met Pro Glu Pro Gln Ala Pro Gly Arg Tyr Phe Ala Val
        515                 520                 525

Ser Lys Leu Thr Val Ser Glu Glu Trp Asn Thr Gly Glu Thr Tyr Thr
    530                 535                 540

Thr Cys Val Val Ala His Glu Ala Leu Pro Asn Arg Val Thr Glu Arg
545                 550                 555                 560

Thr Val Asp Lys Ser Thr Gly Lys
                565
```

<210> SEQ ID NO 13
<211> LENGTH: 572
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Gly Ser Ala Ser Ala Pro Thr Leu Phe
        115                 120                 125

Pro Leu Val Ser Cys Glu Asn Ser Pro Ser Asp Thr Ser Ser Val Ala
    130                 135                 140

Val Gly Cys Leu Ala Gln Asp Phe Leu Pro Asp Ser Ile Thr Phe Ser
145                 150                 155                 160

Trp Lys Tyr Lys Asn Asn Ser Asp Ile Ser Ser Thr Arg Gly Phe Pro
                165                 170                 175

Ser Val Leu Arg Gly Gly Lys Tyr Ala Ala Thr Ser Gln Val Leu Leu
            180                 185                 190

Pro Ser Lys Asp Val Met Gln Gly Thr Asp Glu His Val Val Cys Lys
        195                 200                 205

Val Gln His Pro Asn Gly Asn Lys Glu Lys Asn Val Pro Leu Pro Val
    210                 215                 220

Ile Ala Glu Leu Pro Pro Lys Val Ser Val Phe Val Pro Pro Arg Asp
225                 230                 235                 240

Gly Phe Phe Gly Asn Pro Arg Lys Ser Lys Leu Ile Cys Gln Ala Thr
                245                 250                 255

Gly Phe Ser Pro Arg Gln Ile Gln Val Ser Trp Leu Arg Glu Gly Lys
            260                 265                 270

Gln Val Gly Ser Gly Val Thr Thr Asp Gln Val Gln Ala Glu Ala Lys
        275                 280                 285

Glu Ser Gly Pro Thr Thr Tyr Lys Val Thr Ser Thr Leu Thr Ile Lys
    290                 295                 300

Glu Ser Asp Trp Leu Ser Gln Ser Met Phe Thr Cys Arg Val Asp His
305                 310                 315                 320

Arg Gly Leu Thr Phe Gln Gln Asn Ala Ser Ser Met Cys Val Pro Asp
                325                 330                 335

Gln Asp Thr Ala Ile Arg Val Phe Ala Ile Pro Pro Ser Phe Ala Ser
            340                 345                 350

Ile Phe Leu Thr Lys Ser Thr Lys Leu Thr Cys Leu Val Thr Asp Leu
        355                 360                 365

Thr Thr Tyr Asp Ser Val Thr Ile Ser Trp Thr Arg Gln Asn Gly Glu
    370                 375                 380

Ala Val Lys Thr His Thr Asn Ile Ser Glu Ser His Pro Asn Ala Thr
385                 390                 395                 400

Phe Ser Ala Val Gly Glu Ala Ser Ile Cys Glu Asp Asp Trp Asn Ser
```

```
            405                 410                 415
Gly Glu Arg Phe Thr Cys Thr Val Thr His Thr Asp Leu Pro Ser Pro
            420                 425                 430

Leu Lys Gln Thr Ile Ser Arg Pro Lys Gly Val Ala Leu His Arg Pro
        435                 440                 445

Asp Val Tyr Leu Leu Pro Pro Ala Arg Glu Gln Leu Asn Leu Arg Glu
    450                 455                 460

Ser Ala Thr Ile Thr Cys Leu Val Thr Gly Phe Ser Pro Ala Asp Val
465                 470                 475                 480

Phe Val Gln Trp Met Gln Arg Gly Gln Pro Leu Ser Pro Glu Lys Tyr
                485                 490                 495

Val Thr Ser Ala Pro Met Pro Glu Pro Gln Ala Pro Gly Arg Tyr Phe
                500                 505                 510

Ala His Ser Ile Leu Thr Val Ser Glu Glu Trp Asn Thr Gly Glu
                515                 520                 525

Thr Tyr Thr Cys Val Val Ala His Glu Ala Leu Pro Asn Arg Val Thr
            530                 535                 540

Glu Arg Thr Val Asp Lys Ser Thr Gly Lys Pro Thr Leu Tyr Asn Val
545                 550                 555                 560

Ser Leu Val Met Ser Asp Thr Ala Gly Thr Cys Tyr
                565                 570
```

<210> SEQ ID NO 14
<211> LENGTH: 372
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 14

```
Gln Val Gln Leu Gly Gly Pro Glu Gln Lys Leu Ile Ser Glu Glu Asp
1               5                   10                  15

Leu Asn Ser Ala Val Leu Pro Val Ile Ala Glu Leu Pro Pro Lys Val
            20                  25                  30

Ser Val Phe Val Pro Pro Arg Asp Gly Phe Gly Asn Pro Arg Lys
        35                  40                  45

Ser Lys Leu Ile Cys Gln Ala Thr Gly Phe Ser Pro Arg Gln Ile Gln
    50                  55                  60

Val Ser Trp Leu Arg Glu Gly Lys Gln Val Gly Ser Gly Val Thr Thr
65                  70                  75                  80

Asp Gln Val Gln Ala Glu Ala Lys Glu Ser Gly Pro Thr Thr Tyr Lys
                85                  90                  95

Val Thr Ser Thr Leu Thr Ile Lys Glu Ser Asp Trp Leu Ser Gln Ser
            100                 105                 110

Met Phe Thr Cys Arg Val Asp His Arg Gly Leu Thr Phe Gln Gln Asn
        115                 120                 125

Ala Ser Ser Met Cys Val Pro Asp Gln Asp Thr Ala Ile Arg Val Phe
    130                 135                 140

Ala Ile Pro Pro Ser Phe Ala Ser Ile Phe Leu Thr Lys Ser Thr Lys
145                 150                 155                 160

Leu Thr Cys Leu Val Thr Asp Leu Thr Thr Tyr Asp Ser Val Thr Ile
                165                 170                 175

Ser Trp Thr Arg Gln Asn Gly Glu Ala Val Lys Thr His Thr Asn Ile
            180                 185                 190
```

```
Ser Glu Ser His Pro Asn Ala Thr Phe Ser Ala Val Gly Glu Ala Ser
            195                 200                 205

Ile Cys Glu Asp Asp Trp Asn Ser Gly Glu Arg Phe Thr Cys Thr Val
    210                 215                 220

Thr His Thr Asp Leu Pro Ser Pro Leu Lys Gln Thr Ile Ser Arg Pro
225                 230                 235                 240

Lys Gly Val Ala Leu His Arg Pro Asp Val Tyr Leu Leu Pro Pro Ala
                245                 250                 255

Arg Glu Gln Leu Asn Leu Arg Glu Ser Ala Thr Ile Thr Cys Leu Val
            260                 265                 270

Thr Gly Phe Ser Pro Ala Asp Val Phe Val Gln Trp Met Gln Arg Gly
        275                 280                 285

Gln Pro Leu Ser Pro Glu Lys Tyr Val Thr Ser Ala Pro Met Pro Glu
    290                 295                 300

Pro Gln Ala Pro Gly Arg Tyr Phe Ala His Ser Ile Leu Thr Val Ser
305                 310                 315                 320

Glu Glu Glu Trp Asn Thr Gly Glu Thr Tyr Thr Cys Val Val Ala His
                325                 330                 335

Glu Ala Leu Pro Asn Arg Val Thr Glu Arg Thr Val Asp Lys Ser Thr
            340                 345                 350

Gly Lys Pro Thr Leu Tyr Asn Val Ser Leu Val Met Ser Asp Thr Ala
        355                 360                 365

Gly Thr Cys Tyr
    370

<210> SEQ ID NO 15
<211> LENGTH: 582
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ser Val Ala Ala Pro Ser Val
        115                 120                 125

Phe Ile Phe Pro Pro Ser Asp Glu Gln Leu Lys Ser Gly Thr Ala Ser
    130                 135                 140

Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Gln Glu Ser Val
                165                 170                 175
```

```
Thr Glu Gln Asp Ser Lys Asp Ser Thr Tyr Ser Leu Ser Ser Thr Leu
            180                 185                 190

Thr Leu Ser Lys Ala Asp Tyr Glu Lys His Lys Val Tyr Ala Cys Glu
        195                 200                 205

Val Thr His Gln Gly Leu Ser Ser Pro Val Thr Lys Ser Phe Asn Arg
    210                 215                 220

Gly Glu Cys Asp Lys Thr His Leu Pro Val Ile Ala Glu Leu Pro Pro
225                 230                 235                 240

Lys Val Ser Val Phe Val Pro Pro Arg Asp Gly Phe Phe Gly Asn Pro
                245                 250                 255

Arg Lys Ser Lys Leu Ile Cys Gln Ala Thr Gly Phe Ser Pro Arg Gln
            260                 265                 270

Ile Gln Val Ser Trp Leu Arg Glu Gly Lys Gln Val Gly Ser Gly Val
        275                 280                 285

Thr Thr Asp Gln Val Gln Ala Glu Ala Lys Glu Ser Gly Pro Thr Thr
    290                 295                 300

Tyr Lys Val Thr Ser Thr Leu Thr Ile Lys Glu Ser Asp Trp Leu Ser
305                 310                 315                 320

Gln Ser Met Phe Thr Cys Arg Val Asp His Arg Gly Leu Thr Phe Gln
                325                 330                 335

Gln Asn Ala Ser Ser Met Cys Val Pro Asp Gln Asp Thr Ala Ile Arg
            340                 345                 350

Val Phe Ala Ile Pro Pro Ser Phe Ala Ser Ile Phe Leu Thr Lys Ser
        355                 360                 365

Thr Lys Leu Thr Cys Leu Val Thr Asp Leu Thr Thr Tyr Asp Ser Val
    370                 375                 380

Thr Ile Ser Trp Thr Arg Gln Asn Gly Glu Ala Val Lys Thr His Thr
385                 390                 395                 400

Asn Ile Ser Glu Ser His Pro Asn Ala Thr Phe Ser Ala Val Gly Glu
                405                 410                 415

Ala Ser Ile Cys Glu Asp Asp Trp Asn Ser Gly Glu Arg Phe Thr Cys
            420                 425                 430

Thr Val Thr His Thr Asp Leu Pro Ser Pro Leu Lys Gln Thr Ile Ser
        435                 440                 445

Arg Pro Lys Gly Val Ala Leu His Arg Pro Asp Val Tyr Leu Leu Pro
    450                 455                 460

Pro Ala Arg Glu Gln Leu Asn Leu Arg Glu Ser Ala Thr Ile Thr Cys
465                 470                 475                 480

Leu Val Thr Gly Phe Ser Pro Ala Asp Val Phe Val Gln Trp Met Gln
                485                 490                 495

Arg Gly Gln Pro Leu Ser Pro Glu Lys Tyr Val Thr Ser Ala Pro Met
            500                 505                 510

Pro Glu Pro Gln Ala Pro Gly Arg Tyr Phe Ala His Ser Ile Leu Thr
        515                 520                 525

Val Ser Glu Glu Glu Trp Asn Thr Gly Glu Thr Tyr Thr Cys Val Val
    530                 535                 540

Ala His Glu Ala Leu Pro Asn Arg Val Thr Glu Arg Thr Val Asp Lys
545                 550                 555                 560

Ser Thr Gly Lys Pro Thr Leu Tyr Asn Val Ser Leu Val Met Ser Asp
                565                 570                 575

Thr Ala Gly Thr Cys Tyr
            580
```

<210> SEQ ID NO 16
<211> LENGTH: 213
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 16

```
Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

Asn Trp Tyr Gln Gln Lys Ser Gly Thr Ser Pro Lys Arg Trp Ile Tyr
            35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn Arg Ala Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 17
<211> LENGTH: 211
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 17

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Val Ser Tyr Ile
            20                  25                  30

His Trp Phe Gln Gln Lys Pro Gly Ser Ser Pro Lys Pro Trp Ile Tyr
            35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80
```

```
Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Ser Ser Ala Ser Thr Lys
            100                 105                 110

Gly Pro Ser Val Phe Pro Leu Ala Pro Ser Ser Lys Ser Thr Ser Gly
        115                 120                 125

Gly Thr Ala Ala Leu Gly Cys Leu Val Lys Asp Tyr Phe Pro Glu Pro
    130                 135                 140

Val Thr Val Ser Trp Asn Ser Gly Ala Leu Thr Ser Gly Val His Thr
145                 150                 155                 160

Phe Pro Ala Val Leu Gln Ser Ser Gly Leu Tyr Ser Leu Ser Ser Val
                165                 170                 175

Val Thr Val Pro Ser Ser Ser Leu Gly Thr Gln Thr Tyr Ile Cys Asn
            180                 185                 190

Val Asn His Lys Pro Ser Asn Thr Lys Val Asp Lys Arg Val Glu Pro
        195                 200                 205

Lys Ser Cys
    210

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 18

His His His His His His
1               5

<210> SEQ ID NO 19
<211> LENGTH: 103
<212> TYPE: PRT
<213> ORGANISM: Homo sapiens

<400> SEQUENCE: 19

Ala Ser Thr Gln Ser Pro Ser Val Phe Pro Leu Thr Arg Cys Cys Lys
1               5                   10                  15

Asn Ile Pro Ser Asn Ala Thr Ser Val Thr Leu Gly Cys Leu Ala Thr
            20                  25                  30

Gly Tyr Phe Pro Glu Pro Val Met Val Thr Cys Asp Thr Gly Ser Leu
        35                  40                  45

Asn Gly Thr Thr Met Thr Leu Pro Ala Thr Thr Leu Thr Leu Ser Gly
    50                  55                  60

His Tyr Ala Thr Ile Ser Leu Leu Thr Val Ser Gly Ala Trp Ala Lys
65                  70                  75                  80

Gln Met Phe Thr Cys Arg Val Ala His Thr Pro Ser Ser Thr Asp Trp
                85                  90                  95

Val Asp Asn Lys Thr Phe Ser
            100

<210> SEQ ID NO 20
<211> LENGTH: 98
<212> TYPE: PRT
<213> ORGANISM: Homo sapiens

<400> SEQUENCE: 20

Ala Ser Thr Lys Gly Pro Ser Val Phe Pro Leu Ala Pro Ser Ser Lys
```

-continued

```
                1               5                  10                 15
Ser Thr Ser Gly Gly Thr Ala Ala Leu Gly Cys Leu Val Lys Asp Tyr
                20                 25                 30

Phe Pro Glu Pro Val Thr Val Ser Trp Asn Ser Gly Ala Leu Thr Ser
                35                 40                 45

Gly Val His Thr Phe Pro Ala Val Leu Gln Ser Ser Gly Leu Tyr Ser
                50                 55                 60

Leu Ser Ser Val Val Thr Val Pro Ser Ser Leu Gly Thr Gln Thr
65                 70                 75                 80

Tyr Ile Cys Asn Val Asn His Lys Pro Ser Asn Thr Lys Val Asp Lys
                85                 90                 95

Lys Val
```

<210> SEQ ID NO 21
<211> LENGTH: 104
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Ala or Leu
<220> FEATURE:
<221> NAME/KEY: MOD_RES
<222> LOCATION: (65)..(65)
<223> OTHER INFORMATION: Tyr or His

<400> SEQUENCE: 21

```
Gly Ser Xaa Ser Ala Pro Thr Leu Phe Pro Leu Val Ser Cys Glu Asn
1               5                  10                 15

Ser Pro Ser Asp Thr Ser Ser Val Ala Val Gly Cys Leu Ala Gln Asp
                20                 25                 30

Phe Leu Pro Asp Ser Ile Thr Leu Ser Trp Lys Tyr Lys Asn Asn Ser
                35                 40                 45

Asp Ile Ser Ser Thr Arg Gly Phe Pro Ser Val Leu Arg Gly Gly Lys
                50                 55                 60

Xaa Ala Ala Thr Ser Gln Val Leu Leu Pro Ser Lys Asp Val Met Gln
65                 70                 75                 80

Gly Thr Asp Glu His Val Val Cys Lys Val Gln His Pro Asn Gly Asn
                85                 90                 95

Lys Glu Lys Asn Val Pro Leu Pro
                100
```

<210> SEQ ID NO 22
<211> LENGTH: 106
<212> TYPE: PRT
<213> ORGANISM: Homo sapiens

<400> SEQUENCE: 22

```
Val Cys Ser Arg Asp Phe Thr Pro Pro Thr Val Lys Ile Leu Gln Ser
1               5                  10                 15

Ser Cys Asp Gly Gly Gly His Phe Pro Pro Thr Ile Gln Leu Leu Cys
                20                 25                 30

Leu Val Ser Gly Tyr Thr Pro Gly Thr Ile Asn Ile Thr Trp Leu Glu
                35                 40                 45

Asp Gly Gln Val Met Asp Val Asp Leu Ser Thr Ala Ser Thr Thr Gln
                50                 55                 60

Glu Gly Glu Leu Ala Ser Thr Gln Ser Glu Leu Thr Leu Ser Gln Lys
65                 70                 75                 80
```

```
His Trp Leu Ser Asp Arg Thr Tyr Thr Cys Gln Val Thr Tyr Gln Gly
            85                  90                  95

His Thr Phe Glu Asp Ser Thr Lys Lys Cys
            100                 105

<210> SEQ ID NO 23
<211> LENGTH: 110
<212> TYPE: PRT
<213> ORGANISM: Homo sapiens
<220> FEATURE:
<221> NAME/KEY: MOD_RES
<222> LOCATION: (69)..(69)
<223> OTHER INFORMATION: Pro or Thr
<220> FEATURE:
<221> NAME/KEY: MOD_RES
<222> LOCATION: (87)..(87)
<223> OTHER INFORMATION: Gly or Ser

<400> SEQUENCE: 23

Val Ile Ala Glu Leu Pro Pro Lys Val Ser Val Phe Val Pro Pro Arg
1               5                   10                  15

Asp Gly Phe Phe Gly Asn Pro Arg Lys Ser Lys Leu Ile Cys Gln Ala
                20                  25                  30

Thr Gly Phe Ser Pro Arg Gln Ile Gln Val Ser Trp Leu Arg Glu Gly
            35                  40                  45

Lys Gln Val Gly Ser Gly Val Thr Thr Asp Gln Val Gln Ala Glu Ala
        50                  55                  60

Lys Glu Ser Gly Xaa Thr Thr Tyr Lys Val Thr Ser Thr Leu Thr Ile
65                  70                  75                  80

Lys Glu Ser Asp Trp Leu Xaa Gln Ser Met Phe Thr Cys Arg Val Asp
                85                  90                  95

His Arg Gly Leu Thr Phe Gln Gln Asn Ala Ser Ser Met Cys
                100                 105                 110

<210> SEQ ID NO 24
<211> LENGTH: 15
<212> TYPE: PRT
<213> ORGANISM: Homo sapiens

<400> SEQUENCE: 24

Glu Pro Lys Ser Cys Asp Lys Thr His Thr Cys Pro Pro Cys Pro
1               5                   10                  15

<210> SEQ ID NO 25
<211> LENGTH: 109
<212> TYPE: PRT
<213> ORGANISM: Homo sapiens

<400> SEQUENCE: 25

Ala Asp Ser Asn Pro Arg Gly Val Ser Ala Tyr Leu Ser Arg Pro Ser
1               5                   10                  15

Pro Phe Asp Leu Phe Ile Arg Lys Ser Pro Thr Ile Thr Cys Leu Val
                20                  25                  30

Val Asp Leu Ala Pro Ser Lys Gly Thr Val Asn Leu Thr Trp Ser Arg
            35                  40                  45

Ala Ser Gly Lys Pro Val Asn His Ser Thr Arg Lys Glu Glu Lys Gln
        50                  55                  60

Arg Asn Gly Thr Leu Thr Val Thr Ser Thr Leu Pro Val Gly Thr Arg
65                  70                  75                  80

Asp Trp Ile Glu Gly Glu Thr Tyr Gln Cys Arg Val Thr His Pro His
                85                  90                  95
```

```
Leu Pro Arg Ala Leu Met Arg Ser Thr Thr Lys Thr Ser
                100                 105

<210> SEQ ID NO 26
<211> LENGTH: 110
<212> TYPE: PRT
<213> ORGANISM: Homo sapiens

<400> SEQUENCE: 26

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 27
<211> LENGTH: 108
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Val or Gly
<220> FEATURE:
<221> NAME/KEY: MOD_RES
<222> LOCATION: (6)..(6)
<223> OTHER INFORMATION: Thr or Ile
<220> FEATURE:
<221> NAME/KEY: MOD_RES
<222> LOCATION: (12)..(12)
<223> OTHER INFORMATION: Ala or Ser

<400> SEQUENCE: 27

Xaa Pro Asp Gln Asp Xaa Ala Ile Arg Val Phe Xaa Ile Pro Pro Ser
1               5                   10                  15

Phe Ala Ser Ile Phe Leu Thr Lys Ser Thr Lys Leu Thr Cys Leu Val
            20                  25                  30

Thr Asp Leu Thr Thr Tyr Asp Ser Val Thr Ile Ser Trp Thr Arg Gln
        35                  40                  45

Asn Gly Glu Ala Val Lys Thr His Thr Asn Ile Ser Glu Ser His Pro
    50                  55                  60

Asn Ala Thr Phe Ser Ala Val Gly Glu Ala Ser Ile Cys Glu Asp Asp
65                  70                  75                  80

Trp Asn Ser Gly Glu Arg Phe Thr Cys Thr Val Thr His Thr Asp Leu
                85                  90                  95

Pro Ser Pro Leu Lys Gln Thr Ile Ser Arg Pro Lys
            100                 105

<210> SEQ ID NO 28
<211> LENGTH: 110
<212> TYPE: PRT
<213> ORGANISM: Homo sapiens
```

-continued

<400> SEQUENCE: 28

Gly Pro Arg Ala Ala Pro Glu Val Tyr Ala Phe Ala Thr Pro Glu Trp
1               5                   10                  15

Pro Gly Ser Arg Asp Lys Arg Thr Leu Ala Cys Leu Ile Gln Asn Phe
            20                  25                  30

Met Pro Glu Asp Ile Ser Val Gln Trp Leu His Asn Glu Val Gln Leu
        35                  40                  45

Pro Asp Ala Arg His Ser Thr Thr Gln Pro Arg Lys Thr Lys Gly Ser
    50                  55                  60

Gly Phe Phe Val Phe Ser Arg Leu Glu Val Thr Arg Ala Glu Trp Glu
65                  70                  75                  80

Gln Lys Asp Glu Phe Ile Cys Arg Ala Val His Glu Ala Ala Ser Pro
                85                  90                  95

Ser Gln Thr Val Gln Arg Ala Val Ser Val Asn Pro Gly Lys
            100                 105                 110

<210> SEQ ID NO 29
<211> LENGTH: 107
<212> TYPE: PRT
<213> ORGANISM: Homo sapiens

<400> SEQUENCE: 29

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 30
<211> LENGTH: 131
<212> TYPE: PRT
<213> ORGANISM: Homo sapiens

<400> SEQUENCE: 30

Gly Val Ala Leu His Arg Pro Asp Val Tyr Leu Leu Pro Pro Ala Arg
1               5                   10                  15

Glu Gln Leu Asn Leu Arg Glu Ser Ala Thr Ile Thr Cys Leu Val Thr
            20                  25                  30

Gly Phe Ser Pro Ala Asp Val Phe Val Gln Trp Met Gln Arg Gly Gln
        35                  40                  45

Pro Leu Ser Pro Glu Lys Tyr Val Thr Ser Ala Pro Met Pro Glu Pro
    50                  55                  60

Gln Ala Pro Gly Arg Tyr Phe Ala His Ser Ile Leu Thr Val Ser Glu
65                  70                  75                  80

Glu Glu Trp Asn Thr Gly Glu Thr Tyr Thr Cys Val Val Ala His Glu
                85                  90                  95

```
Ala Leu Pro Asn Arg Val Thr Glu Arg Thr Val Asp Lys Ser Thr Gly
                100                 105                 110

Lys Pro Thr Leu Tyr Asn Val Ser Leu Val Met Ser Asp Thr Ala Gly
            115                 120                 125

Thr Cys Tyr
        130

<210> SEQ ID NO 31
<211> LENGTH: 428
<212> TYPE: PRT
<213> ORGANISM: Homo sapiens

<400> SEQUENCE: 31

Ala Ser Thr Gln Ser Pro Ser Val Phe Pro Leu Thr Arg Cys Cys Lys
1               5                   10                  15

Asn Ile Pro Ser Asn Ala Thr Ser Val Thr Leu Gly Cys Leu Ala Thr
            20                  25                  30

Gly Tyr Phe Pro Glu Pro Val Met Val Thr Cys Asp Thr Gly Ser Leu
        35                  40                  45

Asn Gly Thr Thr Met Thr Leu Pro Ala Thr Thr Leu Thr Leu Ser Gly
    50                  55                  60

His Tyr Ala Thr Ile Ser Leu Leu Thr Val Ser Gly Ala Trp Ala Lys
65                  70                  75                  80

Gln Met Phe Thr Cys Arg Val Ala His Thr Pro Ser Ser Thr Asp Trp
                85                  90                  95

Val Asp Asn Lys Thr Phe Ser Val Cys Ser Arg Asp Phe Thr Pro Pro
            100                 105                 110

Thr Val Lys Ile Leu Gln Ser Ser Cys Asp Gly Gly His Phe Pro
            115                 120                 125

Pro Thr Ile Gln Leu Leu Cys Leu Val Ser Gly Tyr Thr Pro Gly Thr
        130                 135                 140

Ile Asn Ile Thr Trp Leu Glu Asp Gly Gln Val Met Asp Val Asp Leu
145                 150                 155                 160

Ser Thr Ala Ser Thr Thr Gln Glu Gly Glu Leu Ala Ser Thr Gln Ser
                165                 170                 175

Glu Leu Thr Leu Ser Gln Lys His Trp Leu Ser Asp Arg Thr Tyr Thr
            180                 185                 190

Cys Gln Val Thr Tyr Gln Gly His Thr Phe Glu Asp Ser Thr Lys Lys
        195                 200                 205

Cys Ala Asp Ser Asn Pro Arg Gly Val Ser Ala Tyr Leu Ser Arg Pro
    210                 215                 220

Ser Pro Phe Asp Leu Phe Ile Arg Lys Ser Pro Thr Ile Thr Cys Leu
225                 230                 235                 240

Val Val Asp Leu Ala Pro Ser Lys Gly Thr Val Asn Leu Thr Trp Ser
                245                 250                 255

Arg Ala Ser Gly Lys Pro Val Asn His Ser Thr Arg Lys Glu Glu Lys
            260                 265                 270

Gln Arg Asn Gly Thr Leu Thr Val Thr Ser Thr Leu Pro Val Gly Thr
        275                 280                 285

Arg Asp Trp Ile Glu Gly Glu Thr Tyr Gln Cys Arg Val Thr His Pro
    290                 295                 300

His Leu Pro Arg Ala Leu Met Arg Ser Thr Thr Lys Thr Ser Gly Pro
305                 310                 315                 320

Arg Ala Ala Pro Glu Val Tyr Ala Phe Ala Thr Pro Glu Trp Pro Gly
                325                 330                 335
```

```
Ser Arg Asp Lys Arg Thr Leu Ala Cys Leu Ile Gln Asn Phe Met Pro
            340                 345                 350

Glu Asp Ile Ser Val Gln Trp Leu His Asn Glu Val Gln Leu Pro Asp
            355                 360                 365

Ala Arg His Ser Thr Thr Gln Pro Arg Lys Thr Lys Gly Ser Gly Phe
            370                 375                 380

Phe Val Phe Ser Arg Leu Glu Val Thr Arg Ala Glu Trp Glu Gln Lys
385                 390                 395                 400

Asp Glu Phe Ile Cys Arg Ala Val His Glu Ala Ala Ser Pro Ser Gln
                    405                 410                 415

Thr Val Gln Arg Ala Val Ser Val Asn Pro Gly Lys
            420                 425

<210> SEQ ID NO 32
<211> LENGTH: 330
<212> TYPE: PRT
<213> ORGANISM: Homo sapiens

<400> SEQUENCE: 32

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                    85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
```

```
                    275                 280                 285
Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 33
<211> LENGTH: 453
<212> TYPE: PRT
<213> ORGANISM: Homo sapiens

<400> SEQUENCE: 33

Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
                20                  25                  30

Phe Leu Pro Asp Ser Ile Thr Leu Ser Trp Lys Tyr Lys Asn Asn Ser
            35                  40                  45

Asp Ile Ser Ser Thr Arg Gly Phe Pro Ser Val Leu Arg Gly Gly Lys
50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95

Lys Glu Lys Asn Val Pro Leu Pro Val Ile Ala Glu Leu Pro Pro Lys
            100                 105                 110

Val Ser Val Phe Val Pro Pro Arg Asp Gly Phe Phe Gly Asn Pro Arg
        115                 120                 125

Lys Ser Lys Leu Ile Cys Gln Ala Thr Gly Phe Ser Pro Arg Gln Ile
130                 135                 140

Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
                165                 170                 175

Lys Val Thr Ser Thr Leu Thr Ile Lys Glu Ser Asp Trp Leu Gly Gln
            180                 185                 190

Ser Met Phe Thr Cys Arg Val Asp His Arg Gly Leu Thr Phe Gln Gln
        195                 200                 205

Asn Ala Ser Ser Met Cys Val Pro Asp Gln Asp Thr Ala Ile Arg Val
210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
                245                 250                 255

Ile Ser Trp Thr Arg Gln Asn Gly Glu Ala Val Lys Thr His Thr Asn
            260                 265                 270

Ile Ser Glu Ser His Pro Asn Ala Thr Phe Ser Ala Val Gly Glu Ala
        275                 280                 285

Ser Ile Cys Glu Asp Asp Trp Asn Ser Gly Glu Arg Phe Thr Cys Thr
290                 295                 300

Val Thr His Thr Asp Leu Pro Ser Pro Leu Lys Gln Thr Ile Ser Arg
305                 310                 315                 320
```

```
Pro Lys Gly Val Ala Leu His Arg Pro Asp Val Tyr Leu Leu Pro Pro
            325             330             335

Ala Arg Glu Gln Leu Asn Leu Arg Glu Ser Ala Thr Ile Thr Cys Leu
            340             345             350

Val Thr Gly Phe Ser Pro Ala Asp Val Phe Val Gln Trp Met Gln Arg
            355             360             365

Gly Gln Pro Leu Ser Pro Glu Lys Tyr Val Thr Ser Ala Pro Met Pro
    370             375             380

Glu Pro Gln Ala Pro Gly Arg Tyr Phe Ala His Ser Ile Leu Thr Val
385             390             395             400

Ser Glu Glu Glu Trp Asn Thr Gly Glu Thr Tyr Thr Cys Val Val Ala
            405             410             415

His Glu Ala Leu Pro Asn Arg Val Thr Glu Arg Thr Val Asp Lys Ser
            420             425             430

Thr Gly Lys Pro Thr Leu Tyr Asn Val Ser Leu Val Met Ser Asp Thr
            435             440             445

Ala Gly Thr Cys Tyr
    450
```

CONSTANT CHAIN MODIFIED BISPECIFIC, PENTA- AND HEXAVALENT IG-M ANTIBODIES

This application is a national stage application filed under 35 USC § 371 of PCT Application No. PCT/US2014/054079, filed Sep. 4, 2014, which claims the benefit of priority under 35 USC § 119(e) of provisional application Nos. 61/874,277, filed Sep. 5, 2013 and 61/874,284, filed Sep. 5, 2013, the entire contents of each application are incorporated herein by reference.

REFERENCE TO SEQUENCE LISTING SUBMITTED ELECTRONICALLY

The instant application contains a Sequence Listing which has been submitted electronically in ASCII format and is hereby incorporated by reference in its entirety. Said ASCII copy, created on Feb. 5, 2018, is named IGM-0001-2-US_SL_Substitute_ST25.txt and is 86,421 bytes in size.

FIELD OF THE INVENTION

The present invention concerns binding molecules with penta- or hexameric structure.

In particular, the invention relates to binding molecules having a penta- or hexameric ring structure comprising five or six bispecific binding units. In the binding molecules of the present invention each of the bispecific binding units binds two different binding targets or different binding regions (e.g. epitopes) on the same binding target, and each of the five or six bispecific binding units have the same binding specificities (bind to the same two binding targets). In a particular embodiment, the invention concerns bispecific antibodies with penta- or hexameric structure, comprising five or six bispecific binding units.

In a different aspect, the invention includes binding molecules comprising five or six monospecific binding units, where (i) each of the monospecific binding units comprises two IgM heavy chain constant regions each comprising at least a Cµ3 and Cµ4 domain conjugated to a binding region to a binding target, (ii) at least two of the monospecific binding units bind to different binding target. The invention further includes binding molecules comprising five or six bispecific binding units, where (i) each of the bispecific binding units comprises two IgM heavy chain constant regions each comprising at least a Cµ3 and Cµ4 domain conjugated to a binding region to a binding target, and (ii) at least two of the bispecific binding units bind to different binding targets. In a particular embodiment, the binding molecules are multi-specific IgM antibodies.

BACKGROUND OF THE INVENTION

Since the advent of humanized antibodies, the therapeutic use of antibodies such as Rituxan® (rituximab), Herceptin® (trastuzumab) and Avastin® (bevacizumab), has revolutionized the fields of medicine, including oncology, the treatment of inflammatory disorders, such as rheumatoid arthritis, and many other indications. In the United States, more than 30 human or humanized antibodies have been approved for clinical use, and more than 600 new antibodies or antibody-like molecules are in various stages of development. Some antibodies have antagonistic function on soluble target molecules such as vascular endothelial growth factor (VEGF) or tumor necrosis factor (TNF), whose actions are part of the pathologic process of a disease. Alternatively, antibodies can bind, block and/or induce destruction of pathologic cells in certain diseases, such as cancer. The main functions of these therapeutic antibodies are binding through the Fab region, and recruitment of effector function via the Fc domain (which also mediates the long circulating half-life of antibodies). One of the major advantages of antibodies compared to small molecule drugs, can be their exquisite specificity. Antibodies can very accurately target selected protein antigens, such as oncogenes, to the exclusion of very similar homologs, allowing for benign safety profiles. Hence, antibodies are well characterized for specific single targeting function.

As the field has progressed, antibody function has been enhanced through creative means of protein engineering, such as to provide higher affinity, longer half-life, and/or better tissue distribution, as well as combination of small and large molecule technologies for increased focus of cell destruction via toxic payload delivery (e.g. antibody-drug conjugates). Another approach to improving antibody function takes advantage of the bivalent binding of the immunoglobulin G (IgG) structure which allows one IgG molecule to bind two antigens. Indeed, in certain applications, there exists good potential for asymmetric antibodies to exert useful functions by simultaneously binding two different target antigens. To address this need, a variety of constructs have been produced to yield a single molecule that can bind two different antigens, allowing for functions never before seen in nature. An example of this bi-specific approach is "blinatumumab" (MT103) which binds the CD3 and CD19 receptors, on T- and B-cells, respectively. This tethering of a cytotoxic T cell to a cancerous B-cell, allows for effective treatment of B-cell leukemia.

However, there remain significant technical difficulties in construction, expression and production of bispecific antibodies. Although bispecific antibodies are regarded as promising therapeutic agents due to their ability to simultaneously bind two different antigens, their utility is limited due to problems with stability and manufacturing complexity.

Various forms of protein engineering have been used to match heterologous heavy chains, plus appropriate pairwise matching of heavy and light chains to efficiently yield a bi-specific IgG. In addition, various bispecific antibody formats, including quadromas, chemical heteroconjugates, recombinant constructs using selected heterodimerization domains and recombinant constructs of minimal size consisting of two minimal antigen-binding sites.

However, all of these efforts have been fraught with difficulty.

Thus, despite efforts directed toward the development of bispecific therapeutic antibodies, there remains a great need for developing more efficient platforms that can lead to more efficient and flexible production of bi- and multispecific antibodies, thereby shortening the timeline between discovery and clinical introduction of such therapeutics and enabling the design and production of new types of antibody formats with multiple specificities and/or valencies.

SUMMARY OF THE INVENTION

The present invention concerns binding molecules having a penta- or hexameric ring structure, such as, for example, isolated IgM antibodies with five or six bispecific binding units, and methods and means for making and using the same.

In one aspect, the invention concerns a binding molecule having a penta- or hexameric ring structure comprising five or six bispecific binding units, wherein each of the bispecific binding units has the same two binding specificities and comprises a first chain comprising at least a Cµ4 domain of an IgM heavy chain constant region conjugated to a first binding region to a first binding target, and a second chain comprising at least a Cµ4 domain of an IgM heavy chain constant region and a second binding region to a second binding target, wherein the first and second binding targets are different, and wherein the first and second chains are assembled to create a bispecific binding unit as a result of an asymmetric interface created between their respective IgM heavy chain constant regions.

In one embodiment, the bispecific binding units are identical.

In another embodiment, the binding molecule further comprises an IgM J chain.

In yet another embodiment, the binding molecule has a pentameric ring structure.

In a further embodiment, the binding molecule has a hexameric ring structure.

In a still further embodiment, in the binding molecule the first and the second chains further comprise a Cµ3 domain of an IgM heavy chain constant region.

In another embodiment, the first and second chains further comprise a Cµ2 domain of an IgM heavy chain constant region.

In other embodiments, the first and second binding targets are selected from peptides, polypeptides, glycoproteins, nucleic acid molecules, and organic and non-organic small molecules, including, without limitation, soluble polypeptides, cell surface receptors, ligands, molecular transporters, enzymes and substrates of enzymes.

In a still further embodiment, the first and second binding targets are two sites on the same soluble target, two sites on the same cell surface receptor target, two different soluble targets, two cell surface receptor targets, one soluble target and one cell surface receptor target, one soluble or cell surface receptor target and one long residence time target, one soluble target and one matrix protein or substrate target, one soluble or receptor target and one molecular transporter target, or two different cell types.

The conjugation of the binding regions to the rest of the molecule may take place by fusion. Thus, for example, the first and second binding regions may be fused to the N-termini of the first and second IgM heavy chain constant regions, respectively.

In a particular embodiment, the first and second binding regions are variable regions of an antibody.

In another embodiment, the first and second binding targets are two different antigens.

In yet another embodiment, the first and second binding targets are different epitopes on the same antigen.

In further embodiments, the first and second binding regions may be two different antibody heavy chain variable regions, binding to two binding targets, or to different epitopes on the same binding target.

In the binding molecules of the present invention the antibody heavy chain variable regions may be from an IgG, IgA, IgE, and/or IgM antibody, preferably from an IgM antibody. Preferably, the binding molecules herein are bispecific IgM molecules, which may, but are not required to, further comprise at least one IgM light chain variable region sequence associated with one of two different IgM heavy chain variable regions.

In a particular embodiment, in the binding molecules of the present invention at least some of the asymmetric interfaces between the IgM heavy chain constant regions of the two chains of a binding unit are created by a salt bridge formed by pair-wise switches between oppositely charged amino acid residues in at least one of the Cµ2, Cµ3 and/or Cµ4 domains of the two chains of said binding unit.

Thus, a salt bridge may be formed between at least one of the Cµ2-Cµ2, Cµ4-Cµ4, and Cµ2-Cµ3-Cµ4 domains of the two chains of a binding unit.

In one embodiment, the pair-wise switches are selected from the group consisting of E→K, K→E; R→E, E→R; D→K, K→D; and R→D, D→R.

In another embodiment, the binding molecule may comprise at least one pair-wise charged amino acid residue switch in the Cµ4-Cµ4 domains, where the switch may, for example, be selected from the group consisting of R328E, D↔E339R,K; R344E,D↔S330R,K; K376E,D↔E385R,K; R427E,D↔E339R,K; and T354E,D↔I397R,K, where the amino acid coordinates refer to the human IgM heavy chain constant region of SEQ ID NO: 33.

In a further embodiment, at least one pair-wise charged amino acid switch between the Cµ2-Cµ2 domains, and may, for example, be selected from the group consisting of E167R,K↔K177E,D and K169E,D↔E170R,K, where the amino acid coordinates refer to the human IgM heavy chain constant region of SEQ ID NO: 33.

In a still further embodiment, at least one pair-wise charged amino acid residue switch is in the Cµ2-Cµ3-Cµ4 domains, and may, for example, be selected from the group consisting of D121K,R↔K315D,E; K150E,D↔E385K,R; and K185D,E↔D360K,R, where the amino acid coordinates refer to the human IgM heavy chain constant region of SEQ ID NO: 33.

In a further embodiment, in the binding molecules of the present invention at least some of the asymmetric interfaces between the IgM heavy chain constant regions of the two chains of a binding unit are created through knobs-into-holes connections, which may, for example, be created by mutations selected from the group consisting of knobs: T350→Y, F,W; and H395→Y,F; and holes: L352→G,A,V,I,M,S,T; H395→A,V,I,L,M,F,Y; F393→W,Y; I397→A,V,S,T; T350→S,A,V; and T348→S, where the amino acid coordinates refer to the human IgM heavy chain constant region of SEQ ID NO: 33.

In a specific embodiment, in the binding molecules of the present invention the light chain variable region sequences, if present, are coupled to their matching heavy chain variable region by creating an asymmetric interface between the light and heavy chains.

In other embodiments, the asymmetric interface is created by CrossMab technique, knobs-into-holes coupling and/or salt bridges coupling.

The binding molecules of the present invention might comprise a common light chain and/or might be conjugated to a toxin or a chemotherapeutic agent. Preferably, conjugation is by fusion, but conjugation by a chemical linker is also included within the scope of the invention.

The binding molecules herein might be bispecific antibodies with a penta- or hexameric structure, which might be chimeric or humanized.

In a different aspect, the invention concerns a composition comprising at least about 70%, or at least 80%, or at least 90% or at least 95%, of at least 98%, or at last 99% of the binding molecule as hereinabove defined.

In a particular embodiment, the composition is a pharmaceutical composition.

The present invention further concerns a multi-specific binding molecule having a penta- or hexameric ring structure comprising five or six monospecific binding units, wherein (i) each of the monospecific binding units comprises two IgM heavy chain constant regions each comprising at least a Cμ3 and Cμ4 domain conjugated to a binding region to a binding target, (ii) at least two of the monospecific binding units bind to different binding targets, and (iii) an external asymmetric interface is created between the heavy chain constant regions of the neighboring monospecific binding units that bind to different binding targets.

In one embodiment, at least three of the monospecific binding units bind to different binding targets.

In another embodiment, at least four of said monospecific binding units bind to different binding targets.

In yet another embodiment, the binding molecule has a pentameric ring structure and all five monospecific binding units bind to different targets.

In a further embodiment, the binding molecule has a hexameric ring structure and at least five of said monospecific binding units bind to different targets.

In a still further embodiment, all six of the monospecific binding units bind to different targets.

In another aspect, the invention concerns a multi-specific binding molecule having a penta- or hexameric ring structure comprising five or six bispecific binding units, where (i) each of the bispecific binding units comprises two IgM heavy chain constant regions each comprising at least a Cμ3 and Cμ4 domain conjugated to a binding region to a binding target, (ii) at least two of the bispecific binding units bind to different binding targets, (iii) an internal asymmetric interface is created between two IgM heavy chain constant regions of each bispecific binding unit, and (iv) an external asymmetric interface is created between the heavy chain constant regions of the neighboring bispecific binding units binding to different targets.

In one embodiment, at least three of the bispecific binding units bind to different binding targets.

In another embodiment, at least four of the bispecific binding units bind to different binding targets.

In yet another embodiment, the binding molecule has a pentameric ring structure and all five bispecific binding units bind to different targets.

In a further embodiment, the binding molecule has a hexameric ring structure and at least five of the bispecific binding units bind to different targets.

In a still further embodiment, all six bispecific binding units bind to different targets.

In a different embodiment, the multi-specific binding molecule further comprises an IgM J chain.

In various embodiments, the multi-specific binding molecule may have a pentameric or hexameric ring structure.

Regardless of the number and nature of the binding specificities of the multi-specific binding molecules of the present invention, the following specific embodiments apply:

In one embodiment, in at least one of the binding units the IgM heavy chain constant regions further comprise a Cμ2 domain. In yet another embodiment, in all of the binding units the IgM heavy chain constant regions further comprise a Cμ2 domain. In various embodiments, the multi-specific binding molecules of the present invention may bind to binding targets selected from peptides, polypeptides, glycoproteins, nucleic acid molecules, and organic and non-organic small molecules.

In other embodiments, the multi-specific binding molecules of the present invention bind to binding targets selected from soluble polypeptides, cell surface receptors, ligands, molecular transporters, enzymes and substrates of enzymes.

In further embodiments, the multi-specific binding molecules of the present invention binding to different targets are selected from the group consisting of binding units binding to sites on the same soluble target; sites on the same cell surface receptor target; different soluble targets; different cell surface receptor targets; soluble and cell surface receptor targets; soluble or cell surface receptor and long residence time targets; soluble and matrix protein or substrate targets; soluble or receptor and molecular transporter targets, and different cell types.

In a particular embodiment, in the binding units within the binding molecules of the present invention the conjugation between the IgM heavy chain constant regions and the binding region to a binding target is by fusion. Thus, for example, the binding regions may be fused to the N-termini of the IgM heavy chain constant regions.

In one embodiment, at least one of the binding regions is a variable region of an antibody.

In another embodiment, all of the binding regions are antibody heavy chain variable regions.

In yet another embodiment, at least two binding targets are different antigens.

In a further embodiment, at least two binding targets are different epitopes on the same antigen.

In all aspects and embodiments, the antibody heavy chain variable regions may be from an IgG, IgA, IgE, or IgM antibody, preferably from an IgM antibody.

In a preferred embodiment, the multi-specific binding molecule of the present invention is a multi-specific IgM antibody.

In one embodiment, the multi-specific IgM antibody of the present invention further comprises at least one IgM light chain variable region sequence associated with an IgM heavy chain variable region in at least one of the binding units.

In another embodiment, the multi-specific IgM antibody further comprises an IgM light chain variable region sequence associated with each of the IgM heavy chain variable regions.

In all aspects and embodiments, the external asymmetric interface is created by alteration(s) within the Cμ3 domain. In one embodiment, the alteration is created by a salt bridge formed by pair-wise switches between oppositely charged amino acid residues in the Cμ3 domain.

In various embodiments, the salt bridge providing the external asymmetric interface is formed by at least one pair-wise charged amino acid residue switch in the Cμ3-Cμ3 domains, which may, for example be K238↔D293 or K268↔D294 in the neighboring μ chains, where the amino acid coordinates refer to the human IgM heavy chain constant region of SEQ ID NO: 33.

In all aspects and embodiments, in the multi-specific binding molecules, e.g. multi-specific IgM antibodies, of the present invention the internal asymmetric interfaces are created by a salt bridge formed by pair-wise switches between oppositely charged amino acid residues in at least one of the Cμ2, Cμ3 and/or Cμ4 domains.

In one embodiment, a salt bridge is formed between at least one of the Cμ2-Cμ2, Cμ4-Cμ4, and Cμ2-Cμ3-Cμ4 domains of the two chains of said binding unit.

In another embodiment, the pair-wise switches are selected from the group consisting of E→K, K→E; R→E, E→R; D→K, K→D; and R→D, D→R.

In a further embodiment, the multi-specific binding molecule, e.g. multi-specific IgM antibody, comprises at least one pair-wise charged amino acid residue switch in the Cμ4-Cμ4 domains, which may, for example be selected from the group consisting of R328E,D↔E339R,K; R344E,D↔S330R,K; K376E,D↔E385R,K; R427E,D↔E339R,K; and T354E,D↔I397R,K, where the amino acid coordinates refer to the human IgM heavy chain constant region of SEQ ID NO: 33.

In a still further embodiment, the multi-specific binding molecule, e.g. multi-specific IgM antibody, comprises at least one pair-wise charged amino acid switch between the Cμ2-Cμ2 domains, which may, for example, be selected from the group consisting of E167R,K↔K177E,D and K169E,D↔E170R,K, where the amino acid coordinates refer to the human IgM heavy chain constant region of SEQ ID NO: 33.

In another embodiment, the multi-specific binding molecule, e.g. multi-specific IgM antibody, comprises at least one pair-wise charged amino acid residue switch in the Cμ2-Cμ3-Cμ4 domains, which may, for example, be selected from the group consisting of D121K,R↔K315D,E; K150E,D↔E385K,R; and K185D,E↔D360K,R, where the amino acid coordinates refer to the human IgM heavy chain constant region of SEQ ID NO: 33.

In all aspects and embodiments, at least some of the external and/or internal asymmetric interfaces between the IgM heavy chain constant regions may be created through knobs-into-holes connections. For example, at least one knobs-into-hole connection may be created by mutations selected from the group consisting of knobs: T350→Y,F,W; and H395→Y,F; and holes: L352→G,A,V,I,M,S,T; H395→A,V,I,L,M,F,Y; F393→W,Y; I397→A,V,S,T; T350→S,A,V; and T348→S, where the amino acid coordinates refer to the human IgM heavy chain constant region of SEQ ID NO: 33.

In the multi-specific IgM antibodies comprising a light chain variable region sequence, such light chain variable region sequences may be coupled to their matching heavy chain variable regions by creating an asymmetric interface between the light and heavy chains. In various embodiments, the asymmetric interface may be created by Cross-Mab technique, knobs-into-holes coupling and/or salt bridges coupling. In a further embodiment, the binding units of the multi-specific binding molecule comprise a common light chain.

In all aspects and embodiments, the multi-specific binding molecule may be conjugated to a toxin or a chemotherapeutic agent, where the conjugation may, for example, be by fusion and/or through a chemical linker.

The multi-specific IgM antibodies of the present invention may be chimeric or humanized.

In a further aspect, the invention concerns a composition comprising at least about 70%, or at least about 80%, or at least about 90%, or at least about 95%, or at least about 98%, or at least about 99% of a multi-specific binding molecule herein. The composition may, for example, be a pharmaceutical composition, comprising at least one pharmaceutically acceptable ingredient.

BRIEF DESCRIPTION OF THE DRAWINGS

FIG. 4A shows the alignment of the CG1 (SEQ ID NO: 20), CE1 (SEQ ID NO: 19) and CM1 (SEQ ID NO: 21) constant domains of human IgG1, IgE and IgM, respectively.

FIG. 4C shows the alignment of the CG2 (SEQ ID NO: 26), CE3 (SEQ ID NO: 25) and CM3 (SEQ ID NO: 27) constant domains of human IgG1, IgE and IgM, respectively.

FIG. 4D shows the alignment of the CG3 (SEQ ID NO: 29), CE4 (SEQ ID NO: 28) and CM4 (SEQ ID NO: 30) constant domains of human IgG, IgE and IgM, respectively.

The complete sequential IgE constant region sequence as shown in FIGS. 4A-4D (SEQ ID Nos 19, 22, 25, and 28) is presented as SEQ ID NO: 31. The complete sequential IgG constant region sequence as shown in FIGS. 4A-4D (SEQ ID Nos 20, 24, 26, and 29) is presented as SEQ ID NO: 32. The complete sequential IgM constant region sequence as shown in FIGS. 4A-4D (SEQ ID Nos 21, 23, 27, and 30) is presented as SEQ ID NO: 33.

In FIGS. 4A-4D:

human IgE sequence (SEQ ID NO: 31) is encoded by GenBank J00222.1 (replaced by AH005273.2); residue numbering from PDB 2WQR; helix (h) and sheet (s) assignments from PDB 2WQR;

human IgG1 (SEQ ID NO: 32) sequence is encoded by GenBank J00228.1 (replaced by AH007035.2); residue numbering from PDB 1OQO; helix (h) and sheet (s) assignments from PDB 1OQO;

human IgM sequence (SEQ ID NO: 33) is encoded by GenBank X14940.1; residue numbering is sequential from start of CM1 domain; reported variance in human IgM sequences noted below IgM sequence for GenBank CAB37838.1, CAC20458.1, AFM37312.1, X57331.1 and J00260.1.

Figure 1:
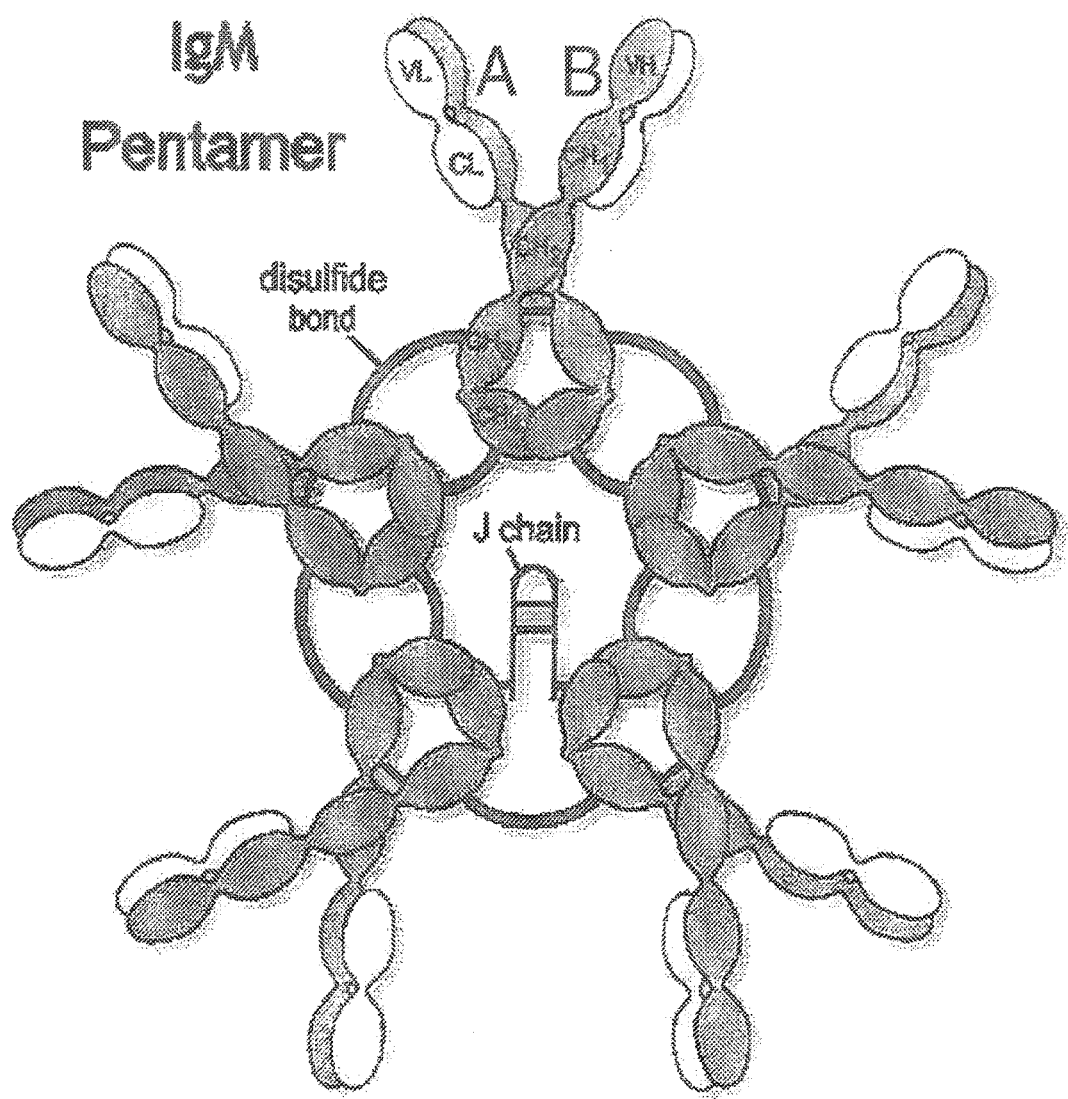
FIG. 1 illustrates the structure of an IgM pentamer, comprising a J chain, wherein chains A and B are identical in native IgM.
Figure 2A:
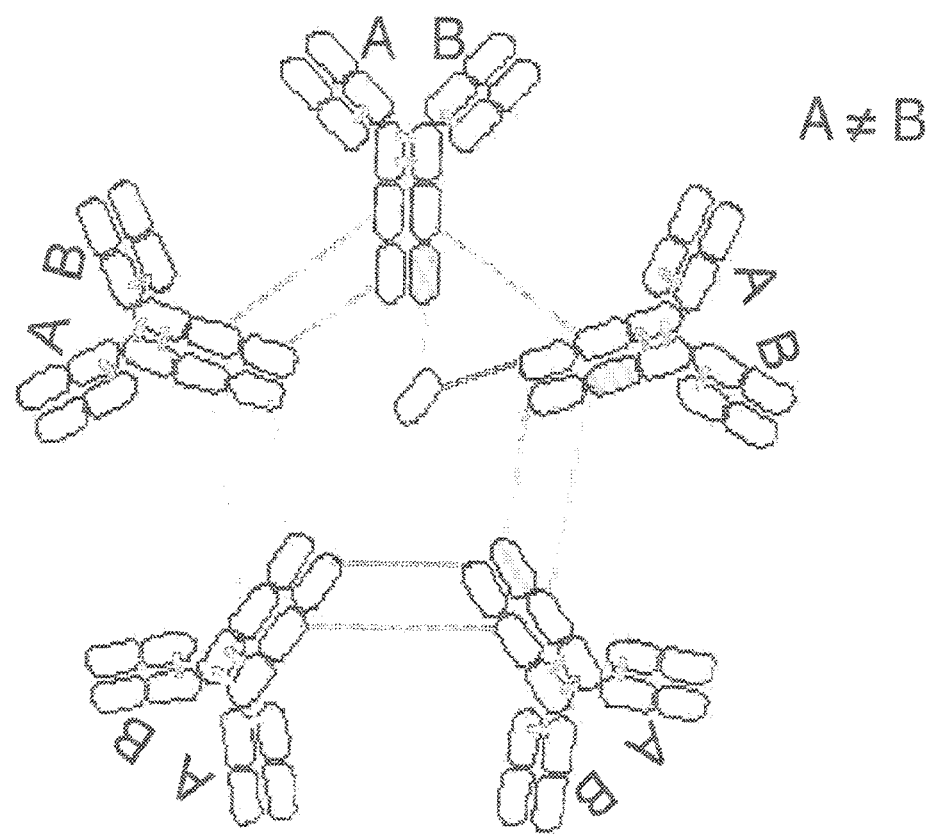
FIG. 2A illustrates a five-membered IgM molecule with two binding specificities, where the heavy (μ) chains designated as A and B are different.
Figure 2B:
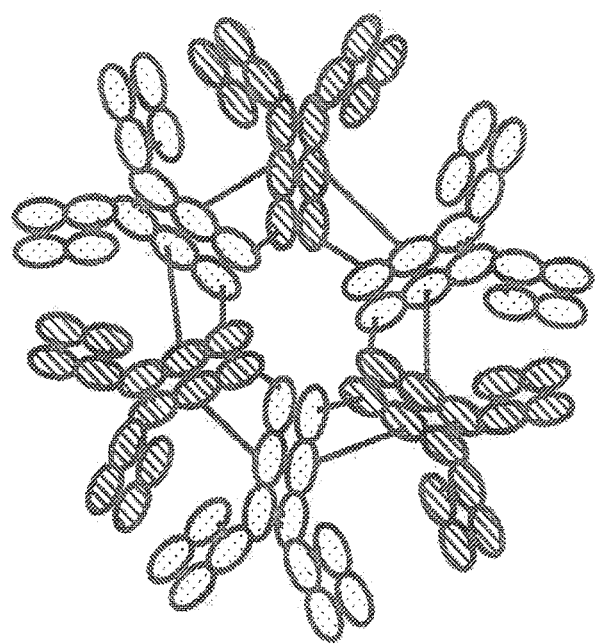
FIG. 2B illustrates a multi-specific IgM antibody comprising five or six monospecific binding units, where (i) each of the monospecific binding units comprises two IgM heavy chain constant regions each comprising at least a Cμ4 domain conjugated to a binding region to a binding target, (ii) at least two of the monospecific binding units bind to different binding target.
Figure 2C:
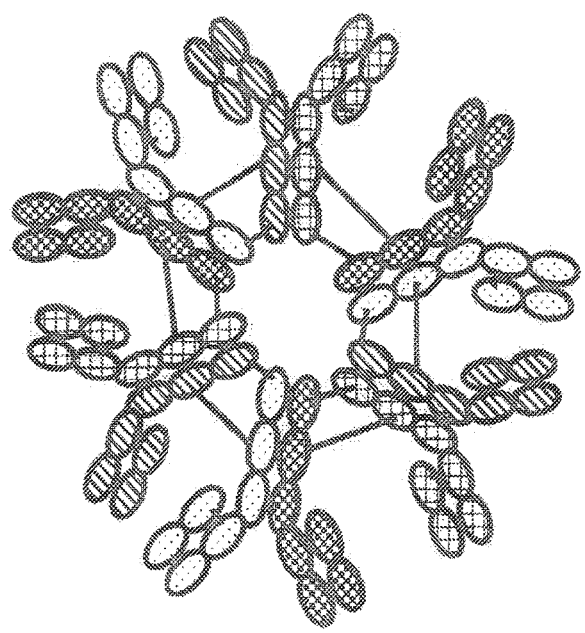
FIG. 2C illustrates a multi-specific IgM antibody comprising five or six bispecific binding units, where (i) each of the bispecific binding units comprises two IgM heavy chain constant regions each comprising at least a Cμ4 domain conjugated to a binding region to a binding target, and (ii) at least two of the bispecific binding units bind to different binding targets.
Figure 3:
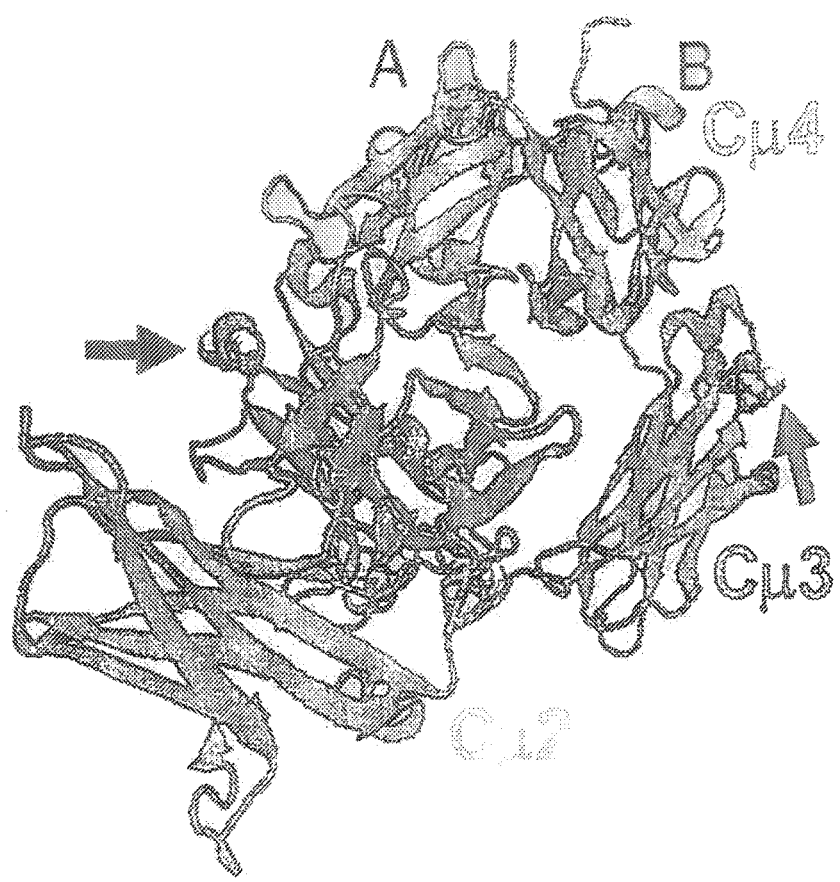
FIG. 3 is a structural model of the A and B heavy chains of an IgM molecule as published in Czajkowsky D. M, Shao Z, PNAS 2009; 106:14960-14965.
Figure 4B:
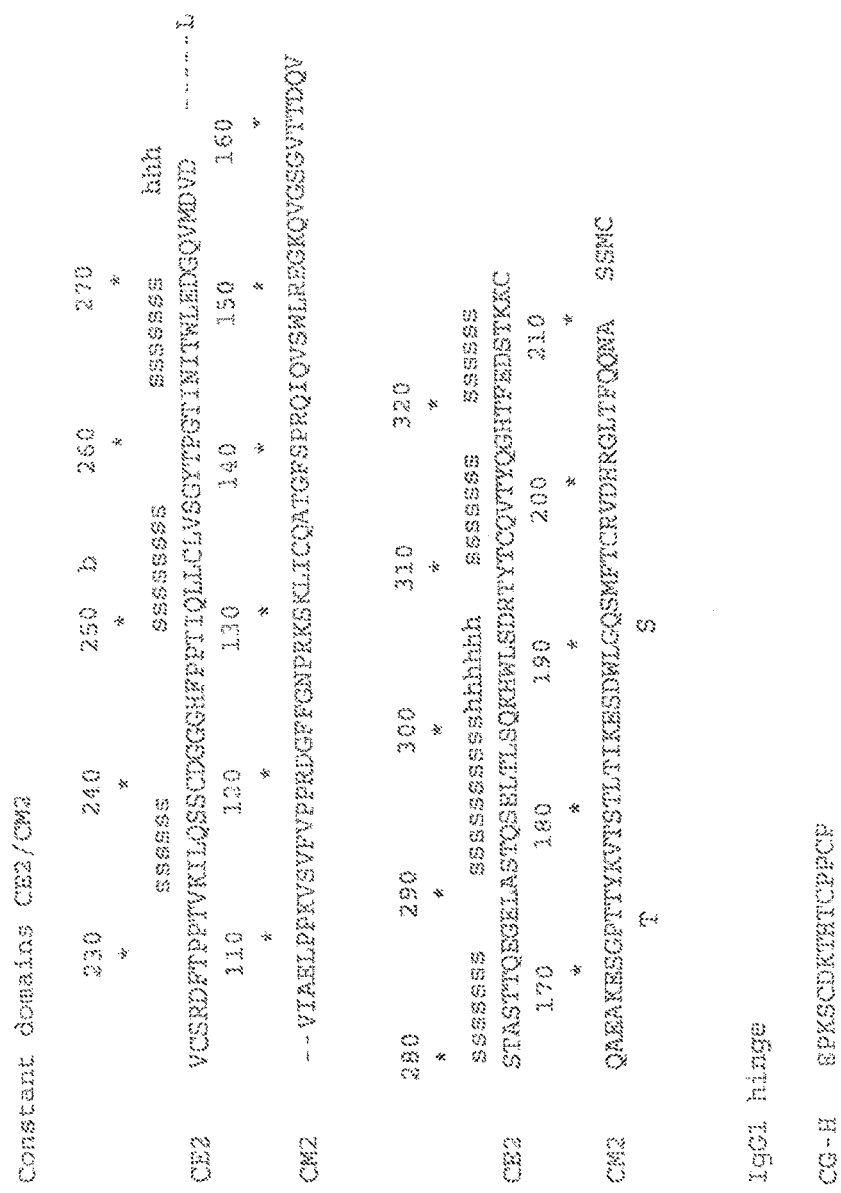
FIG. 4B shows the alignment of the CE2 (SEQ ID NO: 22) and CM2 (SEQ ID NO: 23) constant domains of human IgE and IgM, respectively. CG-H is disclosed as SEQ ID NO: 24.
Figure 5:
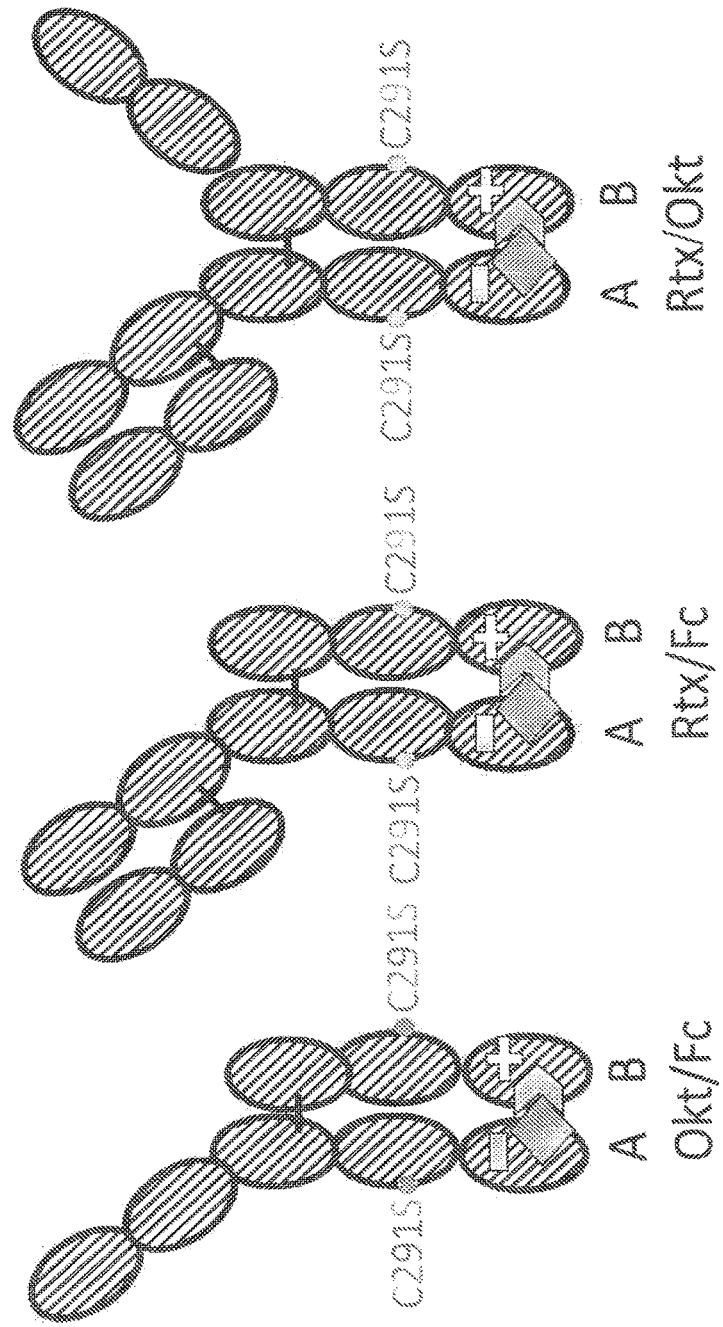

FIG. 5 shows the structure of hetero-monomers prepared in Example 1.

Figure 6:
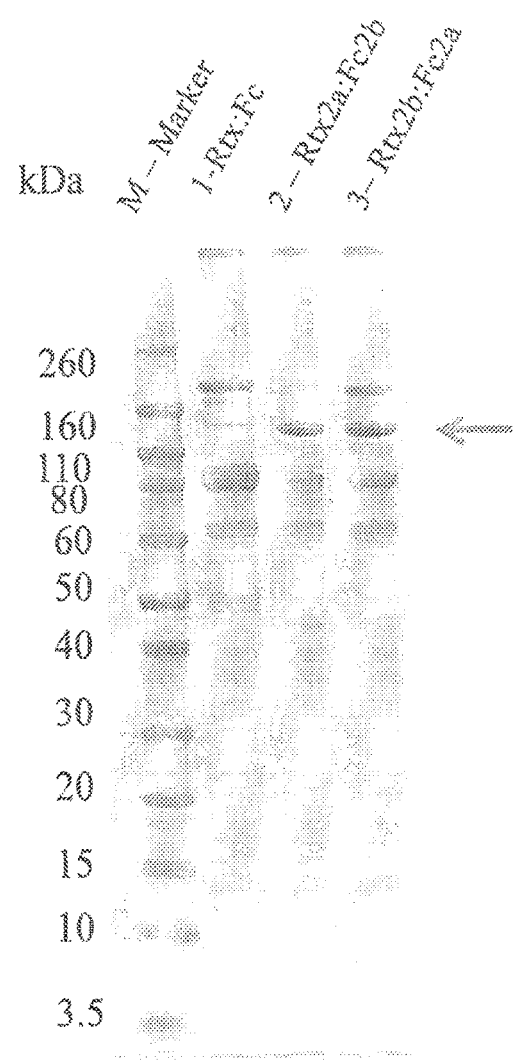

FIG. 6 shows a non-reduced SDS-PAGE gel of wild-type and engineered IgM Fc pairs 2a and 2b.

Lane 1: wild-type Rtx:Fc.

Lane 2: a mixture of Rtx2a:Fc2b, where Rtx2a is composed of a μ chain for chimeric Rituxan (anti-CD20) Vh region fused with CM1 to CM4 of human μ chain with C291S, T350Y, T354E, and I397E mutations and tail piece deletion; and Fc2b is human μ chain CH2 to CH4 and with C291S, L352S, T354K, H395V, and I397K mutations and tail piece deletion, where the amino acid coordinates refer to the human IgM heavy chain constant region of SEQ ID NO: 33.

Lane 3: a mixture of Rtx2b:Fc2a, where Rtx2b is composed of a μ chain for chimeric Rituxan (anti-CD20) Vh region fused with CM1 to CM4 of human mu chain with C291S, L352S, T354K, H395V, and I397K mutations and tail piece deletion; and Fc2a consists of a human μ chain CH2 to CH4 region with C291S, T350Y, T354E, and I397E mutations and tail piece deletion, where the amino acid coordinates refer to the human IgM heavy chain constant region of SEQ ID NO: 33. Arrow indicates heterodimer.

Figure 7:
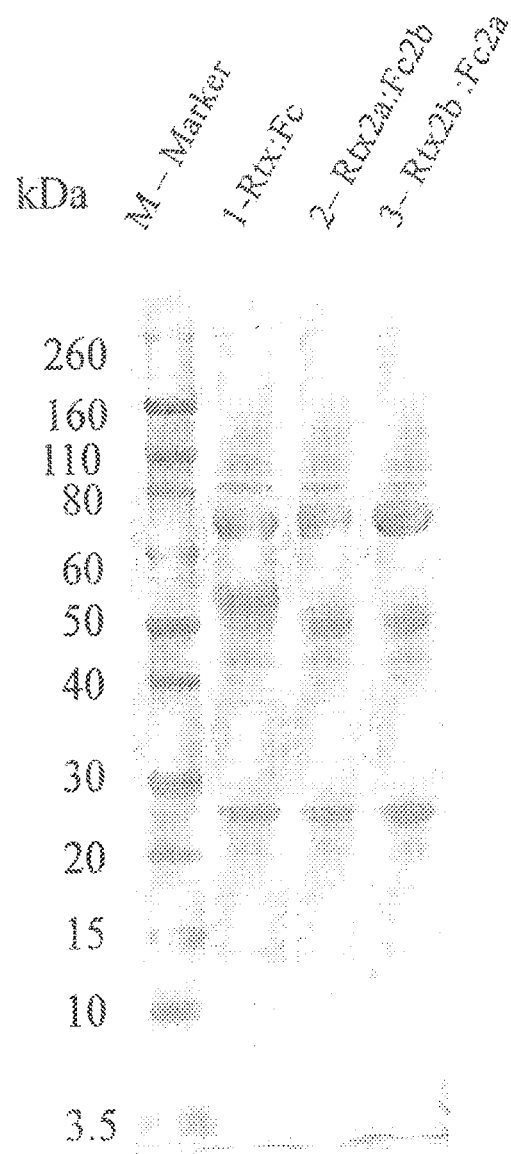

FIG. 7 shows a reduced SDS-PAGE gel of wild-type and engineered IgM Fc pairs 1a and 2b, where the designations are the same as in FIG. 6.

Figure 8:
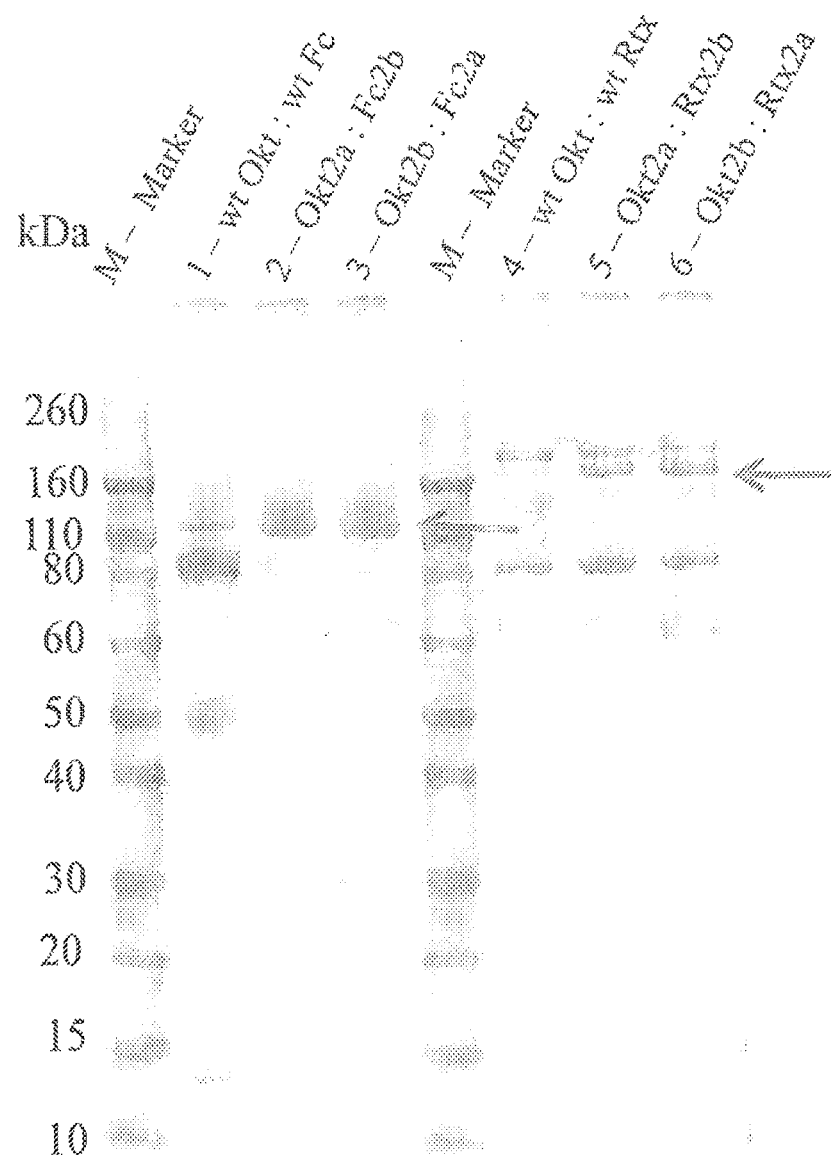

FIG. 8 shows a non-reduced SDS-PAGE gel of wild-type and engineered IgM Fc pairs:

Lane 1: wild-type Okt:Fc. Okt, composed of OKT3 (anti-CD3 antibody) scFv fused with CM2 to CM4 of human μ chain.

Lane 2: a mixture of Okt2a:Fc2b, where Okt2a is composed of OKT3 (anti-CD3 antibody) scFv fused with CM2 to CM4 of human μ chain with C291S, T350Y, T354E, and I397E mutations and tail piece deletion, where the amino acid coordinates refer to the human IgM heavy chain constant region of SEQ ID NO: 33;

Lane 3: a mixture of Okt2b:Fc2a, where Okt2b is composed of OKT3 (anti-CD3 antibody) scFv fused with CM2 to CM4 of human μ chain with C291S, L352S, T354K, H395V, and I397K mutations and tail piece deletion, where the amino acid coordinates refer to the human IgM heavy chain constant region of SEQ ID NO: 33. Arrow indicates heterodimer.

Lanes 4-6: Wild-type Okt:Rtx combination; engineered Okt2a:Rtx2b combination; and Okt2b:Rtx2a combination, where Rtx2a is composed of a μ chain for chimeric Rituxan (anti-CD20) Vh region fused with CM1 to CM4 of human μ chain with C291S, T350Y, T354E, and I397E mutations and tail piece deletion, and Rtx2b is composed of a μ chain for chimeric Rituxan (anti-CD20) Vh region fused with CM1 to CM4 of human mu chain with C291S, L352S, T354K, H395V, and I397K mutations and tail piece deletion, where the amino acid coordinates refer to the human IgM heavy chain constant region of SEQ ID NO: 33. Arrow indicates the heterodimer.

Figure 9:
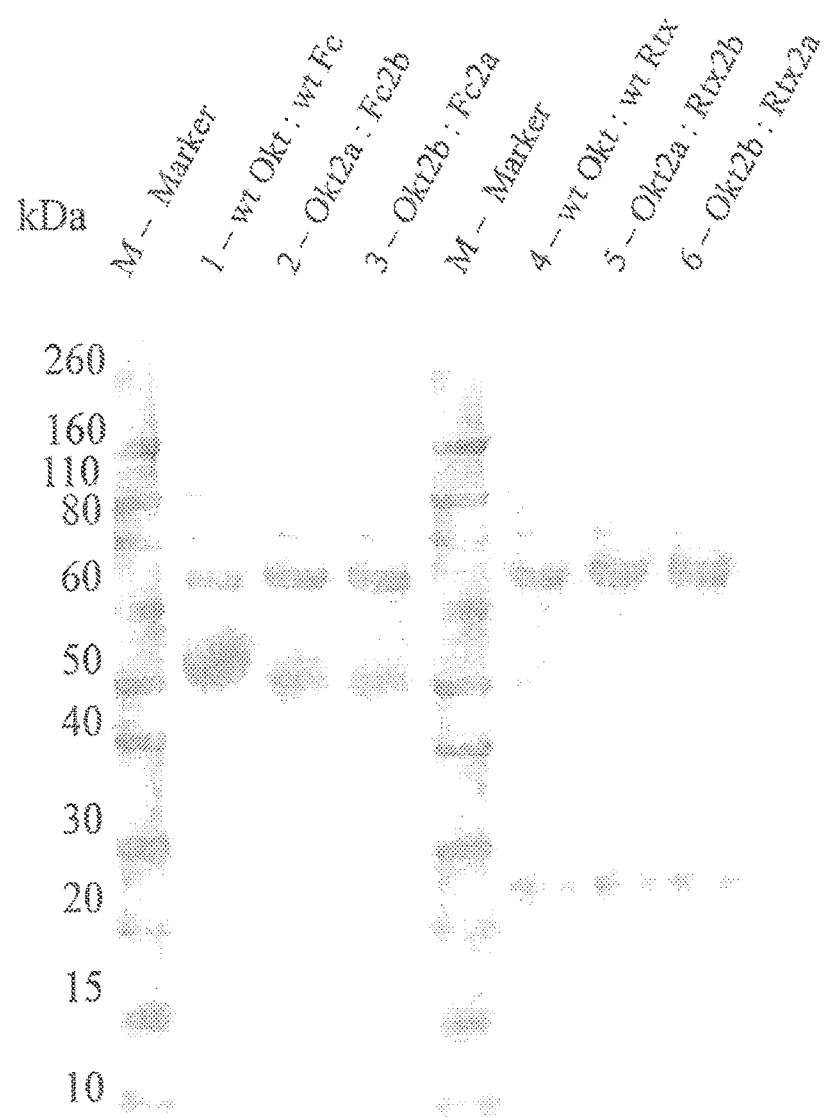

FIG. 9 shows reduced samples on SDS-PAGE gel of 293F cell transfectants of the same constructs as shown in FIG. 8.

Figure 10:

FIG. 10 illustrates how four salt bridges in the Cμ3 region stabilize two neighboring (A.B)μ chains around a disulfide bridge in a multi-specific binding molecule of the present invention.

FIGS. 11A-11H (Table A) list human IgM CM4 domain interface residues in knobs-holes positions and for potential charge introductions. The amino acid coordinates refer to the human IgM heavy chain constant region of SEQ ID NO: 33.

FIG. 12 (Table B) list human IgM CM4 domain interface residues for potential charge swaps. The amino acid coordinates refer to the human IgM heavy chain constant region of SEQ ID NO: 33.

FIG. 13 (Table C) list human IgM CM2 domain interface residues for potential charge introductions. The amino acid coordinates refer to the human IgM heavy chain constant region of SEQ ID NO: 33.

Figure 14B:
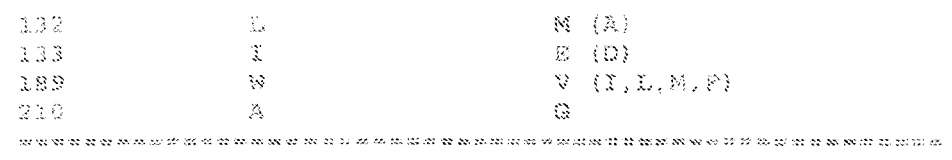

FIGS. 14A-14B (Table D) list human IgM CM2 domain interface residues in knobs-holes positions. The amino acid coordinates refer to the human IgM heavy chain constant region of SEQ ID NO: 33.

FIG. 15 (Table E) list human IgM CM2 domain interface residues for potential charge swaps. The amino acid coordinates refer to the human IgM heavy chain constant region of SEQ ID NO: 33.

FIG. 16A-16B (Table F) list human IgM CM2, CM3 and CM4 domain interface residues for charge exchanges. The amino acid coordinates refer to the human IgM heavy chain constant region of SEQ ID NO: 33.

DETAILED DESCRIPTION OF THE INVENTION

I. Definitions

The term "antibody" includes monoclonal antibodies (including full length antibodies which have an immunoglobulin Fc region), single-chain molecules, as well as antibody fragments (e.g., Fab, F(ab')$_2$, and Fv). The term "immunoglobulin" (Ig) is used interchangeably with "antibody" herein. The basic 4-chain antibody unit is a heterotetrameric glycoprotein composed of two identical light (L) chains and two identical heavy (H) chains.

In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain at its other end. The $V_L$ is aligned with the $V_H$ and the $C_L$ is aligned with the first constant domain of the heavy chain ($C_{H1}$). Particular amino acid residues are believed to form an interface between the light chain and heavy chain variable domains. The pairing of a $V_H$ and $V_L$ together forms a single antigen-binding site.

IgM forms polymers where multiple immunoglobulins are covalently linked together with disulfide bonds. IgM mostly exists as a pentamer but also as a hexamer and therefore contains 10 or 12 antigen binding sites. The pentameric form optionally contains an additional polypeptide, called the J chain, but can also be made in the absence of J chain. The pentameric IgM molecule has a molecular weight of approximately 970 kDa. Due to its polymeric nature, IgM possesses high avidity and is particularly effective in complement activation. Unlike in IgG, the heavy chain in IgM monomers is composed of one variable and four constant domains. The IgM constant domains are designated herein as CM1 or Cμ1, CM2 or Cμ2, CM3 or Cμ3, and CM4 or Cμ4, wherein the "CM" and Cμ" designations are used interchangeably.

IgA antibodies exist in a monomeric form but can also polymerize. In their secretory form IgA comprise from 2-5 of the basic 4-chain units linked by a J chain and a secretory component.

IgE exists in monomeric form, and has four constant domains, which are referred to as CE1, CE2, CE3 and CE4 in the present application.

The L chain from any vertebrate species can be assigned to one of two clearly distinct types, called kappa (κ) and lambda (λ), based on the amino acid sequences of their constant domains.

Some types of antibodies can further be divided into various sub-classes: IgG1, IgG2, IgG3, IgG4, IgA1 and IgA2.

For further details of the structure and properties of the different classes of antibodies, see e.g., Basic and Clinical Immunology, 8th Edition, Daniel P. Stites, Abba I. Terr and Tristram G. Parslow (eds), Appleton & Lange, Norwalk, Conn., 1994, page 71 and Chapter 6.

Unless stated otherwise, the term "antibody" specifically includes native human and non-human IgG1, IgG2, IgG3, IgG4, IgE, IgA, IgD and IgM antibodies, including naturally occurring variants. Thus, for example, the human IgM sequence presented as SEQ ID NO: 33 is encoded by the genomic sequence available under GenBank Accession Number X14940.1 (variant nucleotide sequences available under GenBank Accession Numbers X57331.1, and J00260.1 (replaced by AH005277.2)), while amino acid variants have been reported as GenBank CAB37838.1, CAC20458.1, and AFM37312.1.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) *Nature* 256:495, or may be made by recombinant DNA methods (see, e.g., U.S. Pat. No. 4,816,567). The "monoclonal antibodies" may also be isolated from phage antibody libraries using the techniques described in Clackson et al. (1991) *Nature* 352:624-628 and Marks et al. (1991) *J. Mol. Biol.* 222:581-597, for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al. (1984) *Proc. Natl. Acad. Sci. USA* 81:6851-6855).

"Humanized" forms of non-human (e.g., murine) antibodies are antibodies which contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are also replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al. (1986) *Nature* 321:522-525; Riechmann et al. (1988) *Nature* 332:323-329; and Presta (1992) *Curr. Op. Struct. Biol.* 2:593-596.

A "species-dependent antibody" is one which has a stronger binding affinity for an antigen from a first mammalian species than it has for a homologue of that antigen from a second mammalian species. Normally, the species-dependent antibody "binds specifically" to a human antigen (i.e. has a binding affinity ($K_d$) value of no more than about $1\times10^{-7}$ M, preferably no more than about $1\times10^{-8}$ M and most preferably no more than about $1\times10^{-9}$ M) but has a binding affinity for a homologue of the antigen from a second nonhuman mammalian species which is at least about 50 fold, or at least about 500 fold, or at least about 1000 fold, weaker than its binding affinity for the human antigen. The species-dependent antibody can be any of the various types of antibodies as defined above, but preferably is a humanized or human antibody.

As used herein, "antibody mutant" or "antibody variant" refers to an amino acid sequence variant of a reference antibody wherein one or more of the amino acid residues of the reference antibody have been modified. The reference antibody can, for example, be a native antibody but also a known variant of a native antibody. Such mutants necessarily have less than 100% sequence identity or similarity with the reference antibody. In a preferred embodiment, the antibody mutant will have an amino acid sequence having at least 75% amino acid sequence identity or similarity with the amino acid sequence of either the heavy or light chain variable domain of the reference antibody, more preferably at least 80%, more preferably at least 85%, more preferably at least 90%, and most preferably at least 95%. Identity or similarity with respect to this sequence is defined herein as the percentage of amino acid residues in the candidate sequence that are identical (i.e same residue) or similar (i.e. amino acid residue from the same group based on common side-chain properties) with the reference antibody residues, after aligning the sequences and introducing gaps, if necessary, to achieve the maximum percent sequence identity. None of N-terminal, C-terminal, or internal extensions, deletions, or insertions into the antibody sequence outside of the variable domain shall be construed as affecting sequence identity or similarity.

An "isolated" bispecific or multi-specific binding molecule, such as bispecific or multi-specific antibody, herein is one which has been identified and separated and/or recovered from a component of its natural environment in a recombinant host cell. Contaminant components of its natural environment are materials which would interfere with diagnostic or therapeutic uses for the molecule, e.g. antibody, and may include enzymes, hormones, and other proteinaceous or nonproteinaceous solutes, as well as undesired byproducts of the production, such as, for example, monospecific binding units (AA and/or BB in the case of a bispecific molecule comprising AB binding units), or molecules, with less than five bispecific binding units. In preferred embodiments, the bispecific binding molecule, such as antibody, will be purified (1) to greater than 95% by weight, or greater than 98% by weight, or greater than 99% by weight, as determined by SDS-PAGE or SEC-HPLC methods, (2) to a degree sufficient to obtain at least 15 residues of N-terminal or internal amino acid sequence by use of a amino acid sequencer, or (3) to homogeneity by SDS-PAGE under reducing or non-reducing conditions using Coomassie blue or, preferably, silver stain. Ordinarily, an isolated multi-specific, e.g. bispecific binding molecule, e.g. antibody, will be prepared by at least one purification step.

The term "specific binding" or "specifically binds to" or is "specific for" refers to the binding of a binding molecule, such as an antibody, to a target molecule, e.g., a particular polypeptide or an epitope on a particular polypeptide, peptide, or other target (e.g. a glycoprotein target), and means binding that is measurably different from a non-specific interaction (e.g., a non-specific interaction may be binding to bovine serum albumin or casein). Specific binding can be measured, for example, by determining binding of antibody to a target molecule compared to binding of antibody to a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about 200 nM, alternatively at least about 150 nM, alternatively at least about 100 nM, alternatively at least about 60 nM, alternatively at least about 50 nM, alternatively at least about 40 nM, alternatively at least about 30 nM, alternatively at least about 20 nM, alternatively at least about 10 nM, alternatively at least about 8 nM, alternatively at least about 6 nM, alternatively at least about 4 nM, alternatively at least about 2 nM, alternatively at least about 1 nM, or greater. In certain instances, the term "specific binding" refers to binding where a molecule binds to a particular polypeptide or epitope on a particular polypeptide without substantially binding to any other polypeptide or polypeptide epitope.

"Binding affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). For example, the Kd can be about 200 nM, 150 nM, 100 nM, 60 nM, 50 nM, 40 nM, 30 nM, 20 nM, 10 nM, 8 nM, 6 nM, 4 nM, 2 nM, 1 nM, or stronger. Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art.

As used herein, the "Kd" or "Kd value" refers to a dissociation constant measured by a technique appropriate for the antibody and target pair, for example using surface plasmon resonance assays, for example, using a BIAcore™-2000 or a BIAcore™-3000 (BIAcore, Inc., Piscataway, N.J.) at 25° C. with immobilized antigen CM5 chips at about 10 response units (RU).

The term "bispecific binding unit" is used herein to refer to a molecule comprising a pair of IgM heavy chain constant region polypeptides each comprising at least a CM4 domain, and each conjugated to a binding region to a different binding target. Preferably, the conjugation is by fusion, preferably to the N-terminus of the IgM heavy chain constant region polypeptide sequence. The term "bispecific binding unit" specifically encompasses, but is not limited to, a "bispecific IgM antibody binding unit," as hereinafter defined. The binding molecules of the present invention have a penta- or hexameric ring structure and comprise five or six bispecific binding units.

The terms "conjugate," "conjugated," and "conjugation" refer to any and all forms of covalent or non-covalent linkage, and include, without limitation, direct genetic or chemical fusion, coupling through a linker or a cross-linking agent, and non-covalent association.

The term "bispecific IgM antibody binding unit" is used in the broadest sense and specifically covers a pair of IgM antibody heavy chain constant region polypeptides, comprising at least a CM4 constant domain, fused to a variable domain sequence ($V_H$), each variable domain sequence binding to a different target, with or without associated antibody light chain variable domain ($V_L$) sequences. In one embodiment, the bispecific IgM antibody comprises two $V_H V_L$ antigen binding regions, each capable of binding to a different epitope on one antigen or epitopes on two different antigens. The bispecific IgM antibody binding units can be full length from a single species, or be chimerized or humanized. The bispecific IgM antibodies of the present invention have a penta- or hexameric ring structure comprising five or six bispecific IgM binding units.

A "full length IgM antibody heavy chain" is a polypeptide consisting in N-terminal to C-terminal direction of an antibody heavy chain variable domain (VH), an antibody constant heavy chain constant domain 1 (CM1 or Cμ1), an antibody heavy chain constant domain 2 (CM2 or Cμ2), an antibody heavy chain constant domain 3 (CM3 or Cμ3), and an antibody heavy chain constant domain 4 (CM4 or Cμ4). The bispecific full length IgM antibodies according to the invention comprise five or six monomers (binding units), each with two antigen binding sites, which specifically bind to two different binding targets (epitopes). The C-terminus of the heavy or light chain of the full length antibody denotes the last amino acid at the C-terminus of the heavy or light chain. The N-terminus of the heavy or light chain of the full length antibody denotes the first amino acid at the N-terminus of the heavy or light chain.

The term "valent" as used herein denotes the presence of a specified number of binding sites in an antibody. As such, the terms "bivalent", "tetravalent", and "hexavalent" denote the presence of two binding sites, four binding sites, and six binding sites, respectively. In the bispecific IgM antibodies according to the invention each binding unit is bivalent. Accordingly, the bispecific IgM antibodies herein have 10 or 12 valencies. The definition similarly applies to binding molecules that are non-antibodies.

The term "epitope" includes any molecular determinant capable of specific binding to an antibody. In certain embodiments, epitope determinant include chemically active surface groupings of molecules such as amino acids, sugar side chains, phosphoryl, or sulfonyl, and, in certain embodiments, may have specific three dimensional structural characteristics, and or specific charge characteristics. An epitope is a region of an antigen that is bound by an antibody. A "binding region" is a region on a target bound by a binding molecule.

"Polyepitopic specificity" refers to the ability to specifically bind to two or more different epitopes on the same or different target(s). "Monospecific" refers to the ability to bind only one epitope. According to one embodiment the bispecific IgM antibody binds to each epitope with an affinity of at least $10^{-7}$M, or $10^{-8}$M or better.

The term "target" is used in the broadest sense and specifically includes polypeptides, nucleic acids, carbohydrates, lipids, and other molecules with biological function as they exist in nature. The "target" may, for example, be a cell, wherein the bispecific binding units target two different cell types, different subpopulations of the same cell type (e.g. different B-cell populations) or two different entities on a single cell.

An "antigen-binding site" or "antigen-binding region" of an antibody of the present invention typically contains six complementarity determining regions (CDRs) which contribute in varying degrees to the affinity of the binding site for antigen. There are three heavy chain variable domain CDRs (CDRH1, CDRH2 and CDRH3) and three light chain variable domain CDRs (CDRL1, CDRL2 and CDRL3). The extent of CDR and framework regions (FRs) is determined by comparison to a compiled database of amino acid sequences in which those regions have been defined according to variability among the sequences and/or structural information from antibody/antigen complexes. Also included within the scope of the invention are functional antigen binding sites comprised of fewer CDRs (i.e., where binding specificity is determined by three, four or five CDRs). Less than a complete set of 6 CDRs may be sufficient for binding to some binding targets. Thus, in some instances, the CDRs of a VH or a VL domain alone will be sufficient. Furthermore, certain antibodies might have non-CDR-associated binding sites for an antigen. Such binding sites are specifically included within the present definition.

The term "interface", as used herein, is used to refer to a region, which comprises those "contact" amino acid residues (or other non-amino acid groups such as, for example, carbohydrate groups,) in a first IgM heavy chain constant region which interact with one or more "contact" amino acid residues (or other non-amino acid groups) in a second IgM heavy chain constant region.

The term "asymmetric interface" is used to refer to an interface (as hereinabove defined) formed between two antibody chains, such as a first and a second IgM heavy chain constant region and/or between an IgM heavy chain constant region and its matching light chain, wherein the contact residues in the first and the second chains are different by design, comprising complementary contact residues. The asymmetric interface can be created by knobs/holes interactions and/or salt bridges coupling (charge swaps) and/or other techniques known in the art, such as for example, by the CrossMab approach for coupling a μ heavy chain to its matching light chain.

A "cavity" or "hole" refers to at least one amino acid side chain which is recessed from the interface of the second polypeptide and therefore accommodates a corresponding protuberance ("knob") on the adjacent interface of the first polypeptide. The cavity (hole) may exist in the original interface or may be introduced synthetically (e.g. by altering nucleic acid encoding the interface). Normally, nucleic acid encoding the interface of the second polypeptide is altered to encode the cavity. To achieve this, the nucleic acid encoding at least one "original" amino acid residue in the interface of the second polypeptide is replaced with DNA encoding at least one "import" amino acid residue which has a smaller side chain volume than the original amino acid residue. It will be appreciated that there can be more than one original and corresponding import residue. The upper limit for the number of original residues which are replaced is the total number of residues in the interface of the second polypeptide. The preferred import residues for the formation of a cavity are usually naturally occurring amino acid residues and are preferably selected from alanine (A), serine (S), threonine (T), valine (V) and glycine (G). Most preferred amino acid residues are serine, alanine or threonine, most preferably alanine. In the preferred embodiment, the original residue for the formation of the protuberance has a large side chain volume, such as tyrosine (Y), arginine (R), phenylalanine (F) or tryptophan (W).

An "original" amino acid residue is one which is replaced by an "import" residue which can have a smaller or larger side chain volume than the original residue. The import amino acid residue can be a naturally occurring or non-naturally occurring amino acid residue, but preferably is the former.

By "non-naturally occurring" amino acid residue is meant a residue which is not encoded by the genetic code, but which is able to covalently bind adjacent amino acid residue(s) in the polypeptide chain. Examples of non-naturally occurring amino acid residues are norleucine, ornithine, norvaline, homoserine and other amino acid residue analogues such as those described in Ellman et al., Meth. Enzym. 202:301-336 (1991), for example. To generate such non-naturally occurring amino acid residues, the procedures of Noren et al. Science 244: 182 (1989) and Ellman et al., supra can be used. Briefly, this involves chemically activating a suppressor tRNA with a non-naturally occurring amino acid residue followed by in vitro transcription and translation of the RNA. The methods of the current invention, in certain embodiments, involve replacing at least one original amino acid residue in an IgM heavy chain, but more than one original residue can be replaced. Normally, no more than the total residues in the interface of the first or second polypeptide will comprise original amino acid residues which are replaced. The preferred original residues for replacement are "buried". By "buried" is meant that the residue is essentially inaccessible to solvent. The preferred import residue is not cysteine to prevent possible oxidation or mispairing of disulfide bonds.

The protuberance is "positionable" in the cavity which means that the spatial location of the protuberance and cavity on the interface of the first polypeptide and second polypeptide respectively and the sizes of the protuberance and cavity are such that the protuberance can be located in the cavity without significantly perturbing the normal association of the first and second polypeptides at the interface. Since protuberances such as Tyr, Phe and Trp do not typically extend perpendicularly from the axis of the interface and have preferred conformations, the alignment of a protuberance with a corresponding cavity relies on modeling the protuberance/cavity pair based upon a three-dimensional structure such as that obtained by X-ray crystallography or nuclear magnetic resonance (NMR). This can be achieved using widely accepted techniques in the art, including techniques of molecular modeling.

By "original nucleic acid" is meant the nucleic acid encoding a polypeptide of interest which can be "altered" (i.e. genetically engineered or mutated) to encode a protuberance or cavity. The original or starting nucleic acid may be a naturally occurring nucleic acid or may comprise a nucleic acid which has been subjected to prior alteration (e.g. a humanized antibody fragment). By "altering" the nucleic acid is meant that the original nucleic acid is mutated by inserting, deleting or replacing at least one codon encoding an amino acid residue of interest. Normally, a codon encoding an original residue is replaced by a codon encoding an import residue. Techniques for genetically modifying a DNA in this manner have been reviewed in Mutagenesis: a Practical Approach, M. J. McPherson, Ed., (IRL Press, Oxford, UK. (1991), and include site-directed mutagenesis, cassette mutagenesis and polymerase chain reaction (PCR) mutagenesis, for example.

The protuberance or cavity can be "introduced" into the interface of the first or second polypeptide by synthetic means, e.g. by recombinant techniques, in vitro peptide synthesis, those techniques for introducing non-naturally occurring amino acid residues previously described, by enzymatic or chemical coupling of peptides or some combination of these techniques. According, the protuberance or cavity which is "introduced" is "non-naturally occurring" or "non-native", which means that it does not exist in nature or in the original polypeptide (e.g. a humanized monoclonal antibody).

Preferably the import amino acid residue for forming the protuberance has a relatively small number of "rotamers" (e.g. about 3-6). A "rotamer" is an energetically favorable conformation of an amino acid side chain. The number of rotamers for the various amino acid residues are reviewed in Ponders and Richards, J. Mol. Biol. 193: 775-791 (1987).

The term "host cell" as used in the current application denotes any kind of cellular system which can be engineered to generate the antibodies according to the current invention. In one embodiment Chinese hamster ovary (CHO) cells are used as host cells.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included.

A nucleic acid is "operably linked" when it is placed in a functional relationship with another nucleic acid sequence. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

DETAILED DESCRIPTION

IgM is the first immunoglobulin produced by B cells in response to stimulation by antigen, and is present at around 1.5 mg/ml in serum with a half-life of 5 days. IgM is a pentameric or hexameric molecule. Just as IgG, IgM monomers consist of two light and two heavy chains. However, while IgG contains three heavy chain constant domains (CH1, CH2 and CH3), the heavy (μ) chain of IgM additionally contains a fourth constant domain (CH4), similarly to the c heavy chains in IgE. This extra constant domain is located in place of the IgG and IgA proline-rich hinge region that is responsible for the rotational flexibility of the antigen-binding Fab domains relative to the Fc domain of IgG and IgA antibodies.

Five IgM monomers form a complex with an additional small polypeptide chain (the J chain) to form a native IgM molecule. The J chain is considered to facilitate polymerization of μ chains before IgM is secreted from antibody-producing cells. While crystallization of IgM has proved to be notoriously challenging, Czajkowsky and Shao (PNAS 106(35):14960-14965, 2009) recently published a homology-based structural model of IgM, based on the structure of the IgE Fc domain and the known disulfide pairings. The authors report that the human IgM pentamer is a mushroom-shaped molecule with a flexural bias.

In a natural penta- or hexameric IgM antibody molecule all heavy (μ) chains are identical and the light chains are identical as well. The present invention allows the production of IgM molecules in which two μ chains are different from each other.

In one aspect, the present invention concerns bispecific binding molecules with binding specificities to two different binding regions, having a penta- or hexameric structure, formed by five or six bispecific binding units, wherein each of such bispecific binding units has the same two binding specificities and comprises a first chain comprising at least a CM4 domain of an IgM heavy chain constant region conjugated to a first binding region to a first binding target, and a second chain comprising at least a CM4 domain of an IgM heavy chain constant region and a second binding region to a second binding target, wherein the first and second binding targets are different, and wherein the first and second chains are assembled to create a bispecific binding unit as a result of an asymmetric interface created between their respective IgM heavy chain constant regions.

In various embodiments, the IgM heavy chain constant regions additionally comprise one or both of the CM2 and CM3 domains or fragments thereof, and potentially other IgM heavy chain constant domain sequences. In one embodiment, the binding molecules of the present invention contain a complete IgM heavy (μ) chain constant domain, with one or more modifications to create an asymmetric interface between two heavy chains.

In order to generate an IgM molecule with two different μ heavy chains (chains A and B), a solution must be found for coupling the two matching μ heavy chains (A and B) with two different binding specificities to each other. In addition, if a light chain is needed to form a binding region, a solution must be found to couple each heavy chain with its matching light chain to provide the desired binding specificity.

The coupling can be achieved by salt bridge pairs charge switching (also referred to as charge swaps or charge reversals) between certain residues and/or by creating knobs-holes interactions between the two chains. The heavy chains can also be paired with their matching light chains by using the CrossMab technique. The different approaches can also be combined in order to achieve an optimal result.

In another aspect, the present invention concerns multi-specific binding molecules with binding specificities to two or more different binding targets, having a penta- or hexameric structure. The invention includes binding molecules comprising five or six monospecific binding units, where (i) each of the monospecific binding units comprises two IgM heavy chain constant regions each comprising at least a Cμ3 and Cμ4 domain conjugated to a binding region to a binding target, (ii) at least two of the monospecific binding units bind to different binding target. The invention further includes binding molecules comprising five or six bispecific binding units, where (i) each of the bispecific binding units comprises two IgM heavy chain constant regions each comprising at least a Cµ3 and Cµ4 domain conjugated to a binding region to a binding target, and (ii) at least two of the bispecific binding units bind to different binding targets. In a particular embodiment, the binding molecules are multi-specific IgM antibodies.

In various embodiments, the IgM heavy chain constant regions additionally comprise a Cµ2 domain or a fragment thereof, and potentially other IgM heavy chain constant domain sequences. In one embodiment, the binding molecules of the present invention contain a complete IgM heavy (µ) chain constant domain, with one or more modifications to create an asymmetric interface between two heavy chains.

In the multi-specific binding molecules of the present invention which contain at least one bispecific binding unit, in order to generate an IgM molecule with two different µ heavy chains (chains A and B), a solution must be found for coupling the two matching µ heavy chains (A and B) with two different binding specificities to each other via an internal asymmetric interface. In addition, if a light chain is needed to form a binding region, a solution must be found to couple each heavy chain with its matching light chain to provide the desired binding specificity.

In addition, a solution must be found to create an external asymmetric interface between the heavy chain constant regions of the neighboring monospecific binding units that bind to different binding targets.

Techniques for creating internal and external asymmetric interfaces include, without limitation, salt bridge pairs charge switching (also referred to as charge swaps or charge reversals) between certain residues and creation of knobs-holes interactions between two chains. The heavy chains can also be paired with their matching light chains by using the CrossMab technique. The different approaches can also be combined in order to achieve an optimal result.

1. Knobs-into-Holes Technique

To improve the yields of the penta- or hexameric bispecific or multi-specific binding molecules of the present invention, the IgM heavy chain constant regions, e.g. the CM4, CM2 and/or CM3 domains, can be altered by the "knob-into-holes" technique which is described in detail with several examples in e.g. WO 96/027011, Ridgway, J., B., et al., Protein Eng 9 (1996) 617-621; and Merchant, A. M., et al., Nat Biotechnol 16 (1998) 677-681. In this method the interaction surfaces of two IgM heavy chain constant domains are altered to increase the heterodimerization of two heavy chains with different binding specificities and/or between a heavy chain and its matching light chain. Each of the two heavy chain domains, e.g. CM4-CM4, CM2-CM2 and/or CM2-CM3-CM4/CM2-CM3-CM4 can be the "knob", while the other is the "hole". The introduction of a disulfide bridge stabilizes the heterodimers (Merchant, A. M., et al., Nature Biotech 16 (1998) 677-681; Atwell, S., et al., J. Mol. Biol. 270 (1997) 26-35) and increases the yield. Similarly, the matching heavy and light chains can be coupled to each other by this technique Zhu, Z.; Presta, L. G.; Zapata, G.; Carter, P. *Remodeling domain interfaces to enhance heterodimer formation.* Prot. Sci. 6:781-788 (1997).

Following this approach, in the case of bispecific IgM binding molecules within the original interface of the CH4, CH2 and/or CH3 domains of one heavy chain that meets the original interface of the corresponding domain of the other heavy chain within the bispecific IgM binding molecule (e.g. antibody), an amino acid residue may be replaced with an amino acid residue having a larger side chain volume, thereby creating a protuberance within the interface, which is positionable in a cavity within the interface of the corresponding domain in the other IgM heaving chain constant region. Similarly, the second IgM heavy chain may be altered, by replacing an amino acid residue within the interface with a corresponding domain in the constant region of the first IgM heavy chain, with an amino acid residue having a smaller side chain volume, thereby creating a hole (cavity) within the interface between the two heavy chain regions.

Human IgM CM4 and CM2 domain interface residues in knobs-holes positions are shown in Tables A and D. The Tables identify the native residue at the indicated positions of the IgM heavy chain constant region (SEQ ID NO: 33), with the CM4 sequence shown in FIG. 4D and the CM2 sequence shown in FIG. 4B, respectively, following the numbering shown in those Figures, as well as the potential mutations that can be used to create knobs-holes pairs. Thus, for example, in the CM4 domain the native threonine (T) residue in position 350 of SEQ ID NO: 33 may be mutated into tyrosine (Y) to create a knob, which can be combined with any combinations of the potential mutations listed for residues 352, 393 and 395 of SEQ ID NO: 33 of the native CM4 sequence (Set #1). Additional mutations at positions 254 and 397 of SEQ ID NO: 33, that can be optionally combined with Set #1 are shown in Set #2 and Set #3). Similarly, Set #4 exemplifies knobs mutations at positions 350 and 395 of SEQ ID NO: 33 in combination with hole mutations at one or more of positions 352, 393, 395, and 397 of SEQ ID NO: 33. Additional mutations for combination with Set#4 are listed in Set #5 and Set #6. The rest of Table A can be read in a similar way. Some of the sets also include charge introductions, i.e. changes from a non-charged residue to a charged residue (similarly to Table C discussed below).

It is emphasized that the listed knobs-holes mutations in Sets #1-30 can be used in various combinations as set forth in Table A. Furthermore, the listed mutations can be combined with other knobs-holes and/or charge swap and/or charge introduction mutations listed in the rest of the Tables. Thus, one or more of the knobs-holes mutations set forth in Table A can be combined with one or more of the knobs-holes mutations shown in Table D, in any combination and/or with one or more of the charge swap/charge introduction mutations listed in Tables B, C, E and F, as discussed hereinbelow. Thus, one can select any set from Table A and mix it with any set from Table B, mixed with any set from Table C, etc., in any order or combination.

2. Salt Bridge Pairs Charge Switching (Charge Swapping)

Opposite charges attract and similar charges repel each other. The charge of an amino acid molecule is pH dependent and can be characterized by the pK values, which are determined for the alpha amino group (N), the alpha carboxy group (C) and the side chain for free amino acids. The local environment can alter the $pK_a$ of a side chain when the amino acid is part of a protein or peptide.

The charge properties of an amino acid molecule can also be characterized by the isoelectric point (pI), which is the pH at which the overall charge of the molecule is neutral. Since amino acids differ from each other in their side chains, the pI reflects differences in the pKs of the side chains.

Most amino acids (15/20) have a pI close to 6 so they are regarded as having neutral overall charge. Asp and Glu are negatively charged, and His, Lys, Arg are positively charged.

In the interface between two binding units in the mushroom-shaped IgM complex there are four salt bridges, above and below the disulfide bridge connecting the monomers. The residues involved in these interactions (Lys-238, Lys-268, Asp-293 and Asp294 of SEQ ID NO: 33) are the same in the two monomers, but their relative disposition in this interface is different, due to the asymmetry of the CM3 domains in the IgM Fc structure.

Positions and amino acid residues for charge swapping or charge introduction mutations are listed in Tables A, B, D, E, and F. As discussed above, or more of these mutations, or sets of mutations, can be combined with one or more sets of knobs-holes mutations to provide a desired asymmetric interface between two different IgM heavy chains and/or between an IgM heavy chain and its matching light chain.

Preferably, the asymmetric interface between two different IgM heavy chain constant regions is created by up to 8, such as, for example, 1-8, or 1-7, or 1-6, or 1-5, or 1-4, or 1-3, or 1-2 mutations in one IgM heavy chain, or 2-10, or 2-9, or 2-8, or 2-7, or 2-6, or 2-5, or 2-4, or 2-3 combined mutations in the two IgM heavy chains.

For multi-specific binding molecules herein, the external asymmetric interface is created by an alteration in the Cµ3 domain. In particular, to create an external asymmetric interface, a salt bridge is formed by pair-wise switches between oppositely charged amino acid residues in the Cµ3 domain. In various embodiments, the salt bridge providing the external asymmetric interface is formed by at least one pair-wise charged amino acid residue switch in the Cµ3-Cµ3 domains, which may, for example be K238↔D293 or K268↔D294 in the neighboring µ chains, where the amino acid coordinates refer to the human IgM heavy chain constant region of SEQ ID NO: 33.

3. CrossMab Technique

As discussed above, the knobs-into-holes technology or charge swapping enables heterodimerization of the antibody heavy chains. Correct association of the light chains and their cognate heavy chains can be achieved by exchange of heavy-chain and light-chain domains within the antigen binding fragment (Fab) of one half of the bispecific antibody binding unit. Crossover can occur as a crossover of the complete VH-CM and VL-CL domains, crossover of only the VH and VL domains. or the CM and CL domains within the one half of the bispecific binding unit of an IgM antibody. This "crossover" retains the antigen-binding affinity but makes the two arms so different that light-chain mispairing can no longer occur. For further details, in the context of IgG antibodies, see, for example, Schaeffer et al., (2011) *Proc Natl Acad Sci USA* 108(27): 11187-11192.

4. Production of Bispecific and Multi-Specific IgM Binding Molecules

The coding sequences of the heavy chains of the bispecific IgM antibody binding units, with the desired mutations (following the knobs-into-holes, charge swap and/or CrossMab technique) may be produced by introducing appropriate nucleotide changes into the antibody DNA, or by nucleotide synthesis. The antibodies can then be produced by recombinant means.

Methods for recombinant production are widely known in the state of the art and comprise protein expression in prokaryotic and eukaryotic cells with subsequent isolation of the antibody and usually purification to a pharmaceutically acceptable purity. For the expression of the antibodies in a host cell, nucleic acids encoding the respective modified heavy chains, and optionally light chains, are inserted into expression vectors by standard methods. Expression is performed in appropriate prokaryotic or eukaryotic host cells like CHO cells, NS0 cells, SP2/0 cells, HEK293 cells, COS cells, PER.C6 cells, yeast, or *E. coli* cells, and the antibody is recovered from the cells (supernatant or cells after lysis). General methods for recombinant production of antibodies are described, for example, in the review articles of Makrides, S. C., *Protein Expr. Purif* 17 (1999) 183-202; Geisse, S., et al., *Protein Expr. Purif* 8 (1996) 271-282; Kaufman, R. J. *Mot Biotechnol.* 16 (2000) 151-161; Werner, R. S., *Drug Res.* 48 (1998) 870-880.

The bispecific and multi-specific antibodies are suitably separated from the culture medium by conventional immunoglobulin purification procedures such as, for example, protein A-SEPHAROSE®, hydroxylapatite chromatography, gel electrophoresis, dialysis, or affinity chromatography.

Although due to its complex structure, the large scale production of recombinant IgM has been difficult, several recombinant production systems for IgM using non-lymphoid cells have been reported, including co-expression of the IgM heavy (H) and light (L) chains in C6 glioma cells, CHO cells, and HeLa cells. While the co-expression successfully resulted in the formation of polymer, the yields were typically low (see, e.g. WO89/01975 and Wood et al., J. Immunol. 145, 3011-3016 (1990) for expression in CHO cells), and the exact polymeric structure of the penta- or hexameric molecules could not be readily determined. Production of IgM in an immortalized human retina cell line expressing E1A and E1B proteins of an adenovirus is described in U. S. Application Publication No. 20060063234. Further details of the production of the bispecific IgM antibodies of the present invention are provided in the Example below.

The methods of the present invention will result in a composition comprising a bispecific or multi-specific IgM binding molecule, such as a bispecific or multi-specific IgM antibody, as the main component, in combination with various by-products of the manufacturing process, such as monospecific antibodies, antibody fragments, monomers, dimers, trimers, and/or tetramers of the bispecific binding unit, instead of the desired pentameric or hexameric structure. The compositions produced will generally contain at least about 70%, or at least about 75%, or at least about 80%, or at least about 85%, or at least about 90%, or at least about 92%, or at least about 95%, of the desired penta- or hexameric bispecific binding molecule, e.g. antibody, which will be further purified by methods known in the art to yield a product with a purity of at least about 90%, or at least about 95%, or at least about 98%, or at least about 99%, or at least about 99.5%, or at least about 99.9%.

5. Applications of the Bispecific and Multi-Specific IgM Binding Molecules

The bispecific and multi-specific IgM binding molecules, e.g. antibodies, of the present invention have widespread therapeutic and diagnostic applications.

In one embodiment, the bispecific binding molecules herein bind to two sites on the same soluble target, such as, for example, VEGF, TNFα, or IL6. The purpose may, for example, be antagonizing multiple sites on the protein and/or increasing the avidity to a given target.

In another embodiment, the bispecific or multi-specific binding molecules herein bind two or more sites on the same cell surface (receptor) target, such as EGFR or HER2 (ErbB2). Thus, for example, a bispecific or multi-specific binding molecule might target both the 4D5 and the 2C4 epitopes on a HER2 molecule. This approach may increase bio-potency and/or avidity to a given target.

In yet another embodiment, the bispecific or multi-specific binding molecules of the present invention bind two or more different soluble targets (globular proteins or peptides), e.g. TNFα and IL6, VEGFα and Ang2, or two cytokines. This approach might result in more complete blocking a specific pathway; blocking of the so called "cytokine storm," or coordinate an enzyme and its substrate, e.g. Factor IXa and Factor X.

In a further embodiment, the bispecific or multi-specific binding molecules herein may bind a soluble target and a cell surface receptor target, such as an angiogenic factor and neo-vascular specific receptor. The purpose of this approach may also be increased delivery and blockade at specific sites or tissues.

In a still further embodiment, the bispecific binding molecules herein are designed to bind two different cell surface receptor targets, such as, for example, HER2 (ErbB2) and HER3 (ErbB3). Similarly, the multi-specific binding molecules herein can be designed to bind two or more different cell surface receptor targets, such as, for example, HER1, HER2 (ErbB2) and HER3 (ErbB3). This may result in enhancing specificity and selectivity and/or in more complete blocking of a given pathway.

Bispecific and multi-specific binding molecules, such as antibodies, of the present invention may also be designed to bind one soluble target or cell surface receptor target and a long residence time target, such as, for example, TNFα and serum albumin, or VEGF and serum albumin. These molecules are expected to have longer circulating half-life than binding molecules without the albumin specificity.

In a further embodiment, the bispecific binding molecules herein may bind one soluble target and a matrix protein or a substrate, such as, for example, VEGFα and hyaluronic acid. Similarly, the multi-specific binding molecules herein may bind one or more soluble targets and one or more matrix proteins and/or substrates, such as, for example, VEGFα and hyaluronic acid. The resultant bi- or multi-specific binding molecules may find utility, for example, in anti-angiogenic therapy of ocular conditions, such as age-related macular degeneration (AMD), due to their increased residence time in the intraocular space.

Bispecific molecules, e.g. antibodies binding one soluble or receptor target, plus a transporter receptor (ie transferrin receptor), e.g. anti-EGFRvIII (mutant form with exon III deleted) found glioblastoma combined with anti-transferrin specificity, can find utility in antibody delivery across blood brain barrier.

Similarly, multi-specific molecules, e.g. antibodies binding one or more soluble or receptor targets, plus one or more transporter receptors (ie transferrin receptor), e.g. anti-EGFRvIII (mutant form with exon III deleted) found glioblastoma combined with anti-transferrin specificity, can find utility in antibody delivery across blood brain barrier.

6. Compositions, Pharmaceutical Compositions, and Methods of Treatment

In one aspect, the invention concerns compositions comprising purified bispecific or multi-specific IgM binding molecules, such as bispecific or multi-specific IgM antibodies herein. The compositions generally will contain at least about 80%, or at least about 85%, or at least about 90%, or at least about 92%, or at least about 95%, or at least about 98%, or at least about 99% of the desired bispecific or multi-specific IgM binding molecule, e.g. antibody. The composition may be a pharmaceutical composition, where the bispecific or multi-specific binding molecule, e.g. antibody, is in admixture with at least one pharmaceutically acceptable carrier.

A pharmaceutical composition of the present invention can be administered by a variety of methods known in the art. As will be appreciated by the skilled artisan, the route and/or mode of administration will vary depending upon the target disease or condition and the desired results. To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Pharmaceutical carriers include sterile aqueous solutions or dispersions and sterile powders for the extemporaneous preparation of sterile injectable solutions or dispersion. The use of such media and agents for pharmaceutically active substances is known in the art.

The compositions may also contain adjuvants such as preservatives, wetting agents, emulsifying agents and/or dispersing agents. Prevention of presence of microorganisms may be ensured both by sterilization procedures and by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The composition must be sterile and fluid to the extent that the composition is deliverable by syringe. In addition to water, the carrier preferably is an isotonic buffered saline solution.

The following examples, sequence listing and figures are provided to aid the understanding of the present invention, the true scope of which is set forth in the appended claims. It is understood that modifications can be made in the procedures set forth without departing from the spirit of the invention. Throughout the examples, where a mutation in an IgM heavy chain is referred to with the following formula: "X###Y," "X" refers to the native amino acid (single letter code), "###" refers to the coordinate in the wild-type human IgM constant region sequence presented herein as SEQ ID NO: 33, and "Y" refers to the mutated amino acid (single letter code).

All patent and scientific references cited throughout this disclosure are hereby expressly incorporated by reference herein.

Example 1

1. Generation of DNA Constructs with Designed Mutations

Materials and Methods a. DNA Construct Synthesis

All DNA constructs with designed mutations were synthesized by commercial vendors (Genewiz, Inc.), with compatible restriction sites at both ends for subcloning into respective expression vectors, using methods well known in the art.

b. Construction of Expression Vectors

The synthesized DNA constructs were re-suspended in Tris-EDTA buffer at 1 µg/ml. DNA (1 µg) was subjected to enzyme digestion and the synthesized gene was separated from the carrier plasmid DNA by electrophoresis. The digested DNA was ligated to pre-digested plasmid DNA (pFUSEss-CHIg-hM*03 for µ chain; pFUSE2ss-CLIg-hk for kappa chain, InvivoGen) by standard molecular biology techniques. The ligated DNA was transformed into competent bacteria and plated on LB plates with multiple selective antibiotics. Several bacterial colonies were picked and DNA preparations were made by standard molecular biology techniques. The prepared DNA was verified by sequencing. Only the bacterial clones with 100% match of DNA sequence with the designed DNA sequence were used for plasmid DNA preparation and subsequently for cell transfection.

c. µ Chains of Different Size

In order to demonstrate that two different µ chains with or without CM4 interaction interface mutation (A and B) were able to couple together, two sets of different sized µ chains were constructed with distinct molecular weights and ligand specificities.

i. The Rtx chain is composed of a µ chain for the chimeric anti-CD20 antibody Rituxan (Rituximab) Vh region fused with the CM1 region of human IgM antibody µ chain with a C291S mutation and tail piece deletion:

(SEQ ID NO: 1)
QVQLQQPGAELVKPGASVKMSCKASGYTFTSYNMHWVKQTPGRGL
EWIGAIYPGNGDTSYNQKFKGKATLTADKSSSTAYMQLSSLTSED
SAVYYCARSTYYGGDWYFNVWGAGTTVTVSSGSASAPTLFPLVSC
ENSPSDTSSVAVGCLAQDFLPDSITFSWKYKNNSDISSTRGFPSV
LRGGKYAATSQVLLPSKDVMQGTDEHVVCKVQHPNGNKEKNVPLP
VIAELPPKVSVFVPPRDGFFGNPRKSKLICQATGFSPRQIQVSWL
REGKQVGSGVTTDQVQAEAKESGPTTYKVTSTLTIKESDWLSQSM
FTCRVDHRGLTFQQNASSMCVPDQDTAIRVFAIPPSFASIFLTKS
TKLTCLVTDLTTYDSVTISWTRQNGEAVKTHTNISESHPNATFSA
VGEASISEDDWNSGERFTCTVTHTDLPSPLKQTISRPKGVALHRP
DVYLLPPAREQLNLRESATITCLVTGFSPADVFVQWMQRGQPLSP
EKYVTSAPMPEPQAPGRYFAHSILTVSEEEWNTGETYTCVVAHEA
LPNRVTERTVD

The Rtx chain has a calculated molecular weight about 60 kD (without glycosylation) and 66 kD (with 4 N-glycosylation sites) and is able to bind to CD20 positive B cells, such as Raji cells.

ii. The Fc chain comprises human IgM µ chain CM2 to CM4 regions, carrying a cMyc tag and having its tail piece replaced by 6His tag (SEQ ID NO: 18) and having a C291S mutation:

(SEQ ID NO: 2)
GSGSKVSVFVPPRDGFFGNPRKSKLICQATGFSPRQIQVSWLREG
KQVGSGVTTDQVQAEAKESGPTTYKVTSTLTIKESDWLSQSMFTC
RVDHRGLTFQQNASSMCVPDQDTAIRVFAIPPSFASIFLTKSTKL
TCLVTDLTTYDSVTISWTRQNGEAVKTHTNISESHPNATFSAVGE
ASISEDDWNSGERFTCTVTHTDLPSPLKQTISRPKGVALHRPDVY
LLPPAREQLNLRESATITCLVTGFSPADVFVQWMQRGQPLSPEKY
VTSAPMPEPQAPGRYFAHSILTVSEEEWNTGETYTCVVAHEALPN
RVTERTVDKSTGKGGGSEQKLISEEDLNSAVDHHHHHH

The Fc chain has a molecular weight about 39 kD (without glycosylation) and 43 kD (with 3 N-glycosylation sites) and is able to bind to anti-myc monoclonal antibody 9E4 or other anti-myc antibodies.

iii. The Okt chain is composed of a single chain Fv version of OKT3 (anti-CD3) fused with CM2 of human mu chain with C291S and tail piece deletion:

(SEQ ID NO: 3)
QVQLQQSGAELARPGASVKMSCKASGYTFTRYTMHWVKQRPGQGLE
WIGYINPSRGYTNYNQKFKDKATLTTDKSSSTAYMQLSSLTSEDSAVY
YCARYYDDHYSLDYWGQGTTLTVSSGGGGSGGGGSGGGGSQIVLTQS
PAIMSASPGEKVTMTCSASSSVSYMNWYQQKSGTSPKRWIYDTSKLAS
GVPAHFRGSGSGTSYSLTISGMEAEDAATYYCQQWSSNPFTFGSGTKL
EIKGSGSKVSVFVPPRDGFFGNPRKSKLICQATGFSPRQIQVSWLREGK
QVGSGVTTDQVQAEAKESGPTTYKVTSTLTIKESDWLSQSMFTCRVDH
RGLTFQQNASSMCVPDQDTAIRVFAIPPSFASIFLTKSTKLTCLVTDLTT
YDSVTISWTRQNGEAVKTHTNISESHPNATFSAVGEASISEDDWNSGER
FTCTVTHTDLPSPLLQTISRPKGVALHRPDVYLLPPAREQLNLRESATIT
CLVTGFSPADVFVQWMQRGQPLSPEKYVTSAPMPEPQAPGRYFAHSIL
TVSEEEWNTGETYTCVVAHEALPNRVTERTVD

The Okt chain has a calculated molecular weight about 61 kD without glycosylation and 67 kD including 4 N-glycosylation sites, and is able to bind to CD3 positive T cells.

d. Light Chain Coupling i. Native Chimeric Rituxan Kappa (κ) Chain (SEQ ID NO: 4)
QIVLSQSPAILSASPGEKVTMTCRASSSVSYIHWFQQKPGSSPKPWIYAT
SNLASGVPVRFSGSGSGTSYSLTISRVEAEDAATYYCQQWTSNPPTFGG
GTKLEIKRTVAAPSVFIFPPSDEQLKSGTASVVCLLNNFYRREAKVQWK
VDNALQSGNSQESVTEQDSKDSTYSLSSTLTLSKADYEKHKVYACEVT
HQGLSSPVTKSFNRGEC The kappa chain has a calculated molecular weight about 23 kD and is able to link to Rituxan IgM heavy chain.

e. Interface Mutations

Knobs and holes, electrostatic charge coupling were asymmetrically introduced into the CM3 interaction interface to maximize hetero-dimerization of two μ chains. Two pairs of CM3 interaction interface mutants were generated.

i. Fc1a is a human μ chain CH2 to CH4 region with C291S and T350Y mutations and tail piece deletion:

(SEQ ID NO: 5)
GSGSKVSVFVPPRDGFFGNPRKSKLICQATGFSPRQIQVSWLREGKQVG

SGVTTDQVQAEAKESGPTTYKVTSTLTIKESDWLSQSMFTCRVDHRGL

TFQQNASSMCVPDQDTAIRVFAIPPSFASIFLIKSTKLTCLVTDLTTYDS

VTISWTRQNGEAVKTHTNISESHPNATFSAVGEASISEDDWNSGERFTC

TVTHTDLPSPLKQTISRPKGVALHRPDVYLLPPAREQLNLRESATI*Y*CLV

TGFSPADVFVQWMQRGQPLSPEKYVTSAPMPEPQAPGRYFAHSILTVS

EEEWNTGETYTCVVAHEALPNRVTERTVDKSTGK

The Fc1a chain has a calculated molecular weight about 36 kD without glycosylation and 41 kD if 3 N-glycosylation sites are included.

ii. Fc1b is human μ chain CH2 to CH4 and with C291S, L352S and H395V mutations and tail piece deletion (SEQ ID NO: 6)
GSGSKVSVFVPPRDGFFGNPRKSKLICQATGFSPRQIQVSWLREGKQVG

SGVTTDQVQAEAKESGPTTYKVTSTLFIKESDWLSQSMTCRVDHRGL

TFQQNASSMCVPDQDTAIRVFAIPPSFASIFLTKSTKLTCLVTDLTTYDS

VTISWTRQNGEAVKTHTNISESHPNATFSAVGEASISEDDWNSGERFTC

TVTHTDLPSPLKQTISRPKGVALHRPDVYLLPPAREQLNLRESATITC*S*V

TGFSPADVFVQWMQRGQPLSPEKYVTSAPMPEPQAPGRYFA*V*SILTVS

EEEWNTGETYTCVVAHEALPNRVTERTVDKSTGK

The Fc1b chain has a calculated molecular weight about 36 kD without glycosylation and 41 kD including 3 N-glycosylation sites.

iii. Fc2a consists of a human μ chain CH2 to CH4 region with C291S, T350Y, T354E, and I397E mutations and tail piece deletion.

(SEQ ID NO: 7)
GSGSKVSVFVPPRDGFFGNPRKSKLICQATGFSPRQIQVSWLREGKQVG

SGVTTDQVQAEAKESGPTTYKVTSTLTIKESDWLSQSMFTCRVDHRGL

TFQQNASSMCVPDQDTAIRVFAIPPSFASIFLTKSTKLTCLVTDLTTYDS

VTISWTRQNGEAVKTHTNISESHPNATFSAVGEASISEDDWNSGERFTC

TVTHTDLPSPLKQTISRPKGVALHRPDVYLLPPAREQLNLRESATI*Y*CLV

*E*GFSPADVFVQWMQRGQPLSPEKYVTSAPMPEPQAPGRYFAHS*E*LTVS

EEEWNTGETYTCVVAHEALPNRVTERTVDKSTGK

The Fc2a chain has a calculated molecular weight of about 36 kD without glycosylation and 41 kD including 3 N-glycosylation sites.

iv. Fc2b is human μ chain CH2 to CH4 and with C291S, L352S, T354K, H395V, and I397K mutations and tail piece deletion.

(SEQ ID NO: 8)
GSGSKVSVFVPPRDGFFGNPRKSKLICQATGFSPRQIQVSWLREGKQVG

SGVTTDQVQAEAKESGPTTYKVTSTLTIKESDWLSQSMFTCRVDHRGL

TFQQNASSMCVPDQDTAIRVFAIPPSFASIFLTKSTKLTCLVTDLTTYDS

VTISWTRQNGEAVKTHTNISESHPNATFSAVGEASISEDDWNSGERFTC

TVTHTDLPSPLKQTISRPKGVALHRPDVYLLPPAREQLNLRESATITC*S*V

*K*GFSPADVFVQWMQRGQPLSPEKWTSAPMPEPQAPGRYFA*VS K*LTVS

EEEWNTGETYTCVVAHEALPNRVTERTVDKSTGK

The Fc2b chain has a calculated molecular weight of about 36 kD without glycosylation and 41 kD including 3 N-glycosylation sites.

f. Interface Mutations

Fc2a chain and Fc2b chain with knobs, holes, and electrostatic charge coupling were further linked to both Rituxan and the OKT3 (anti-CD3 antibody) scFv by molecular cloning for asymmetrically hetero-dimerization of two μ chains.

i. Rtx2a is composed of a μ chain for chimeric Rituxan (anti-CD20) Vh region fused with CM1 to CM4 of human μ chain with C291S, T350Y, T354E, and I397E mutations and tail piece deletion.

(SEQ ID NO: 9)
QVQLQQPGAELVKGASVKMSCKASGYTFTSYNMHWVKQTPGRGLE

WIGAIYPGNGDTSYNQKFKGKATLTADKSSSTAYMQLSSLTSEDSAVY

YCARSTYYGGDWYFNVWGAGTTVTVSSGSASAPTLFPLVSCENSPSDT

SSVAVGCLAQDFLPDSITFSWKYKNNSDISSTRGFPSVLRGGKYAATSQ

VLLPSKDVMQGTDEHVVCKVQHPNGNKEKNVPLPVIAELPPKVSVFVP

PRDGFFGNPRKSKLICQATGFSPRQIQVSWLREGKQVGSGVTTDQVQA

EAKESGPTTYKVTSTLTIKESDWLSQSMFTCRVDHRGLTFQQNASSMC

VPDQDTAIRVFAIPPSFASIFLTKSTKLTCLVTDLTTYDSVTISWTRQNG

EAVKTHTNISESHPNATFSAVGEASISEDDWNSGERFTCTVTHTDLPSPL

KQTISRPKGVALHRPDVYLLPPAREQLNLRESATI*Y*CLV*E*GFSPADVFV

QWMQRGQPLSPEKYVTSAPMPEPQAPGRYFAHS*E*LTVSEEEWNTGET

YTCVVAHEALPNRVTERTVDKSTGK

The Rtx2a chain has a calculated molecular weight of about 61 kD without glycosylation and 67 kD with 4 N-glycosylation sites.

ii. Rtx2b is composed of a μ chain for chimeric Rituxan (anti-CD20) Vh region fused with CM1 to CM4 of human mu chain with C291S, L352S, T354K, H395V, and I397K mutations and tail piece deletion.

(SEQ ID NO: 10)
QVQLQQPGAELVKPGASVKMSCKASGYTFTSYNMHWVKQTPGRGLE

WIGAIYPGNGDTSYNQKFKGKATLTADKSSSTAYMQLSSLTSEDSAVY

YCARSTYYGGDWYFNVWGAGTTVTVSSGSASAPTLFPLVSCENSPSDT

SSVAVGCLAQDFLPDSITFSWKYKNNSDISSTRGFPSVLRGGKYAATSQ

VLLPSKDVMQGTDEHVVCKVQHPNGNKEKNVPLPVIAELPPKVSVFVP

```
-continued
PRDGFFGNFRKSKLICQATGESPRQIQVSWLREGKQVGSGVTTDQVQA

EAKESGPTTYKVTSTLTIKESDWLSQSMFTCRVDHRGLTFQQNASSMC

VPDQDTAIRVFAIPPSFASIFLTKSTKLTCLVTDLTTYDSVTISWTRQNG

EAVKTHTNISESHPNATFSAVGEASISEDDWNSGERFTCTVTHTDLPSPL

KQTISRPKGVALHRPDVYLLPPAREQLNLRESATITCSVKGFSFADVFV

QWMQRGQPLSPEKYVTSAPMPEPQAPGRYFAVSKLTVSEEEWNTGET

YTCVVAHEALPNRVTERTVDKSTGK
```

The Rtx2b chain has a calculated molecular weight of about 61 kD without glycosylation and 67 kD including 4 N-glycosylation sites.

iii. Okt2a is composed of OKT3 (anti-CD3 antibody) scFv fused with CM2 to CM4 of human μ chain with C291S, T350Y, T354E, and I397E mutations and tail piece deletion.

```
                                          (SEQ ID NO: 11)
QVQLQQSGAELARPGASVKMSCKASGYTFTRYTMHWVKQRPGQGLE

WIGYINPSRGYTNYNQKFKDKATLTTDKSSSTAYMQLSSLTSEDSAVY

YCARYYDDHYSLDYWGQGTTLTVSSGOGGSGGGGSGGGGSQIVLTQS

PAIMSASPGEKVTMTCSASSSVSYMNWYQQKSGTSPKRWIYDTSKLAS

GVPAHFRGSGSGTSYSLTISGMEAEDAATYYCQQWSSNPFTFGSGTKL

EIKGSGSKVSVFVPPRDGFFGNPRKSKLICQATGFSPRQIQVSWLREGK

QVGSGVTTDQVQAEAKESGPTTYKVTSTLTIKESDWLSQSMFTCRVDH

RGLTFQQNASSMCVPDQDTAIRVFAIPPSFASIFLTKSTKLTCLVTDLTT

YDSVTISWTRQNGEAVKTHTNISESHPNATFSAVGEASISEDDWNSGER

FTCTVTHTDLPSPLKQTISRPKGVALHRPDVYLLPPAREQLNLRESATIY

CLVEGFSPADVFVQWMQRGQPLSPEKYVTSAPMPEPQAPGRYFAHSE

LTVSEEEWNTGETYTCVVAHEALPNRVTERTVDKSTGK
```

The Okt2a chain has a calculated molecular weight about 62 kD without glycosylation and 68 kD including 4 N-glycosylation sites.

iv. Okt2b is composed of OKT3 (anti-CD3 antibody) scFv fused with CM2 to CM4 of human μ chain with C291S, L352S, T354K, H395V, and I397K mutations and tail piece deletion.

```
                                          (SEQ ID NO: 12)
QVQLQQSGAELARPGASVKMSCKASGYTFTRYTMHWVKQRPGQGLE

WIGYINPSRGYTNYNQKFKDKATLTTDKSSSTAYMQLSSLTSEDSAVY

YCARYYDDHYSLDYWGQGTTLTVSSGGGGSGGGGSGGGGSQIVLTQS

PAIMSASPGEKVTMTCSASSSVSYMNWYQQKSGTSPKRWIYDTSKLAS

GVPAHFRGSGSGTSYSLTISGMEAEDAATYYCQQWSSNPFTFGSGTKL

EIKGSGSKVSVFVPPRDGFFGNPRKSKLICQATGFSPRQIQVSWLREGK

QVGSGVTTDQVQAEAKESGPTTYKVTSTLTIKESDWLSQSMFTCRVDH

RGLTFQQNASSMCVPDQDTAIRVFAIPPSFASIFLTKSTKLTCLVTDLTT

YDSVTISWTRQNGEAVKTHTNISESHPNATFSAVGEASISEDDWNSGER

FTCTVTHTDLPSPLKQTISRPKGVALHRPDVYLLPPAREQLNLRESATIT

CSVKGFSPADVFVQWMQRGQPLSPEKYVTSAPMPEPQAPGRYFAVSKL

TVSEEEWNTGETYTCVVAHEALPNRVTERTVDKSTGK
```

The Okt2b chain has a calculated molecular weight about 62 kD without glycosylation and 68 kD including 4 N-glycosylation sites.

2. Protein Expression, Purification and Characterization a. Transfection

IgM was made by co-transfection of several different expression vectors at equal molar ratios into mammalian cells, such as 293F cells (Invitrogen). 10 μg of mixed DNA for expression vectors were mixed with 20 μl of 293Fectin (Invitrogen) for 30 minutes at room temperature in 2 ml of Opti-MEM (Invitrogen) and then added to $10^7$ 293F cells. Transfections with 293F cells were incubated for 72 hours post-transfection before harvesting the supernatant.

b. Protein Purification by Immunoprecipitation.

i. Capture Select IgM (Catalog 2890.05, BAC, Thermo Fisher)

Transfected supernatant were harvested by centrifugation at 2,000 G for 10 minutes. IgM proteins were purified by immunoprecipitation with affinity Capture Select IgM affinity matrix. 100 μl of Capture Select IgM slurry were added to 15 ml of harvested supernatant. The supernatant and affinity matrix mixtures were incubated at room temperature for 2 hours on a rocker. The affinity matrices were then centrifuged at 300 g for 2 minutes, decanting the solution. The affinity matrixes were further washed with PBS plus 0.05% Tween for 3 times. Finally, the purified IgM proteins were washed off from affinity matrices by incubating 20 μl of 4×LSD sample loading buffer (Invitrogen) at room temperature for 5 minutes, followed by centrifuging at 10,000 g. The affinity matrixes were further washed with 60μl of PBS and the supernatant were pooled for analysis by gel electrophoresis.

c. Gel Electrophoresis i. Non-Reducing SDS PAGE

Non-reducing SDS PAGE was used to separate various mutant IgM proteins of different molecular weights. Novex 4-12% Bis-Tris Gel (Life Technologies) was used with Novex MES SDS Running Buffer (Life Technologies).

ii. Reducing SDS-PAGE

NuPage LDS sample buffer (Life Technologies) and NuPage reducing agent dithiothreitol (Life Technologies) were added to IgM protein samples and heated to 80° C. for 10 minutes before loading on NuPage Novex 4-12% Bis-Tris Gel (Life Technologies, cat# NP0322). NuPage MES SDS Running Buffer (Life Technologies, cat# NP0002) was used for gel electrophoresis. After electrophoresis is complete, the gel was removed from the apparatus and stained using Colloidal Blue Staining (Life Technologies, manual #LC6025.

iii. Gel Band Quantitation

Protein gels are dried, then digitized using image scanner. The gel images are processed with Image J program and the amount of protein in a specific band is determined using the gel quantitation function.

iv. Analysis of SDS-PAGE Gels

Rtx:Fc including wild-type and engineered IgM Fc pair 2a and 2b SDS-PAGE gels. Lanes 1, 2, and 3 on the non-reduced SDS-PEG gel (FIG. 6) show an upper band for homodimeric Rtx (H2L2, expected MW 168-180 kDa) and a lower band for half-antibody (HL, expected MW 84-90 kDa) for Rtx2a alone, Rtx2b alone and wild-type Rtx. A band for unassociated Fc (expected MW 36-41 kDA) is present in all three lanes; associated Fc (expected MW 72-82 kDa) may also be a component of the 80-90 kDa band. Lane 2 shows the mixture of Rtx2a:Fc2b and lane 3 shows the mixture of Rtx2b:Fc2a. In both lanes heterodimer (expected MW 120-131 kDa) is indicated with an arrow. The engineered Rtx2a:Fc2b and Rtx2b:Fc2a combinations both show the presence of significant heterodimer whereas the wild-type Rtx:Fc combination shows only a small amount of heterodimer.

The Fc is indeed present as seen in lanes 1-3 of the reduced SDS-PAGE shown in FIG. 7: top band is Rtx heavy chain (expected MW 61-67 kDa), middle band is Fc (expected MW 36-41 kDa), and bottom band is Rtx light chain (expected MW 23 kDa).

Okt:Fc including wild-type and engineered IgM Fc pair 2a and 2b, SDS-PAGE, FIG. 8, lanes 1-3

Wild-type Okt:Fc combination (SDS-PAGE, FIG. 8, lane 1) shows an upper band of Okt:Fc heterodimer (expected MW 98-107 kDa), a bottom band for unassociated Fc (expected MW 36-41) and a large middle band representing associated Fc (expected MW 72-82). In contrast, for the Okt2a:Fc2b and Okt2b:Fc2a combinations, the SDS-PAGE gel shown in FIG. 8, lane 2 shows a prominent band for the heterodimer and very light bands for associated Fc2b and the Okt2a homodimer above and congruent with the Okt2a:Fc2b heterodimer. The arrow indicates the heterodimer.

Both the Okt2a and Fc2b are present in the reduced gel (SDS-PAGE gel shown in FIG. 9, lane 2). Similar results are seen for the Okt2b:Fc2a pair on gels shown in FIGS. 8 and 9.

Okt:Rtx including wild-type and engineered IgM Fc pair 2a and 2b SDS-PAGE gels shown in FIGS. 8 and 9, lanes 4-6

Wild-type Okt:Rtx combination (SDS-PAGE gel shown in FIG. 8, lane 4) shows a band of wt Rtx homodimer (H2L2, expected MW 168-180 kDa), a band of wt Rtx half-antibody (HL, expected MW 84-90 kDa) and a light band that may be Okt homodimer (expected MW 124-133 kDa). In contrast, the engineered Okt2a:Rtx2b combination (SDS-PAGE gel shown in FIG. 8, lane 5) shows the presence of significant heterodimer (expected MW 146-157) as well as Rtx2b homodimer (expected MW 168-180 kDa) and half-antibody (expected MW 84-90 kDa). When reduced (SDS-PAGE gel shown in FIG. 9, lane 5), the Rtx2b light chain shows a band at MW 23 kDa; the heavy band between 60-80 kDA is likely comprised of Rtx2b heavy chain (expected MW 61-67 kDa) and Okt2a heavy chain (expected MW 62-67 kDa). Similar results are seen for the Okt2b:Rtx2a pair.

Conclusions:

For all three systems tested—Okt:Rtx, Okt:Fc, Rtx:Fc—the engineered IgM Fc variants showed substantially increased heterodimer formation compared to native (non-engineered) IgM Fc. A single pair of sequences (i.e., Fcs 2a and 2b) were tested and additional variants of the engineered Fc interface can be evaluated to further reduce homodimer formation and optimize heterodimer formation.

3. Bispecific Functional Analysis a. ELISA Analysis for Two Ligands

IgM with OKT3 (chain A) and cMyc peptide (chain B) is assayed by ELISA analysis with soluble CD3 epsilon protein capture and anti-cMyc (9E10) detection. Soluble CD3e protein is coated on ELISA plate at 2 mg/ml in 150 mM of $NaHCO_3$ followed by blocking with 3% BSA in PBS. Supernatant (100 µl) containing transfected IgM-OKT3-cMyc is added to blocked ELISA plate for 4 hours at 25 C. After washing with PBS, the 9E10 antibody is added to the ELISA plate for 2 hours at room temperature. Anti-mouse IgG-HRP is added following washes with PBS. The existence of bi-specific IgM is detected by reading with OD 450 after adding HRP substrate.

IgM with Okt3 (chain A) and Rituxan (chain B) is assayed by ELISA analysis with soluble CD3 epsilon protein capture and Protein-L-HRP detection. Soluble CD3e protein is coated on ELISA plate at 2 mg/ml in 150 mM of $NaHCO_3$ following by blocking with 3% BSA in PBS. Supernatant (100 µl) containing transfected IgM-Okta:Rtxb or Oktb:Rtxa is added to blocked ELISA plate for 4 hours at 25 C. After washing with PBS, the Protein-L-HRP is added to the ELISA plate for 2 hours at room temperature. The existence of bi-specific IgM is detected by reading with OD 450 after adding HRP substrate.

b. FACS Analysis of Target Binding

IgM-OKT3-cMyc binding to T cell is confirmed by binding of antibody to T cell line (Peer, positive cell line) and B cell line (Daudi, negative control cell line). After washing, rhodamine labeled 9E10 is added to the cell suspension. The cell target binding is detected by MFI of both positive and negative controlled cells with or without CD20 antigen.

c. Fluorescent Microscopy Assay for Bispecific Binding

Verify bispecific binding of the designed IgM by its ability to bring together, two populations of CD3 positive cells and CD20 positive cells, which have been pre-labeled by two different vital dyes on each cell type. For example:

i. Green Fluorescent cytosolic vital dye (CellTrace™ Calcein Green AM) labeling for CD3 positive cell line (Peer)

ii. Red Fluorescent cytosolic vital dye (CellTrace™ Calcein Red-Orange, AM) labeled CD20 positive B-cell cell line (Daudi)

Example 2

1. Generation of DNA Constructs with Designed Mutations

DNA construct synthesis and construction of expression vectors are performed as in Example 1.

a. µ Chains of Different Size

The A chain is composed of a full length µ chain for chimeric OKT3 (anti-CD3) Vh region fused with CM1 of human mu chain:

```
                                          (SEQ ID NO: 13)
QVQLQQSGAELARPGASVKMSCKASGYTFTRYTMHWVKQRPGQGLEWIG

YINPSRGYTNYNQKFKDKATLTTDKSSSTAYMQLSSLTSEDSAVYYCAR

YYDDHYCLDYWGQGTTLTVSSGSASAPTLFPLVSCENSPSDTSSVAVGC

LAQDFLPDSITFSWKYKNNSDISSTRGFPSVLRGGKYAATSQVLLPSKD

VMQGTDEHVVCKVQHPNGNKEKNVPLPVIAELPPKVSVFVPPRDGFFGN

PRKSKLICQATGFSPRQIQVSWLREGKQVGSGVTTDQVQAEAKESGPTT

YKVTSTLTIKESDWLSQSMFTCRVDHRGLTFQQNASSMCVPDQDTAIRV

FAIPPSFASIFLTKSTKLTCLVTDLTTYDSVTISWTRQNGEAVKTHTNI

SESHPNATFSAVGEASICEDDWNSGERFTCTVTHTDLPSPLKQTISRPK
```

GVALHRPDVYLLPPAREQLNLRESATITCLVTGFSPADVFVQWMQRGQP

LSPEKYVTSAPMPEPQAPGRYFAHSILTVSEEEWNTGETYTCVVAHEAL

PNRVTERTVDKSTGKPTLYNVSLVMSDTAGTCY

The A chain has a molecular weight about 63 kD and is able to bind to soluble epsilon chain of CD3 (10977-H08H, Sino Biological), or T cells.

The B chain has a cMyc tag fused with CH2 of human μ chain:

(SEQ ID NO: 14)
QVQLGGPEQKLISEEDLNSAVLPVIAELPPKVSVFVPPRDGFFGNPRKS

KLICQATGFSPRQIQVSWLREGKQVGSGVTTDQVQAEAKESGPTTYKVT

STLTIKESDWLSQSMFTCRVDHRGLTFQQNASSMCVPDQDTAIRVFAIP

PSFASIFLTKSTKLTCLVTDLTTYDSVTISWTRQNGEAVKTHTNISESH

PNATFSAVGEASICEDDWNSGERFTCTVTHTDLPSPLKQTISRPKGVAL

HRPDVYLLPPAREQLNLRESATITCLVTGFSPADVFVQWMQRGQPLSPE

KYVTSAPMPEPQAPGRYFAHSILTVSEEEWNTGETYTCVVAHEALPNRV

TERTVDKSTGKPTLYNVSLVMSDTAGTCY

The B chain has a molecular weight about 41 kD and is able to bind to anti-myc monoclonal antibody 9E4 or other anti-myc antibodies.

The alternative B chain has a full length μ chain for CrossMab$^{M\text{-}CL}$ (V$_H$+C$_L$) Rituximab (anti-CD20) fused with CH2 of human mu chain:

(SEQ ID NO: 15)
QVQLQQPGAELVKPGASVKMSCKASGYTFTSYNMHWVKQTPGRGLEWIG

AIYPGNGDTSYNQKFKGKATLTADKSSSTAYMQLSSLTSEDSAVYYCAR

STYYGGDWYFNVWGAGTTVTVSASVAAPSVFIFPPSDEQLKSGTASVVC

LLNNFYPREAKVQWKVDNALQSGNSQESVTEQDSKDSTYSLSSTLTSLK

ADYEKHKVYACEVTHQGLSSPVTKSFNRGECDKTHLPVIAELPPKVSVF

VPPRDGFFGNPRKSKLICQATGFSPRQIQVSWLREGKQVGSGVTTDQVQ

AEAKESGPTTYKVTSTLTIKESDWLSQSMFTCRVDHRGLTFQQNASSMC

VPDQDTAIRVFAIPPSFASIFLTKSTKLTCLVTDLTTYDSVTISWTRQN

GEAVKTHTNISESHPNATFSAVGEASICEDDWNSGERFTCTVTHTDLPS

PLKQTISRPKGVALHRPDVYLLPPAREQLNLRESATITCLVTGFSPADV

FVQWMQRGQPLSPEKYVTSAPMPEPQAPGRYFAHSILTVSEEEWNTGET

YTCVVAHEALPNRVTERTVDESTGKPTLYNVSLVMSDTAGTCY

The B chain has a molecular weight about 64 kD and is able to bind to CD20 positive B cells.

b. Different Light Chain Coupling
Native chimeric OKT3 kappa chain (SEQ ID NO: 16)
QIVLTQSPAIMSASPGEKVTMTCSASSSVSYMNWYQQKSGTSPKRWIYD

TSKLASGVPAHFRGSGSGTSYSLTISGMEAEDAATYYCQQWSSNPFTFG

SGTKLEINRAVAAPSVFIFPPSDEQLKSGTASVVCLLNNFYPREAKVQW

KVDNALQSGNSQESVTEQDSKDSTYSLSSTLTLSKADYEKHKVYACEVT

HQGLSSPVTKSFNRGEC

CrossMab$^{CM1\text{-}CL}$ for Rituximab (SEQ ID NO: 17)
QIVLSQSPAILSASPGEKVTMTCRASSSVSYIHWFQQKPGSSPKPWIYA

TSNLASGVPVRFSGSGSGTSYSLTISRVEAEDAATYYCQQWTSNPPTFG

GGTKLEIKSSASTKGPSVFPLAPSSKSTSGGTAALGCLVKDYFPEPVTV

SWNSGALTSGVHTFPAVLQSSGLYSLSSVVTVPSSSLGTQTYICNVNHK

PSNTKVDKRVEPKSC c. Different Selection Markers for Different Expression Vectors

Different selection markers are used on different expression vectors used for co-transfection. Multiple drugs are used for selection of cells in order to accommodate all necessary expression vectors relevant for IgM production. Standard molecular biology techniques are used for cloning specific DNAs into these vectors.

i. Mu chain utilizes Zeocin selection (ant-zn-1, Invivogen). Zeocin is used at a concentration of 100 μg/ml. After transfection with a plasmid containing the Sh ble gene, then the cells are incubated in Opti-CHO medium containing Zeocin at 100 μg/ml to select for stable transfectants.

ii. Kappa chain utilizes Blasticidin S selection (ant-bl-1, Invivogen). Blasticidin S is used at a concentration of 10 μg/ml. After transfection with a plasmid containing the bsr gene, then the cells are incubated in Opti-CHO medium containing Blasticidin S at 10 μg/ml to select for stable transfectants.

d. Protein Expression, Purification and Characterization
i. Transfection

IgM is made by co-transfection of several different expression vectors at equal molar ratios or variable molar ratio (5 to 10 fold difference) into mammalian cells, such as 293 cells or CHO cells. DNA for expression vectors are mixed with PEI and then added to CHO-S cells. PEI transfection with CHO-S cells is conducted according to established techniques (see "Biotechnology and Bioengineering, Vol 87, 553-545").

ii. Protein Purification

Capture Select IgM (Catalog 2890.05, BAC, Thermo Fisher)
  IgM proteins from transfected CHO-S cell supernatants are purified by affinity Capture Select IgM affinity matrix according to manufacturers' protocol.
Capto-L (Catalog 17-5478-01, GE Healthcare)
  Transfected IgM protein, containing kappa chain, in CHO-S cell supernatant is purified by Capto-L affinity matrix according to manufacturers' protocol iii. Gel Electrophoresis
Non-Reducing SDS PAGE Non-reducing SDS PAGE separates native IgM and its mutant forms according to size. Pentamic IgM, composed of homodimeric heavy chains (AA), produces a protein band of approximately 1,000,000 molecular weight. Pentameric IgM composed of a shorter version of homodimeric heavy chains (BB) produces a protein band of significantly lower molecular weight. Pentameric IgM composed of heterodimeric heavy chains (chimeric AB) produce multiple proteins with molecular weights greater than BB and less than AA.

NuPage LDS Sample Buffer (Life Technologies) is added to IgM protein samples at 25 C for 30 minutes before loading onto the gel. NativePage Novex 3-12% Bis-Tris Gel (Life Technologies) is used with Novex Tris-Acetate SDS Running Buffer (Life Technologies). Run gel until the dye front reaches the bottom of the gel.

Reducing SDS-PAGE

NuPage LDS sample buffer (Life Technologies) and NuPage reducing agent dithiothreitol (Life Technologies) are added to IgM protein samples and heated to 80° C. for 10 minutes before loading on NuPage Novex 4-12% Bis-Tris Gel (Life Technologies, cat# NP0322). NuPage MES SDS Running Buffer (Life Technologies, cat# NP0002) is used for gel electrophoresis. Gels are run until the dye front reaches the bottom of the gel.

After electrophoresis is complete, remove gel from apparatus and stain the gel using Colloidal Blue Staining (Life Technologies, manual #LC6025)

Gel Band Quantitation

Protein gels are dried, then digitized using image scanner. The gel image is processed with Image J program and the amount of protein in a specific band can be determined using the gel quantitation function iv. Mass Spectrometric Analysis to Identify/Quantify the Various mAbs in the Bi-Specific Preparation.

v. Stability Analysis Using Differential Scanning Calorimetry (DSC)

e. Bi-Specific Functional Analysis i. ELISA Analysis for Two Ligands

IgM with OKT3 (chain A) and cMyc peptide (chain B) is assayed by ELISA analysis with soluble CD3 epsilon protein capture and anti-cMyc (9E10) detection. Soluble CD3e protein is coated on ELISA plate at 2 mg/ml in 150 mM of $NaHCO_3$ followed by blocking with 3% BSA in PBS. Supernatant (100 μl) containing transfected IgM-OKT3-cMyc is added to blocked ELISA plate for 4 hours at 25 C. After washing with PBS, the 9E10 antibody is added to the ELISA plate for 2 hours at room temperature. Anti-mouse IgG-HRP is added following washes with PBS. The existence of bi-specific IgM is detected by reading with OD 450 after adding HRP substrate.

ii. FACS Analysis of Target Binding

IgM-OKT3-cMyc binding to T cell is confirmed by binding of antibody to T cell line (Peer, positive cell line) and B cell line (Daudi, negative control cell line). After washing, rhodamine labeled 9E10 is added to the cell suspension. The cell target binding is detected by MFI of both positive and negative controlled cells with or without CD20 antigen.

iii. Fluorescent Microscopy Assay for Bi-Specific Binding

Verify bi-specific binding of the designed IgM by its ability to bring together, two populations of CD3 positive cells and CD20 positive cells, which have been pre-labeled by two different vital dyes on each cell type. For example:

Green Fluorescent cytosolic vital dye (CellTrace™ Calcein Green AM) labeling for CD3 positive cell line (Peer)

Red Fluorescent cytosolic vital dye (CellTrace™ Calcein Red-Orange, AM) labeled CD20 positive B-cell cell line (Daudi)

Multi-specific binding and multi-specific functional analysis can be performed in a similar manner using techniques known in the art, such as those described above.

The invention claimed is:

1. A binding molecule having a penta- or hexameric ring structure comprising five or six bispecific binding units, wherein each of said bispecific binding units has the same two binding specificities and comprises a first chain comprising at least a Cµ4 domain, a Cµ3 domain, and a Cµ2 domain of a human IgM heavy chain constant region conjugated to a first binding region to a first binding target, and a second chain comprising at least a Cµ4, a Cµ3 domain, and a Cµ2 domain of a human IgM heavy chain constant region conjugated to a second binding region to a second binding target, wherein said first and second binding targets are different, and wherein said first and second chains are assembled to create a bispecific binding unit as a result of an asymmetric interface created between their respective IgM heavy chain constant regions, wherein the asymmetric interface is created by (i) a salt bridge formed by one or more pair-wise switches between oppositely charged amino acid residues in at least one of the Cµ2, Cµ3 and/or Cµ4 domains of the two chains of said binding unit, wherein the one or more pair-wise switches between oppositely charged amino acid residues comprise:

Cµ4 R328E,D↔Cµ4 E339R,K;
Cµ4 R344E,D↔Cµ4 D330R,K;
Cµ4 K376E,D↔Cµ4 E385R,K;
Cµ4 R427E,D↔Cµ4 E339R,K;
Cµ4 T354E,D↔Cµ4 I397R,K;
Cµ2 E167R,K↔Cµ2 K177E,D;
Cµ2 K169E,D↔Cµ2 E170R,K;
Cµ2 D121K,R↔Cµ4 K315D,E;
or
Cµ2 K185D,E↔Cµ4 D360K,R;
or
(ii) through knobs-into-holes connections comprising: knob T350Y and holes L352S and H395V; or knobs T350Y, T354E, and I397E and holes L352S, T354K, H395V, and I397K; and
wherein the amino acid coordinates correspond to the wild-type human IgM heavy chain constant region of SEQ ID NO: 33.

2. The binding molecule of claim 1, wherein said bispecific binding units are identical.

3. The binding molecule of claim 1, wherein said first and second binding regions are two different IgM antibody heavy chain variable regions, binding to said first and said second binding targets, respectively.

4. The binding molecule of claim 3, further comprising at least one IgM light chain variable region sequence associated with at least one of said two different IgM heavy chain variable regions.

5. The binding molecule of claim 4, wherein said light chain variable region sequence is coupled to its matching heavy chain variable region by creating an asymmetric interface between the light and heavy chains.

6. A multi-specific binding molecule having a penta- or hexameric ring structure comprising five or six bispecific binding units, wherein (i) each of said bispecific binding units comprises two human IgM heavy chain constant regions each comprising at least a Cµ2, Cµ3 and Cµ4 domain conjugated to a binding region to a binding target, (ii) at least two of said bispecific binding units bind to different binding targets, (iii) an internal asymmetric interface is created between two IgM heavy chain constant regions of each bispecific binding unit, and (iv) an external asymmetric interface is created between the heavy chain constant regions of the neighboring bispecific binding units binding to different targets, wherein the internal asymmetric interface is created by: (a) a salt bridge formed by one or more pair-wise switches between oppositely charged amino acid residues in at least one of the Cµ2, Cµ3 and/or Cµ4 domains of the two chains of said binding unit, wherein the one or more pair-wise switches between oppositely charged amino acid residues comprise:

Cµ4 R328E,D↔Cµ4 E339R,K;
Cµ4 R344E,D↔Cµ4 D330R,K;
Cµ4 K376E,D↔Cµ4 E385R,K;
Cµ4 R427E,D↔Cµ4 E339R,K;
Cµ4 T354E,D↔Cµ4 I397R,K;
Cµ2 E167R,K↔Cµ2 K177E,D;
Cµ2 K169E,D↔Cµ2 E170R,K;
Cµ2 D121K,R↔Cµ4 K315D,E;

or

Cµ2 K185D,E↔Cµ4 D360K,R or (b) through knobs-into-holes connections comprising:
knob T350Y and holes L352S and H395V; or knobs T350Y, T354E, and I397E and holes L352S, T354K, H395V, and I397K; and wherein the amino acid coordinates correspond to the wild-type human IgM heavy chain constant region of SEQ ID NO: 33.

7. The multi-specific binding molecule of claim 6, wherein the external asymmetric interface is created by at least one pair-wise charged amino acid residue switch in the Cµ3-Cµ3 domains.

8. The multi-specific binding molecule of claim 7, wherein the pair-wise charged amino acid switch in the Cµ3-Cµ3 domain is K238↔D293 or K268↔D294, the amino acid coordinates corresponding to the wild-type human IgM heavy chain constant region of SEQ ID NO:33.

9. A multi-specific binding molecule having a penta- or hexameric ring structure comprising five or six monospecific binding units, wherein (i) each of said monospecific binding units comprises two human IgM heavy chain constant regions each comprising at least a Cµ2, Cµ3 and Cµ4 domain conjugated to a binding region to a binding target, (ii) at least two of said monospecific binding units bind to different binding targets, and (iii) an external asymmetric interface is created between the heavy chain constant regions of the neighboring monospecific binding units that bind to different binding targets, wherein the external asymmetric interface is created by at least one pair-wise charged amino acid residue switch in the Cµ3-Cµ3 domains, wherein the pair-wise charged amino acid switch is K238↔D293 or K268↔D294, and wherein the amino acid coordinates correspond to the wild-type human IgM heavy chain constant region of SEQ ID NO: 33, and wherein the pair-wise charged amino acid switch is selected from the group consisting of K→E, K→D, D→K, and D→R.

10. The multi-specific binding molecule of claim 9 or claim 6, further comprising at least one IgM light chain variable region sequence associated with at least one of said two different IgM heavy chain variable regions.

11. The multi-specific binding molecule of claim 10, wherein said light chain variable region sequence is coupled to its matching heavy chain variable region by creating an asymmetric interface between the light and heavy chains.

12. The binding molecule of any one of claim 1, 9, or 6, wherein the binding targets are selected from peptides, polypeptides, glycoproteins, nucleic acid molecules, organic and non-organic small molecules, such as soluble polypeptides, cell surface receptors, ligands, molecular transporters, enzymes and substrates of enzymes.

13. The binding molecule of any one of claim 1, 9, or 6, wherein the binding units binding to different targets are selected from the group consisting of binding units binding to sites on the same soluble target; sites on the same cell surface receptor target; different soluble targets; different cell surface receptor targets; soluble and cell surface receptor targets; soluble or cell surface receptor and long residence time targets; soluble and matrix protein or substrate targets; soluble or receptor and molecular transporter targets, and different cell types.

14. The binding molecule of any one of claim 1, 9, or 6, further comprising an IgM J chain.

15. The binding molecule of any one of claim 1, 9, or 6, wherein at least one of said binding regions is a variable region of an antibody, such as an IgM antibody.

16. The binding molecule of any one of claim 1, 9, or 6, conjugated to a toxin or a chemotherapeutic agent.

17. The binding molecule according to claim 16, wherein the conjugation is by fusion or by a chemical linker.

18. The binding molecule of any one of claim 1, 9, or 6, which is chimeric or humanized.

19. A pharmaceutical composition comprising the binding molecule according to any one of claims 1, 9, 6, and a pharmaceutically acceptable carrier.

20. A pharmaceutical composition comprising the binding molecule according to claim 16 and a pharmaceutically acceptable carrier.

21. A method of treating a subject having cancer, the method comprising administering an effective amount of the pharmaceutical composition according to claim 19 to the subject.

22. A method of treating a subject having cancer, the method comprising administering an effective amount of the pharmaceutical composition according to claim 20 to the subject.

* * * * *

UNITED STATES PATENT AND TRADEMARK OFFICE
CERTIFICATE OF CORRECTION

PATENT NO. : 10,351,631 B2
APPLICATION NO. : 14/916166
DATED : July 16, 2019
INVENTOR(S) : Bruce Alan Keyt et al.

Page 1 of 1

It is certified that error appears in the above-identified patent and that said Letters Patent is hereby corrected as shown below:

In the Claims

Column 94, Line 3, Claim 12, replace "any one of claim 1, 9, or 6," with --any one of claims 1, 9, or 6--

Column 94, Line 9, Claim 13, replace "any one of claim 1, 9, or 6," with --any one of claims 1, 9, or 6--

Column 94, Line 20, Claim 14, replace "any one of claim 1, 9, or 6," with --any one of claims 1, 9, or 6--

Column 94, Line 22, Claim 15, replace "any one of claim 1, 9, or 6," with --any one of claims 1, 9, or 6--

Column 94, Line 25, Claim 16, replace "any one of claim 1, 9, or 6," with --any one of claims 1, 9, or 6--

Column 94, Line 29, Claim 18, replace "any one of claim 1, 9, or 6," with --any one of claims 1, 9, or 6--

Signed and Sealed this
Fifth Day of January, 2021

Andrei Iancu
*Director of the United States Patent and Trademark Office*